(12) United States Patent
Kawai et al.

(10) Patent No.: US 11,370,780 B2
(45) Date of Patent: *Jun. 28, 2022

(54) ADDITIVE FOR IMPARTING ULTRAVIOLET ABSORBENCY AND/OR HIGH REFRACTIVE INDEX TO MATRIX, AND RESIN MEMBER USING SAME

(71) Applicants: Miyoshi Oil & Fat Co., Ltd., Tokyo (JP); Tokai Optical Co., Ltd., Aichi (JP)

(72) Inventors: Koji Kawai, Tokyo (JP); Kotaro Kaneko, Tokyo (JP); Nobuhiro Kaneko, Tokyo (JP); Yuichi Shishino, Aichi (JP); Kuniyoshi Okamoto, Aichi (JP)

(73) Assignees: MIYOSHI OIL & FAT CO., LTD., Tokyo (JP); TOKAI OPTICAL CO., LTD., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/394,302

(22) Filed: Apr. 25, 2019

(65) Prior Publication Data

US 2019/0248766 A1 Aug. 15, 2019

Related U.S. Application Data

(63) Continuation of application No. 15/501,253, filed as application No. PCT/JP2015/072284 on Aug. 5, 2015, now Pat. No. 10,316,024.

(30) Foreign Application Priority Data

Aug. 5, 2014 (JP) ................. 2014-159910

(51) Int. Cl.
| | | |
|---|---|---|
| C07D 249/18 | (2006.01) | |
| C08K 5/37 | (2006.01) | |
| C08K 5/3475 | (2006.01) | |
| C07D 403/12 | (2006.01) | |
| C08K 5/372 | (2006.01) | |
| C09K 3/00 | (2006.01) | |
| C08L 101/00 | (2006.01) | |
| C07C 49/84 | (2006.01) | |
| C07C 69/94 | (2006.01) | |
| C07C 321/26 | (2006.01) | |
| C07C 321/28 | (2006.01) | |
| C07D 249/20 | (2006.01) | |
| C07D 251/24 | (2006.01) | |

(52) U.S. Cl.
CPC ............ *C07D 403/12* (2013.01); *C07C 49/84* (2013.01); *C07C 69/94* (2013.01); *C07C 321/26* (2013.01); *C07C 321/28* (2013.01); *C07D 249/20* (2013.01); *C07D 251/24* (2013.01); *C08K 5/3475* (2013.01); *C08K 5/37* (2013.01); *C08K 5/372* (2013.01); *C08L 101/00* (2013.01); *C09K 3/00* (2013.01)

(58) Field of Classification Search
CPC ....... C07D 249/18; C08K 5/3475; C08K 5/37
USPC ............................... 548/259, 260; 252/400.1
See application file for complete search history.

(56) References Cited

U.S. PATENT DOCUMENTS

| | | | |
|---|---|---|---|
| 4,054,682 | A | 10/1977 | Kuesters et al. |
| 5,250,698 | A | 10/1993 | Falk et al. |
| 5,298,380 | A | 3/1994 | Leppard |
| 6,166,218 | A | 12/2000 | Ravichandran et al. |

(Continued)

FOREIGN PATENT DOCUMENTS

| | | |
|---|---|---|
| CN | 1091127 | 9/2002 |
| CN | 101831176 | 9/2010 |

(Continued)

OTHER PUBLICATIONS

International Search Report dated Nov. 2, 2015 in corresponding International Application No. PCT/JP2015/072284.

(Continued)

*Primary Examiner* — Bruck Kifle
(74) *Attorney, Agent, or Firm* — Wenderoth, Lind & Ponack, L.L.P.

(57) ABSTRACT

Provided is an additive for imparting ultraviolet absorbency, or an additive for imparting a high refractive index, which has satisfactory compatibility with a resin serving as a matrix and can maintain high transparency even if added in high concentrations. Also provided is an additive with which the function of imparting both ultraviolet absorbency and a high refractive index can be realized by means of one kind of additive. This additive is represented by the following Formula (I):

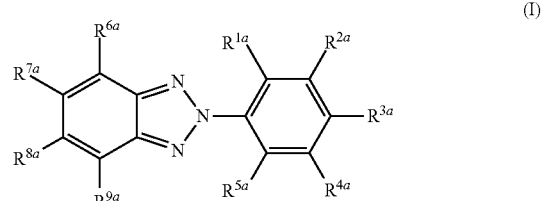

(I)

wherein at least one of $R^{1a}$ to $R^{9a}$ is a monovalent sulfur-containing group represented by the following Formula (i-1) or Formula (i-2):

$\mathrm{+(R^{10a})}_m\mathrm{SH}$ (i-1)

$\mathrm{+(R^{11a})}_n\mathrm{S+(R^{12a}-S)}_p\mathrm{R^{13a}}$ (i-2)

wherein $R^{10a}$ to $R^{12a}$ each represent a divalent hydrocarbon group or the like; and $R^{13a}$ represents a monovalent hydrocarbon group or the like.

36 Claims, 14 Drawing Sheets

(56) References Cited

U.S. PATENT DOCUMENTS 10,316,024 B2 * 6/2019 Kawai ................. C08K 5/3475
2013/0150479 A1 6/2013 Zhao et al.

FOREIGN PATENT DOCUMENTS

| EP | 0 599 269 | 6/1994 |
| EP | 0 675 108 | 10/1995 |
| JP | 05-197075 | 8/1993 |
| JP | 06-505743 | 6/1994 |
| JP | 06-505744 | 6/1994 |
| JP | 07-011138 | 1/1995 |
| JP | 2003-39830 | 2/2003 |
| JP | 2004-237638 | 8/2004 |
| WO | 92/14717 | 9/1992 |
| WO | 92/14718 | 9/1992 |

OTHER PUBLICATIONS

English Translation of the International Preliminary Report on Patentability dated Oct. 5, 2016 in corresponding International Application No. PCT/JP2015/072284.
Pccompound-1-77, Create Date Feb. 9, 2007 to Dec. 1, 2012.
Notification of Reasons for Refusal dated Sep. 3, 2019 in Japanese Patent Application No. 2016-540724, with English translation.
Second Examination Opinion Notification dated Sep. 18, 2019 in corresponding Chinese Patent Application No. 201580042213.3, with English translation.

* cited by examiner

| EXAMPLE OR COMPARATIVE EXAMPLE No. | COMPOUND No. | STRUCTURE | UV CHART (5μM) |
|---|---|---|---|
| EXAMPLE 36 | 1 | benzotriazole with O(CH$_2$)$_6$SH and Me substituents | peak at 289 nm, ABS ~0.6 |
| EXAMPLE 37 | 2 | benzotriazole with O(CH$_2$)$_{10}$SH and Me substituents | peak at 288 nm, ABS ~0.06 |
| EXAMPLE 38 | 3 | benzotriazole with HO and S(CH$_2$)$_7$CH$_3$ substituents | peak at 272 nm, ABS ~1.3 |
| EXAMPLE 39 | 4 | benzotriazole with HO and S(CH$_2$)$_3$S(CH$_2$)$_7$CH$_3$ substituents | peak at 275 nm, ABS ~0.7 |
| EXAMPLE 40 | 8 | benzotriazole with CH$_3$(CH$_2$)$_7$S, HO, t-Bu, and Me substituents | peak at 368 nm, ABS ~1.3 |

*FIG. 1*

| EXAMPLE OR COMPARATIVE EXAMPLE No. | COMPOUND No. | STRUCTURE | UV CHART (5 μM) |
|---|---|---|---|
| EXAMPLE 41 | 10 | benzotriazole with CH$_3$(CH$_2$)$_{11}$S substituent, HO, t-Bu, Me | peak 368 nm |
| EXAMPLE 42 | 11 | benzotriazole with CH$_3$(CH$_2$)$_{17}$S substituent, HO, t-Bu, Me | peak 365 nm |
| EXAMPLE 43 | 14 | benzotriazole with CH$_3$(CH$_2$)$_7$S(CH$_2$)$_3$S substituent, HO, t-Bu, Me | peak 369 nm |
| EXAMPLE 44 | 5 | benzotriazole with (CH$_2$)$_{11}$CH$_3$, HO, Me | peaks 303 nm, 345 nm |
| COMPARATIVE EXAMPLE 9 | 32 | benzotriazole with HO, O(CH$_2$)$_7$CH$_3$ | peak 346 nm |

FIG. 2

| EXAMPLE OR COMPARATIVE EXAMPLE No. | COMPOUND No. | STRUCTURE | UV CHART (100 μM) |
|---|---|---|---|
| EXAMPLE 45 | 6 | $CH_3(CH_2)_3S$ – benzotriazole – HO, t-Bu, Me | Peak 367 nm |
| EXAMPLE 46 | 7 | $CH_3(CH_2)_5S$ – benzotriazole – HO, t-Bu, Me | Peak 367 nm |
| EXAMPLE 47 | 8 | $CH_3(CH_2)_7S$ – benzotriazole – HO, t-Bu, Me | Absorption peak 367.5 nm; peak end; base line |
| EXAMPLE 48 | 9 | $CH_3(CH_2)_9S$ – benzotriazole – HO, t-Bu, Me | Peak 367.5 nm |
| EXAMPLE 49 | 10 | $CH_3(CH_2)_{11}S$ – benzotriazole – HO, t-Bu, Me | Peak 367.5 nm |

FIG. 3

| EXAMPLE OR COMPARATIVE EXAMPLE No. | COMPOUND No. | STRUCTURE | UV CHART (100μM) |
|---|---|---|---|
| EXAMPLE 50 | 11 | CH₃(CH₂)₁₇S-benzotriazole-HO-t-Bu, Me | peak at 367 nm |
| EXAMPLE 51 | 12 | CH₃(CH₂)₇S-benzotriazole-HO-t-Bu, t-Bu | peak at 366.5 nm |
| EXAMPLE 52 | 13 | CH₃(CH₂)₁₁S-benzotriazole-HO-t-Bu, t-Bu | peak at 366.5 nm |
| EXAMPLE 53 | 14 | CH₃(CH₂)₇S(CH₂)₃S-benzotriazole-HO-t-Bu, Me | peak at 367 nm |
| EXAMPLE 54 | 15 | C₂H₅CH(CH₃)S-benzotriazole-HO-t-Bu, Me | peak at 367 nm |

*FIG. 4*

| EXAMPLE OR COMPARATIVE EXAMPLE No. | COMPOUND No. | STRUCTURE | UV CHART (100 μM) |
|---|---|---|---|
| EXAMPLE 55 | 16 | 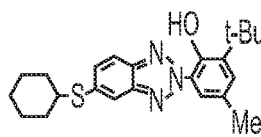 | 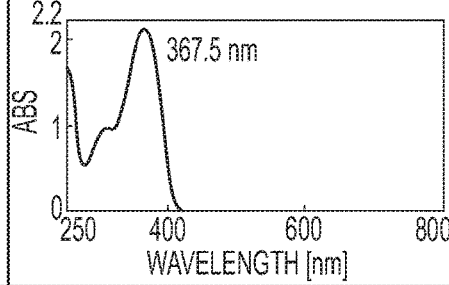 367.5 nm |
| EXAMPLE 56 | 17 | 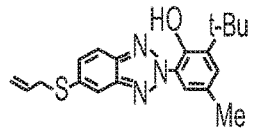 | 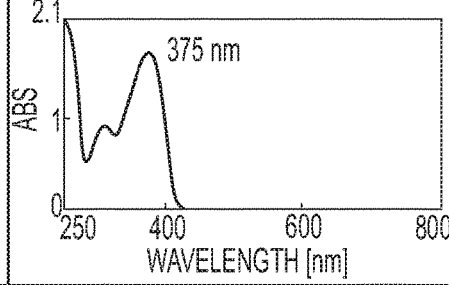 375 nm |
| EXAMPLE 57 | 18 | 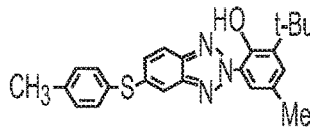 | 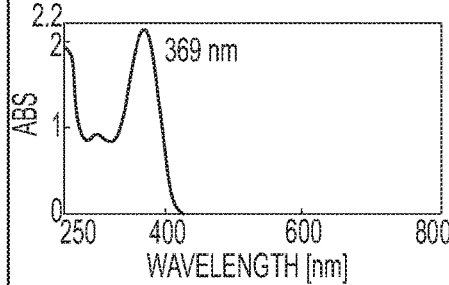 369 nm |
| EXAMPLE 58 | 19 | 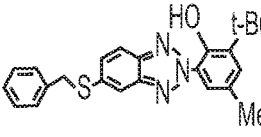 | 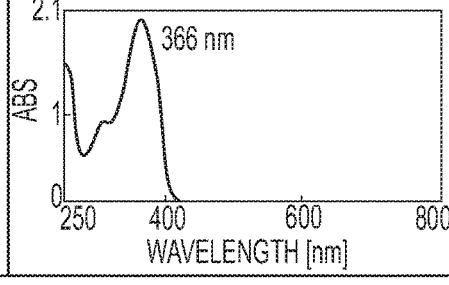 366 nm |
*FIG. 5A*

| EXAMPLE OR COMPARATIVE EXAMPLE No. | COMPOUND No. | STRUCTURE | UV CHART (100μM) |
|---|---|---|---|
| EXAMPLE 59 | 20 | benzotriazole with HO(CH₂)₂S- substituent, phenol with t-Bu and Me | peak at 364 nm |
| EXAMPLE 60 | 21 | bis-benzotriazole linked by S(H₂C)₆S bridge with two phenols (t-Bu, OH, Me) | peak at 367 nm |
| COMPARATIVE EXAMPLE 10 | 36 | chloro-benzotriazole with phenol (t-Bu, OH, Me) | peak at 353.5 nm |

FIG. 5B

| EXAMPLE OR COMPARATIVE EXAMPLE No. | COMPOUND No. | STRUCTURE | UV CHART (5μM) |
|---|---|---|---|
| EXAMPLE 61 | 22 | benzophenone with 2-OH and 4-SH | 302 nm, 339 nm |
| EXAMPLE 62 | 23 | $CH_3(CH_2)_7S$-C6H4-CO-C6H4-OH | 315 nm |
| EXAMPLE 63 | 24 | benzophenone with 2-OH and 4-$S(CH_2)_3S(CH_2)_7CH_3$ | 338 nm |
| EXAMPLE 64 | 25 | $CH_3(CH_2)_7S(CH_2)_3S$-C6H4-CO-C6H4-OH | 313 nm |
| COMPARATIVE EXAMPLE 11 | 33 | benzophenone with 2-OH and 4-$O(CH_2)_7CH_3$ | 290 nm, 330 nm |

*FIG. 6*

| EXAMPLE OR COMPARATIVE EXAMPLE No. | COMPOUND No. | STRUCTURE | UV CHART (5μM) |
|---|---|---|---|
| EXAMPLE 65 | 26 | 2-hydroxybenzoate ester with 3-(hexylthio)phenol | Peaks at 242 nm (ABS ~0.13) and 310 nm (ABS ~0.05); wavelength range 250–800 nm |
| EXAMPLE 66 | 27 | 3,5-di-t-Bu-4-hydroxybenzoate ester with 3-(hexylthio)phenol | Peak at 264 nm (ABS ~0.11); wavelength range 250–800 nm |
| COMPARATIVE EXAMPLE 12 | 34 | 3,5-di-t-Bu-4-hydroxybenzoate ester with 2,4-di-t-Bu-phenol | Peak at 266 nm (ABS ~0.08); wavelength range 250–800 nm |

*FIG. 7*

| EXAMPLE OR COMPARATIVE EXAMPLE No. | COMPOUND No. | STRUCTURE | UV CHART (5μM) |
|---|---|---|---|
| EXAMPLE 67 | 28 | triazine-phenyl₂, OH, SCH₃ substituted phenol | peaks at 276 nm, 359 nm |
| EXAMPLE 68 | 29 | tris(hydroxyphenyl) with S(CH₂)₅CH₃ groups | peak at 394 nm |
| EXAMPLE 69 | 30 | tris(hydroxyphenyl) with S(CH₂)₇CH₃ groups | peak at 393 nm |
| EXAMPLE 70 | 31 | triazine-phenyl₂, OH, S(CH₂)₅CH₃ substituted phenol | peaks at 274 nm, 360.5 nm |
| COMPARATIVE EXAMPLE 13 | 35 | triazine-phenyl₂, OH, O(CH₂)₅CH₃ substituted phenol | peaks at 275.5 nm, 341.5 nm |

*FIG. 8*

Fig. 17
Example 10: Compound 10 / acrylic melamine
Example 13: Compound 13 / acrylic melamine
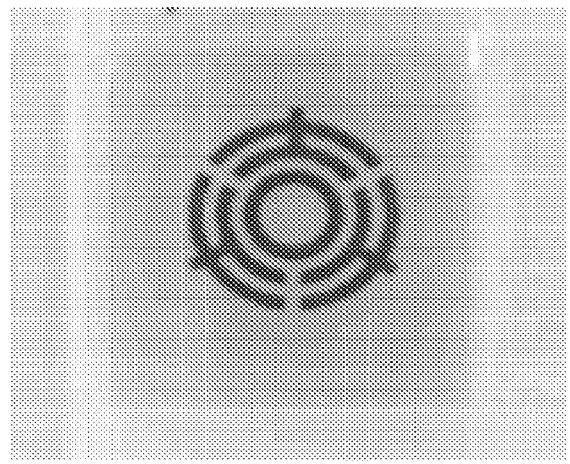
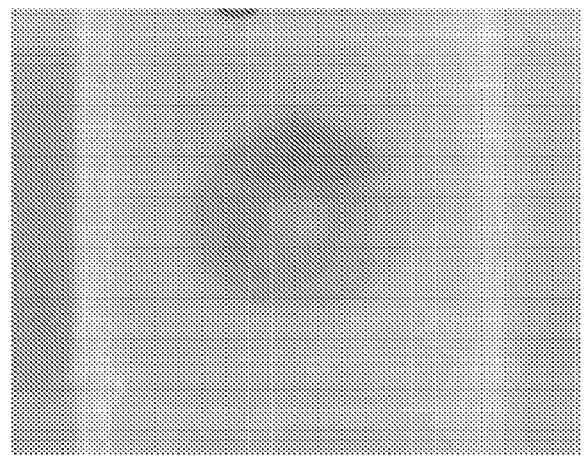

ADDITIVE FOR IMPARTING ULTRAVIOLET ABSORBENCY AND/OR HIGH REFRACTIVE INDEX TO MATRIX, AND RESIN MEMBER USING SAME

TECHNICAL FIELD

The present invention relates to an additive for enhancing ultraviolet absorbency or adjusting the refractive index when added to a matrix of a resin or the like, and to a resin member using the additive.

BACKGROUND ART

In regard to optical materials such as optical films and optical molded articles, it is important to impart optical functions such as ultraviolet absorption and refractive index adjustment, and various investigations have been conducted.

Resin members are deteriorated under the effect of ultraviolet ray and suffered quality degradation such as discoloration or lowering of mechanical strength, so that long-term use of resin members is inhibited. In order to prevent such quality degradation or to control the wavelength of transmitted light, it has been a general practice to incorporate an inorganic or organic ultraviolet absorber into a resin member.

Inorganic ultraviolet absorbers have excellent durability such as weather resistance or heat resistance; however, since the absorption wavelength is determined by the band gap of the compound, the degree of freedom of selection is low, and there are only few compounds that can absorb even up to the long-wavelength ultraviolet ray region near 400 nm (UV-A, 315 to 400 nm) in the near ultraviolet ray range. Meanwhile, those inorganic ultraviolet absorbers that can absorb long-wavelength ultraviolet ray have absorption of wavelength up to 450 to 500 nm (visible range), and therefore, they cause coloration. Members used in solar cells and the like, development of which has advanced in recent years, need to be exposed to sunlight for a long period of time in the outdoors, and deterioration of the properties of the members as a result of exposure to ultraviolet ray over a long period of time, cannot be avoided. Therefore, there is a demand for an ultraviolet absorber having excellent light resistance, which exhibits durability against yellowing of members, and also exhibits a shielding effect for up to the UV-A region.

In contrast, organic ultraviolet absorbers are such that since the degree of freedom of structural design for the absorbers is high, ultraviolet absorbers having various absorption wavelengths can be obtained by devising the structures of the absorbers. On the other hand, organic ultraviolet absorbers are such that when a resin composition including an ultraviolet absorber is heated and then is subjected to molding and processing, there is a possibility that the ultraviolet absorber may be thermally decomposed, and this decomposition of ultraviolet absorber may lead to decrease in the ultraviolet absorbency of the resin member, impairment of transparency in the case of a transparent resin member, and contamination of molding and processing apparatuses. Thus, there is a demand for an organic ultraviolet absorber having superior heat resistance. Regarding organic ultraviolet absorbers, benzotriazole-based, benzophenone-based, triazine-based, cyanoacrylate-based and salicylate-based ultraviolet absorbers are conventionally known (see, for example, Patent Literatures 1 to 4).

On the other hand, in optical films such as a reflective film, an antireflection film, and a hard coat film, it is required to adjust the refractive index in order to regulate the optical characteristics. Conventionally, refractive index adjusting agents have been added for the adjustment of the refractive index. Regarding the refractive index adjusting agents, inorganic oxide particles and the like are used to increase the refractive index.

Furthermore, it is preferable that transparent resin members containing ultraviolet absorbers including optical molded articles are transparent after molding or after a lapse of time in view of applications, and thus ultraviolet absorbers are needed from the viewpoint of preventing deterioration of optical characteristics caused by opacification or discoloration due to ultraviolet-induced degradation. Particularly for glasses lens or contact lenses, ultraviolet absorbers are needed from the viewpoint of protecting eyes from ultraviolet ray.

In glasses lens and the like, increase of the refractive index of the resin proceeds, and there are additives, such as an ultraviolet absorber, having refractive indices that are lower than that of the resin. In this case, as the refractive indices of the additives are lower, and the amounts of addition of the additives become larger, the overall refractive index of the resin is lowered. Therefore, there is a need for an ultraviolet absorber which has a higher refractive index and can be added in high concentrations.

CITATION LIST

Patent Literature

Patent Literature 1: JP 2012-184168 A
Patent Literature 2: JP 2005-504047 W
Patent Literature 3: JP 2013-67811 A
Patent Literature 4: JP 06-505744 W

SUMMARY OF INVENTION

Technical Problem

However, a significant number of conventional organic ultraviolet absorbers have limited compatibility with the resins of matrices, and uniform dissolution of their organic ultraviolet absorbers and resins in high concentrations has been difficult. Also, when the organic ultraviolet absorbers are added in high concentrations, the resins are caused cloudiness and impaired transparency. Therefore, in applications where high transparency is required, if it is wished to sufficiently manifest performances such as ultraviolet absorbency and provision of a high refractive index, there have been restrictions on the concentration of ultraviolet absorbers for the resins. Furthermore, conventional organic ultraviolet absorbers have a possibility of being thermally decomposed when a resin containing an ultraviolet absorber is heated and then is subjected to molding and processing, and an obtained resin member may have impaired ultraviolet absorbency, while a transparent resin member may have impaired transparency. Also, there is a risk that the molding processing apparatus may be contaminated.

That is, there has been a demand for an additive that has excellent heat resistance, has satisfactory compatibility with a resin that serves as a matrix, can sufficiently exhibit performances such as ultraviolet absorption and increased refractive index while maintaining high transparency of the resins, and can be dissolved to the resins in high concentrations.

Furthermore, there are only few studies concerning a technology which enables imparting of ultraviolet absorbency and a high refractive index by means of a single additive. For example, in the technologies specifically disclosed in Patent Literatures 1 to 3, no investigation was conducted on sulfur-containing compounds, and a high refractive index cannot be imparted. Therefore, in the field of optical materials such as optical films, optical sheets, optical plates (plate-like members), and other optical molded articles, for example, optical lenses such as glasses lens or the like, both functions of ultraviolet absorbency and refractive index characteristics are required in many case. However, in order to satisfy all of such requirements, an ultraviolet absorbing layer to which an ultraviolet absorber has been added, and a high refractive index layer to which a refractive index adjusting agent has been added are laminated as separate layers.

Patent Literature 4 discloses a 5-thio-substituted benzotriazole ultraviolet absorber. This ultraviolet absorber which protects organic substances against harmful action caused by exposure to ultraviolet ray and suppresses degradation of the organic substances over time provides a stabilized composition. However, investigations focused on heat resistance and high refractive index characteristics of the ultraviolet absorber, suitability to a transparent resin matrix, compatibility (transparency) with a resin serving as a matrix, suppression of yellowing of a resin matrix, provision of a high refractive index to a resin member containing the ultraviolet absorber, suppression of deterioration of the ultraviolet absorbency and external appearance of a resin member caused by thermal decomposition of the ultraviolet absorber, and deterioration of transparency and yellowing in a transparent resin member, have not been achieved in the study.

The present invention was achieved in view of such circumstances as described above, and it is a principal object to provide an additive for imparting ultraviolet absorbency, or an additive for imparting a high refractive index, which has satisfactory compatibility with a resin serving as a matrix, can maintain high transparency even if added in high concentrations, and has excellent heat resistance; and a resin member using the additive.

It is another object of the present invention to provide an excellent heat resistant additive having the function of imparting both ultraviolet absorbency and a high refractive index can be realized by means of one kind of additive while maintaining transparency of matrix; and a resin member using the additive.

Solution to Problem

In order to solve the problems described above, the additive of the present invention is an additive for imparting ultraviolet absorbency and/or a high refractive index to a matrix, the additive having the following features.

[1] An additive for imparting ultraviolet absorbency and/or a high refractive index to a matrix, the additive being represented by the following Formula (I):

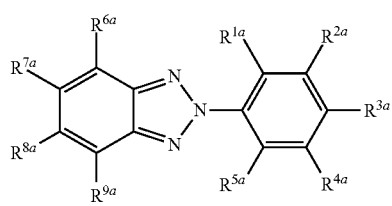

wherein in Formula (I), $R^{1a}$ to $R^{9a}$ each independently represent a monovalent group selected from a monovalent sulfur-containing group represented by the following Formula (i-1) or Formula (i-2), a hydrogen atom, a monovalent hydrocarbon group having 1 to 10 carbon atoms, an aromatic group, an unsaturated group, a sulfur-containing group, an oxygen-containing group, a phosphorus-containing group, an alicyclic group, and a halogen atom:

$$-(R^{10a})_m-SH \quad (i\text{-}1)$$

$$-(R^{11a})_n-S-(R^{12a}-S)_p-R^{13a} \quad (i\text{-}2)$$

wherein in Formula (i-1), $R^{10a}$ represents a divalent hydrocarbon group having 1 to 12 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; and m represents an integer of 0 or 1, and in Formula (i-2), $R^{11a}$ represents a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{12a}$ represents, or if p is 2 or larger, $R^{12a}$'s each independently represent, a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{13a}$ represents a hydrogen atom, or a group represented by $-(R^{14a})_l-R^{15a}$ (wherein $R^{14a}$ represents a divalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{15a}$ represents a hydrogen atom, or a substituent containing any one skeleton selected from benzotriazole, benzophenone, a benzoic acid ester and triazine; and l represents an integer of 0 or 1); the total number of carbon atoms of $R^{11a}$, p units of $R^{12a}$, and $R^{13a}$ is 25 or less; n represents an integer of 0 or 1; and p represents an integer from 0 to 3, with the proviso that at least one of $R^{1a}$ to $R^{9a}$ represents a monovalent sulfur-containing group represented by Formula (i-1) or Formula (i-2).

[2] The additive according to [1], wherein the matrix is a transparent resin.

[3] The additive according to [1] or [2], wherein the monovalent sulfur-containing group is a group represented by Formula (i-1), and in the monovalent sulfur-containing group represented by this Formula (i-1), m is 0, or m is 1, with $R^{10a}$ including an alkylene group having 10 or fewer carbon atoms.

[4] The additive according to [1] or [2], wherein the monovalent sulfur-containing group is a group represented by Formula (i-1), and in this monovalent sulfur-containing group represented by Formula (i-1), m is 0, or m is 1, with

[5] The additive according to [1] or [2], wherein the monovalent sulfur-containing group is a group represented by Formula (i-1), and in this monovalent sulfur-containing group represented by Formula (i-1), m is 0, or m is 1, with $R^{10a}$ including an alkylene group having 8 or fewer carbon atoms, while the additive has a melting point of below 70° C. at normal pressure.

[6] The additive according to [1] or [2], wherein the monovalent sulfur-containing group is a group represented by Formula (i-1), and in this monovalent sulfur-containing group represented by Formula (i-1), m is 0, or m is 1, with $R^{10a}$ including an alkylene group having 8 or fewer carbon atoms, while the additive has a melting point of 35° C. or lower at normal pressure.

[7] The additive according to [1] or [2], wherein the monovalent sulfur-containing group is a group represented by Formula (i-1), and in this monovalent sulfur-containing group represented by Formula (i-1), m is 0, or m is 1, with $R^{10a}$ being an oxyalkylene group having 10 or fewer carbon atoms and having an ether bond at the proximal terminal.

[8] The additive according to [1] or [2], wherein the monovalent sulfur-containing group is a group represented by Formula (i-2), and the additive has this monovalent sulfur-containing group represented by Formula (i-2) at any of the positions of $R^{1a}$ to $R^{5a}$.

[9] The additive according to [8], wherein in the monovalent sulfur-containing group represented by Formula (i-2), $R^{11a}$ and p units of $R^{12a}$ each include an alkylene group having 18 or fewer carbon atoms, and $R^{13a}$ includes an alkyl group having 18 or fewer carbon atoms.

[10] The additive according to [8], wherein in the monovalent sulfur-containing group represented by Formula (i-2), $R^{11a}$ and p units of $R^{12a}$ each include an alkylene group having 18 or fewer carbon atoms, and $R^{13a}$ includes an alkyl group having 18 or fewer carbon atoms, while the additive has a melting point of 91° C. or lower at normal pressure.

[11] The additive according to [8], wherein in the monovalent sulfur-containing group represented by Formula (i-2), $R^{11a}$ and p units of $R^{12a}$ each include an alkylene group having 12 or fewer carbon atoms, and $R^{13a}$ includes an alkyl group having 12 or fewer carbon atoms, while the additive has a melting point of 91° C. or lower at normal pressure.

[12] The additive according to [8], wherein in the monovalent sulfur-containing group represented by Formula (i-2), $R^{11a}$ and p units of $R^{12a}$ each include an alkylene group having 10 or fewer carbon atoms, and $R^{13a}$ includes an alkyl group having 10 or fewer carbon atoms, while the additive has a melting point of 91° C. or lower at normal pressure.

[13] The additive according to [8], wherein in the monovalent sulfur-containing group represented by Formula (i-2), $R^{11a}$ and p units of $R^{12a}$ each include an alkylene group having 10 or fewer carbon atoms, and $R^{13a}$ includes an alkyl group having 10 or fewer carbon atoms, while the additive has a melting point of below 70° C. at normal pressure.

[14] The additive according to [8], wherein in the monovalent sulfur-containing group represented by Formula (i-2), $R^{11a}$ and p units of $R^{12a}$ each includes an alkylene group having 8 or fewer carbon atoms, and $R^{13a}$ includes an alkyl group having 8 or fewer carbon atoms, while the additive has a melting point of below 70° C. at normal pressure.

[15] The additive according to [8], wherein in the monovalent sulfur-containing group represented by Formula (i-2), $R^{11a}$ and p units of $R^{12a}$ each includes an alkylene group having 8 or fewer carbon atoms, and $R^{13a}$ includes an alkyl group having 8 or fewer carbon atoms, while the additive has a melting point of 35° C. or lower at normal pressure.

[16] The additive according to [1] or [2], wherein the additive has a monovalent sulfur-containing group represented by Formula (i-2) at any of the positions of $R^{6a}$ to $R^{9a}$.

[17] The additive according to [16], wherein in the monovalent sulfur-containing group represented by Formula (i-2), n is 0, p units of $R^{12a}$ each include an alkylene group having 18 or fewer carbon atoms, and $R^{13a}$ includes an alkyl group having 18 or fewer carbon atoms.

[18] The additive according to [16], wherein in the monovalent sulfur-containing group represented by Formula (i-2), n is 0, p units of $R^{12a}$ each includes an alkylene group having 8 or fewer carbon atoms, and $R^{13a}$ includes an alkyl group having 8 or fewer carbon atoms, while the additive has a melting point of below 70° C. at normal pressure.

[19] The additive according to [16], wherein in the monovalent sulfur-containing group represented by Formula (i-2), n and p are each 0, and $R^{13a}$ includes an alkyl group having 18 or fewer carbon atoms.

[20] The additive according to [16], wherein in the monovalent sulfur-containing group represented by Formula (i-2), n and p are each 0, and $R^{13a}$ includes an alkyl group having 18 or fewer carbon atoms, while the additive has a melting point of 91° C. or lower at normal pressure.

[21] The additive according to [16], wherein in the monovalent sulfur-containing group represented by Formula (i-2), n and p are each 0, and $R^{13a}$ includes an alkyl group having 12 or fewer carbon atoms, while the additive has a melting point of 91° C. or lower at normal pressure.

[22] The additive according to [16], wherein in the monovalent sulfur-containing group represented by Formula (i-2), n and p are each 0, and $R^{13a}$ includes an alkyl group having 10 or fewer carbon atoms, while the additive has a melting point of 91° C. or lower at normal pressure.

[23] The additive according to [16], wherein in the monovalent sulfur-containing group represented by Formula (i-2), n and p are each 0, and $R^{13a}$ includes an alkyl group having 4 to 10 carbon atoms, while the additive has a melting point of 91° C. or lower at normal pressure.

[24] The additive according to [16], wherein in the monovalent sulfur-containing group represented by Formula (i-2), n and p are each 0, and $R^{13a}$ includes an alkyl group having 6 to 10 carbon atoms, while the additive has a melting point of below 70° C. at normal pressure.

[25] The additive according to [16], wherein in the monovalent sulfur-containing group represented by Formula (i-2), n and p are each 0, and $R^{13a}$ includes an alkyl group having 6 to 10 carbon atoms, while the additive has a melting point of 35° C. or lower at normal pressure.

[26] The additive according to any one of [17] to [25], wherein the substituents for $R^{1a}$ to $R^{5a}$ are each selected from a methyl group, a t-butyl group, and a hydroxyl group, and there is one or fewer t-butyl group.

[27] The additive according to any one of [16] to [26], wherein a light absorption peak in a 100 μM chloroform solution of the additive is observed at 350 to 390 nm, and the absolute value of the slope of a straight line connecting this absorption peak with a peak end of the absorption spectrum on the longer wavelength side is 0.025 or larger.

[28] The additive according to [27], wherein the additive has a monovalent sulfur-containing group represented by Formula (i-2), at the position of either $R^{7a}$ or $R^{8a}$.

[29] The additive according to [16], wherein the substituents for $R^{1a}$ to $R^{5a}$ are each selected from a methyl group, a t-butyl group, and a hydroxyl group, and there is one or fewer t-butyl group.

[30] The additive according to [28], wherein the substituents for $R^{1a}$ to $R^{5a}$ are each selected from a methyl group, a t-butyl group, and a hydroxyl group, and there is one or fewer t-butyl group.

[31] An additive for imparting ultraviolet absorbency and/or a high refractive index to a matrix, the additive being represented by the following Formula (II):

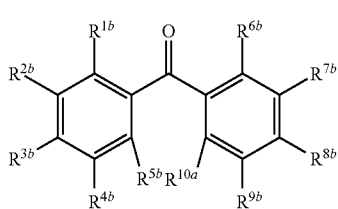

(II)

wherein $R^{1b}$ to $R^{10b}$ each independently represent a monovalent group selected from a monovalent sulfur-containing group represented by the following Formula (ii-1) or Formula (ii-2), a hydrogen atom, a monovalent hydrocarbon group having 1 to 10 carbon atoms, an aromatic group, an unsaturated group, a sulfur-containing group, an oxygen-containing group, a phosphorus-containing group, an alicyclic group, and a halogen atom:

 (ii-1)

 (ii-2)

wherein in Formula (ii-1), $R^{11b}$ represents a divalent hydrocarbon group having 1 to 12 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; and q represents an integer of 0 or 1, and in Formula (ii-2), $R^{12b}$ represents a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{13b}$ represents, or if s is 2 or larger, $R^{13b}$'s each independently represent, a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{14b}$ represents a monovalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; the total number of carbon atoms of $R^{12b}$, s units of $R^{13b}$ and $R^{14b}$ is 25 or less; r represents an integer of 0 or 1; and s represents an integer from 0 to 3, with the proviso that at least one of $R^{1b}$ to $R^{10b}$ is a monovalent sulfur-containing group represented by Formula (ii-1) or Formula (ii-2).

[32] The additive according to [31], wherein the matrix is a transparent resin.

[33] The additive according to [31] or [32], wherein the monovalent sulfur-containing group is a group represented by Formula (ii-1), and in this monovalent sulfur-containing group represented by Formula (ii-1), q is 0, or q is 1, with $R^{11b}$ including an alkylene group having 10 or fewer carbon atoms.

[34] The additive according to [31] or [32], wherein the monovalent sulfur-containing group is a group represented by Formula (ii-1), and in this monovalent sulfur-containing group represented by Formula (ii-1), q is 0, or q is 1, with $R^{11b}$ including an alkylene group having 9 or fewer carbon atoms, while the additive has a melting point of 91° C. or lower at normal pressure.

[35] The additive according to [31] or [32], wherein the monovalent sulfur-containing group is a group represented by Formula (ii-1), and in this monovalent sulfur-containing group represented by Formula (ii-1), q is 0, or q is 1, with $R^{11b}$ including an alkylene group having 8 or fewer carbon atoms, while the additive has a melting point of below 70° C. at normal pressure.

[36] The additive according to [31] or [32], wherein the monovalent sulfur-containing group is a group represented by Formula (ii-1), and in this monovalent sulfur-containing group represented by Formula (ii-1), q is 0, or q is 1, with $R^{11b}$ including an alkylene group having 8 or fewer carbon atoms, while the additive has a melting point of 35° C. or lower at normal pressure.

[37] The additive according to [31] or [32], wherein the monovalent sulfur-containing group is a group represented by Formula (ii-1), and in this monovalent sulfur-containing group represented by Formula (ii-1), q is 0, or q is 1, with $R^{11b}$ being an oxyalkylene group having 10 or fewer carbon atoms and having an ether bond at the proximal terminal.

[38] The additive according to [31] or [32], wherein the monovalent sulfur-containing group is a group represented by Formula (ii-2), and in this monovalent sulfur-containing group represented by Formula (ii-2), $R^{12b}$ and s units of $R^{13b}$ each includes an alkylene group having 18 or fewer carbon atoms, while $R^{14b}$ includes an alkyl group having 18 or fewer carbon atoms.

[39] The additive according to [31] or [32], wherein the monovalent sulfur-containing group is a group represented by Formula (ii-2), and in this monovalent sulfur-containing group represented by Formula (ii-2), $R^{12b}$ and s units of $R^{13b}$ each includes an alkylene group having 18 or fewer carbon atoms, and $R^{14b}$ includes an alkyl group having 18 or fewer carbon atoms, while the additive has a melting point of 91° C. or lower at normal pressure.

[40] The additive according to [31] or [32], wherein the monovalent sulfur-containing group is a group represented by Formula (ii-2), and in this monovalent sulfur-containing group represented by Formula (ii-2), $R^{12b}$ and s units of $R^{13b}$ each includes an alkylene group having 12 or fewer carbon atoms, and $R^{14b}$ includes an alkyl group having 12 or fewer carbon atoms, while the additive has a melting point of 91° C. or lower at normal pressure.

[41] The additive according to [31] or [32], wherein the monovalent sulfur-containing group is a group represented by Formula (ii-2), and in this monovalent sulfur-containing group represented by Formula (ii-2), $R^{12b}$ and s units of $R^{13b}$ each includes an alkylene group having 10 or fewer carbon atoms, and $R^{14b}$ includes an alkyl group having 10 or fewer carbon atoms, while the additive has a melting point of 91° C. or lower at normal pressure.

[42] The additive according to [31] or [32], wherein the monovalent sulfur-containing group is a group represented by Formula (ii-2), and in this monovalent sulfur-containing group represented by Formula (ii-2), $R^{12b}$ and s units of $R^{13b}$ each includes an alkylene group having 10 or fewer carbon atoms, and $R^{14b}$ includes an alkyl group having 10 or fewer carbon atoms, while the additive has a melting point of below 70° C. at normal pressure.

[43] The additive according to [31] or [32], wherein the monovalent sulfur-containing group is a group represented by Formula (ii-2), and in this monovalent sulfur-containing group represented by Formula (ii-2), $R^{12b}$ and s units of $R^{13b}$ each includes an alkylene group having 8 or fewer carbon atoms, and $R^{14b}$ includes an alkyl group having 8 or fewer carbon atoms, while the additive has a melting point of below 70° C. at normal pressure.

[44] The additive according to [31] or [32], wherein the monovalent sulfur-containing group is a group represented by Formula (ii-2), and in this monovalent sulfur-containing group represented by Formula (ii-2), $R^{12b}$ and s units of $R^{13b}$ each includes an alkylene group having 8 or fewer carbon atoms, and $R^{14b}$ includes an alkyl group having 8 or fewer carbon atoms, while the additive has a melting point of 35° C. or lower at normal pressure.

[45] An additive for imparting ultraviolet absorbency and/or a high refractive index to a matrix, the additive being represented by the following Formula (III):

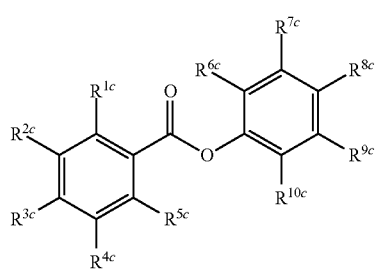

(III)

wherein $R^{1c}$ to $R^{10c}$ each independently represent a monovalent group selected from a monovalent sulfur-containing group represented by the following Formula (iii-1) or Formula (iii-2), a hydrogen atom, a monovalent hydrocarbon group having 1 to 10 carbon atoms, an aromatic group, an unsaturated group, a sulfur-containing group, an oxygen-containing group, a phosphorus-containing group, an alicyclic group, and a halogen atom:

$$-(R^{11c})_t-SH \qquad \text{(iii-1)}$$

$$-(R^{12c})_u-S-(R^{13c}-S)_v-R^{14c} \qquad \text{(iii-2)}$$

wherein in Formula (iii-1), $R^{11c}$ represents a divalent hydrocarbon group having 1 to 12 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; and t represents an integer of 0 or 1, and in Formula (iii-2), $R^{12c}$ represents a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{13c}$ represents, or if v is 2 or larger, $R^{13c}$'s each independently represent, a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{14c}$ represents a monovalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; the total number of carbon atoms of $R^{12c}$, v units of $R^{13c}$ and $R^{14c}$ is 25 or less; u represents an integer of 0 or 1; and v represents an integer from 0 to 3, with the proviso that at least one of $R^{1c}$ to $R^{10c}$ is a monovalent sulfur-containing group represented by Formula (iii-1) or Formula (iii-2).

[46] The additive according to [45], wherein the matrix is a transparent resin.

[47] The additive according to [43] or [44], wherein the monovalent sulfur-containing group is a group represented by Formula (iii-1), and in this monovalent sulfur-containing group represented by Formula (iii-1), t is 0, or t is 1, with $R^{11c}$ including an alkylene group having 10 or fewer carbon atoms.

[48] The additive according to [45] or [46], wherein the monovalent sulfur-containing group is a group represented by Formula (iii-1), and in this monovalent sulfur-containing group represented by Formula (iii-1), t is 0, or t is 1, with $R^{11c}$ including an alkylene group having 9 or fewer carbon atoms, while the additive has a melting point of 91° C. or lower at normal pressure.

[49] The additive according to [45] or [46], wherein the monovalent sulfur-containing group is a group represented by Formula (iii-1), and in this monovalent sulfur-containing group represented by Formula (iii-1), t is 0, or t is 1, with $R^{11c}$ including an alkylene group having 8 or fewer carbon atoms, while the additive has a melting point of below 70° C. at normal pressure.

[50] The additive according to [45] or [46], wherein the monovalent sulfur-containing group is a group represented by Formula (iii-1), and in this monovalent sulfur-containing group represented by Formula (iii-1), t is 0, or t is 1, with $R^{11c}$ including an alkylene group having 8 or fewer carbon atoms, while the additive has a melting point of 35° C. or lower at normal pressure.

[51] The additive according to [45] or [46], wherein the monovalent sulfur-containing group is a group represented by Formula (iii-1), and in this monovalent sulfur-containing group represented by Formula (iii-1), t is 0, or t is 1, with $R^{11c}$ being an oxyalkylene group having 10 or fewer carbon atoms and having an ether bond at the proximal terminal.

[52] The additive according to [45] or [46], wherein the monovalent sulfur-containing group is a group represented by Formula (iii-2), and in this monovalent sulfur-containing group represented by Formula (iii-2), $R^{12c}$ and v units of $R^{13c}$ each includes an alkylene group having 18 or fewer carbon atoms, while $R^{14c}$ includes an alkyl group having 18 or fewer carbon atoms.

[53] The additive according to [45] or [46], wherein the monovalent sulfur-containing group is a group represented by Formula (iii-2), and in this monovalent sulfur-containing group represented by Formula (iii-2), $R^{12c}$ and v units of $R^{13c}$ each includes an alkylene group having 18 or fewer carbon atoms, and $R^{14c}$ includes an alkyl group having 18 or fewer carbon atoms, while the additive has a melting point of 91° C. or lower at normal pressure.

[54] The additive according to [45] or [46], wherein the monovalent sulfur-containing group is a group represented by Formula (iii-2), and in this monovalent sulfur-containing group represented by Formula (iii-2), $R^{12c}$ and v units of $R^{13c}$ each includes an alkylene group having 12 or fewer carbon atoms, and $R^{14c}$ includes an alkyl group having 12 or fewer carbon atoms, while the additive has a melting point of 91° C. or lower at normal pressure.

[55] The additive according to [45] or [46], wherein the monovalent sulfur-containing group is a group represented by Formula (iii-2), and in this monovalent sulfur-containing group represented by Formula (iii-2), $R^{12c}$ and v units of $R^{13c}$ each includes an alkylene group having 10 or fewer carbon atoms, and $R^{14c}$ includes an alkyl group having 10 or fewer carbon atoms, while the additive has a melting point of 91° C. or lower at normal pressure.

[56] The additive according to [45] or [46], wherein the monovalent sulfur-containing group is a group represented by Formula (iii-2), and in this monovalent sulfur-containing group represented by Formula (iii-2), $R^{12c}$ and v units of $R^{13c}$ each includes an alkylene group having 10 or fewer carbon atoms, and $R^{14c}$ includes an alkyl group having 10 or fewer carbon atoms, while the additive has a melting point of below 70° C. at normal pressure.

[57] The additive according to [45] or [46], wherein the monovalent sulfur-containing group is a group represented by Formula (iii-2), and in this monovalent sulfur-containing group represented by Formula (iii-2), $R^{12c}$ and v units of $R^{13c}$ each includes an alkylene group having 8 or fewer carbon atoms, and $R^{14c}$ includes an alkyl group having 8 or fewer carbon atoms, while the additive has a melting point of below 70° C. at normal pressure.

[58] The additive according to [45] or [46], wherein the monovalent sulfur-containing group is a group represented by Formula (iii-2), and in this monovalent sulfur-containing group represented by Formula (iii-2), $R^{12c}$ and v units of $R^{13c}$ each includes an alkylene group having 8 or fewer carbon atoms, and $R^{14c}$ includes an alkyl group having 8 or fewer carbon atoms, while the additive has a melting point of 35° C. or lower at normal pressure.

[59] An additive for imparting ultraviolet absorbency and/or a high refractive index to a matrix, the additive being represented by the following Formula (IV):

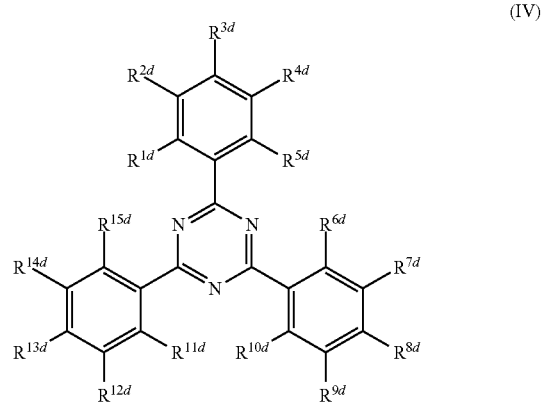

(IV)

wherein $R^{1d}$ to $R^{15d}$ each independently represent a monovalent group selected from a monovalent sulfur-containing group represented by the following Formula (iv-1) or Formula (iv-2), a hydrogen atom, a monovalent hydrocarbon group having 1 to 10 carbon atoms, an aromatic group, an unsaturated group, a sulfur-containing group, an oxygen-containing group, a phosphorus-containing group, an alicyclic group, and a halogen atom:

  (iv-1)

  (ii-2)

wherein in Formula (iv-1), $R^{16d}$ represents a divalent hydrocarbon group having 1 to 12 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; and w represents an integer of 0 or 1, and in Formula (iv-2), $R^{17d}$ represents a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{18d}$ represents, or if y is 2 or larger, $R^{18d}$'s each independently represent, a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{19d}$ represents a monovalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; the total number of carbon atoms of $R^{17d}$, y units of $R^{18d}$ and $R^{19d}$ is 25 or less; x represents an integer of 0 or 1; and y represents an integer from 0 to 3, with the proviso that at least one of $R^{1d}$ to $R^{15d}$ is a monovalent sulfur-containing group represented by Formula (iv-1) or Formula (iv-2).

[60] The additive according to [59], wherein the matrix is a transparent resin.

[61] The additive according to [59] or [60], wherein the monovalent sulfur-containing group is a group represented by Formula (iv-1) or Formula (iv-2), and in this monovalent sulfur-containing group represented by Formula (iv-1), w is 0, or w is 1, with $R^{16d}$ including an alkylene group having 8 or fewer carbon atoms, while in the monovalent sulfur-containing group represented by Formula (iv-2), $R^{17d}$ and y units of $R^{18d}$ each includes an alkylene group having 8 or fewer carbon atoms, with $R^{19d}$ including an alkyl group having 8 or fewer carbon atoms.

[62] An additive for imparting ultraviolet absorbency and/or a high refractive index to a matrix, the additive being represented by the following Formula (V):

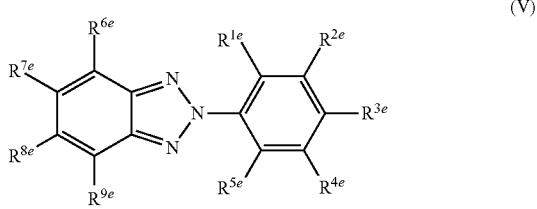

(V)

wherein $R^{1e}$ to $R^{9e}$ each independently represent a monovalent group selected from an alkyl group having 10 to 24 carbon atoms and having a straight chain having 10 to 20 carbon atoms, with the straight chain optionally being substituted with two or fewer alkyl groups each having 1 or 2 carbon atoms, a hydrogen atom, a monovalent hydrocarbon group having 1 to 4 carbon atoms, an aromatic group, an unsaturated group, an oxygen-containing group, a phosphorus-containing group, an alicyclic group, and a halogen atom; and at least one of $R^{1e}$ to $R^{9e}$ is the alkyl group having 10 to 24 carbon atoms.

[63] The additive according to [62], wherein the matrix is a transparent resin.

[64] The additive of the present invention is such that in regard to the additive according to any one of [1] to [64], a reactive functional group is bonded to at least any one group selected from $R^{1a}$ to $R^{13a}$, $R^{1b}$ to $R^{14b}$, $R^{1c}$ to $R^{14c}$, and $R^{1d}$ to $R^{19d}$ of Formulae (I) to (IV).

[65] The resin member of the present invention includes the additive according to any one of [1] to [15] and [31] to [64] in the resin of the matrix.

[66] The transparent resin member of the present invention includes the additive according to any one of [1] to [15] and [31] to [64] in the resin of the matrix.

[67] The resin member of the present invention includes the additive according to any one of [16] to [30] in the resin of the matrix.

[68] The transparent resin member of the present invention includes the additive according to any one of [16] to [30] in the resin of the matrix.

[69] The resin member of the present invention is such that the resin member according to any one of [65] to [68] is one layer in a member having a laminated multilayer structure, a film, a sheet, a plate-like member, or an optical resin.

Advantageous Effects of Invention

When the additive of the present invention is used, the additive has satisfactory compatibility with the resin as a matrix, has excellent heat resistance, and can maintain high transparency even if added in low concentrations to high concentrations. Accordingly, the performance of imparting ultraviolet absorbency or a high refractive index can be sufficiently manifested through addition in high concentrations, while transparency is maintained.

Furthermore, when the additive of the present invention is used, the function of imparting both ultraviolet absorbency and a high refractive index can be manifested by means of a single kind of additive.

A resin member containing the additive of the present invention exhibits transparency even under the conditions in which the concentration of the additive widely ranges from low concentrations to high concentrations, due to the heat resistance and compatibility with resins of the additive, and the resin member is imparted with a high refractive index and/or ultraviolet absorbency. Particularly, under the conditions of high concentrations, transparency is maintained, and a higher refractive index and/or higher ultraviolet absorbency can be imparted. Furthermore, a laminated multilayer structure is simplified, and reduction in the number of production processes and production cost is enabled. Furthermore, the resin member can be applied to higher resin molding processing temperatures.

BRIEF DESCRIPTION OF DRAWINGS

FIG. 1 shows ultraviolet-visible light absorption spectra (UV charts) of Examples 36 to 40 (benzotriazole-based).

FIG. 2 shows ultraviolet-visible light absorption spectra (UV charts) of Examples 41 to 44 and Comparative Example 9 (benzotriazole-based).

FIG. 3 shows ultraviolet-visible light absorption spectra (UV charts) of Examples 45 to 49 (benzotriazole-based).

FIG. 4 shows ultraviolet-visible light absorption spectra (UV charts) of Examples 50 to 54 (benzotriazole-based).

FIGS. 5a and 5b show ultraviolet-visible light absorption spectra (UV charts) of Examples 55 to 60 and Comparative Example 10 (benzotriazole-based).

FIG. 6 shows ultraviolet-visible light absorption spectra (UV charts) of Examples 61 to 64 and Comparative Example 11 (benzophenone-based).

FIG. 7 shows ultraviolet-visible light absorption spectra (UV charts) of Examples 65 and 66 and Comparative Example 12 (salicylate-based).

FIG. 8 shows ultraviolet-visible light absorption spectra (UV charts) of Examples 67 to 70 and Comparative Example 13 (triazine-based).

FIG. 17 shows photographs of films of Example 10 and Example 13.

DESCRIPTION OF EMBODIMENTS

Figure 9:
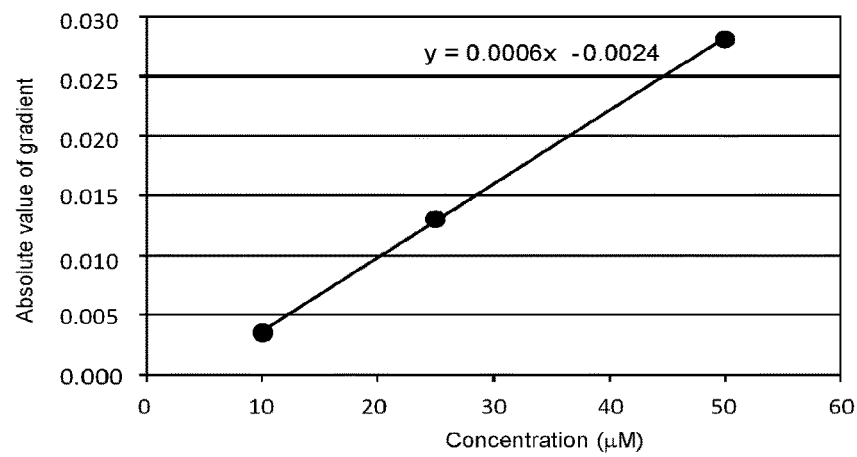
FIG. 9 is a graph obtained by measuring the absorption peaks of Compound 21 at the concentrations of 10, 25 and 50 µM, and plotting the absolute value of the slope on the longer wavelength side of the absorption peak in the wavelength region of 350 to 390 nm against the concentration of the ultraviolet absorber.
Figure 10:
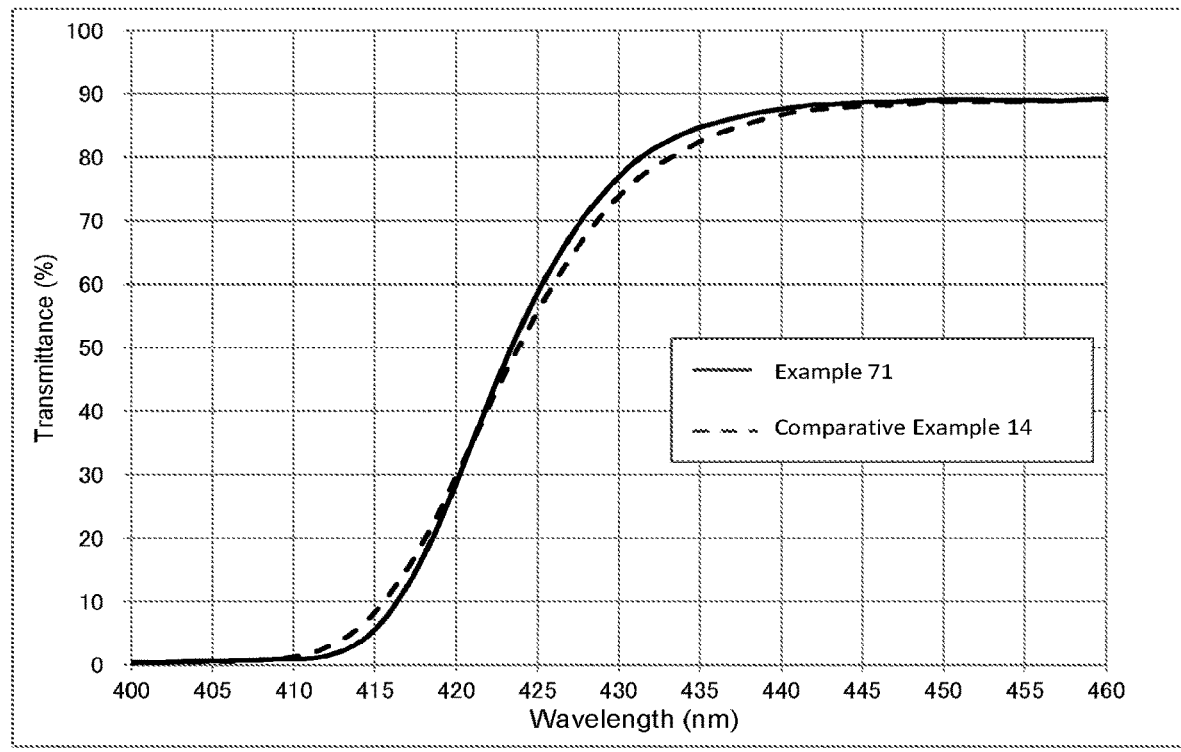
FIG. 10 shows transmission spectra of plastic lenses of Example 71 and Comparative Example 14.
Figure 11:
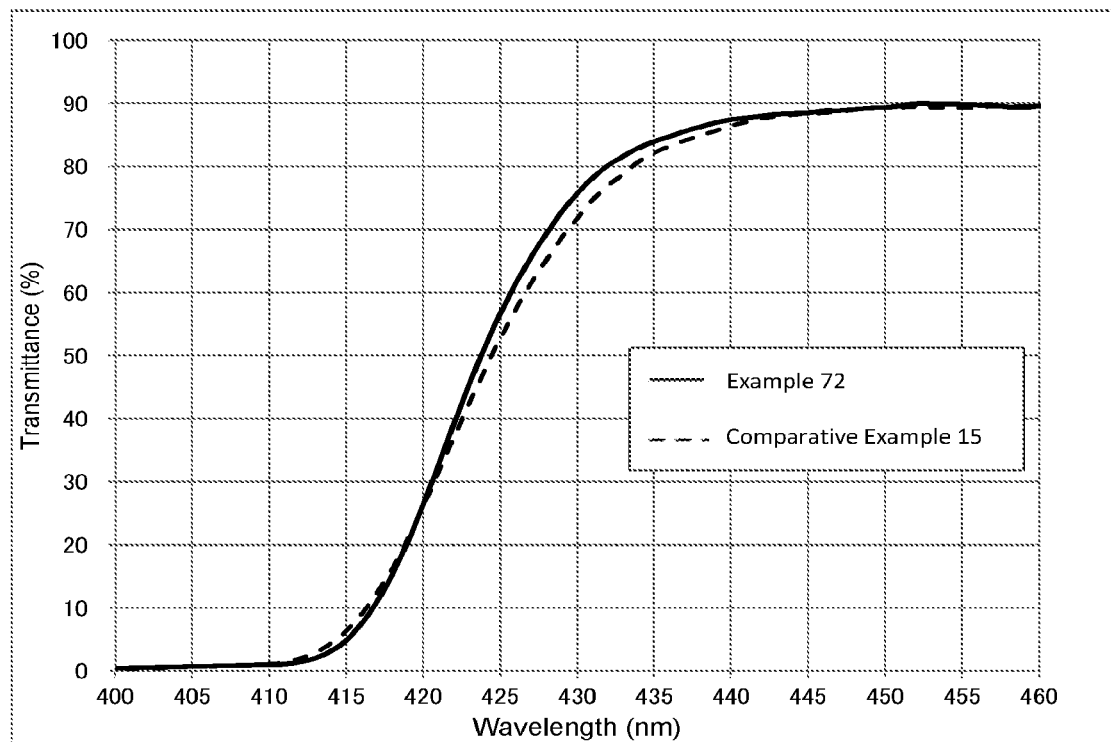
FIG. 11 shows transmission spectra of plastic lenses of Example 72 and Comparative Example 15.
Figure 12:
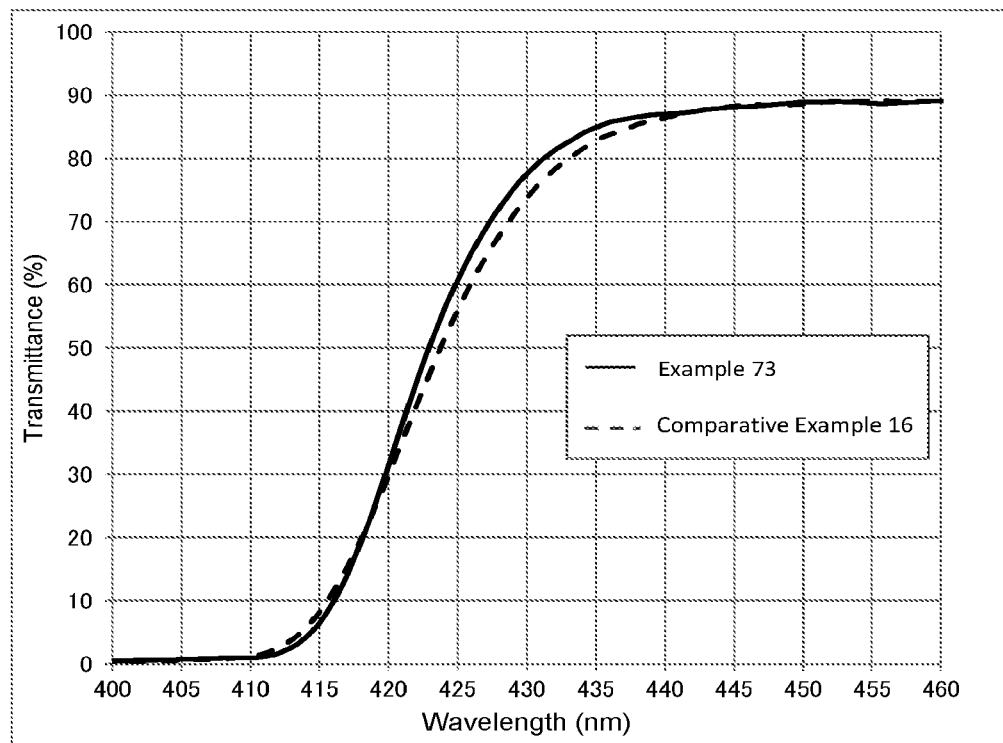
FIG. 12 shows transmission spectra of plastic lenses of Example 73 and Comparative Example 16.
Figure 13:
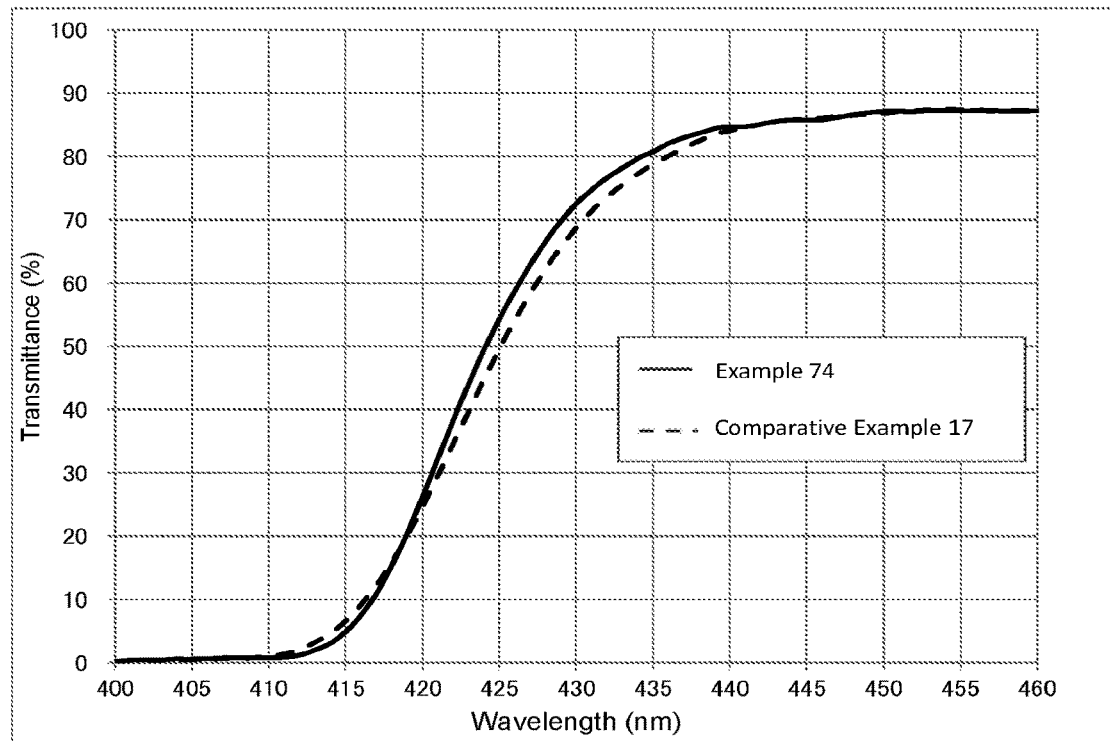
FIG. 13 shows transmission spectra of plastic lenses of Example 74 and Comparative Example 17.
Figure 14:
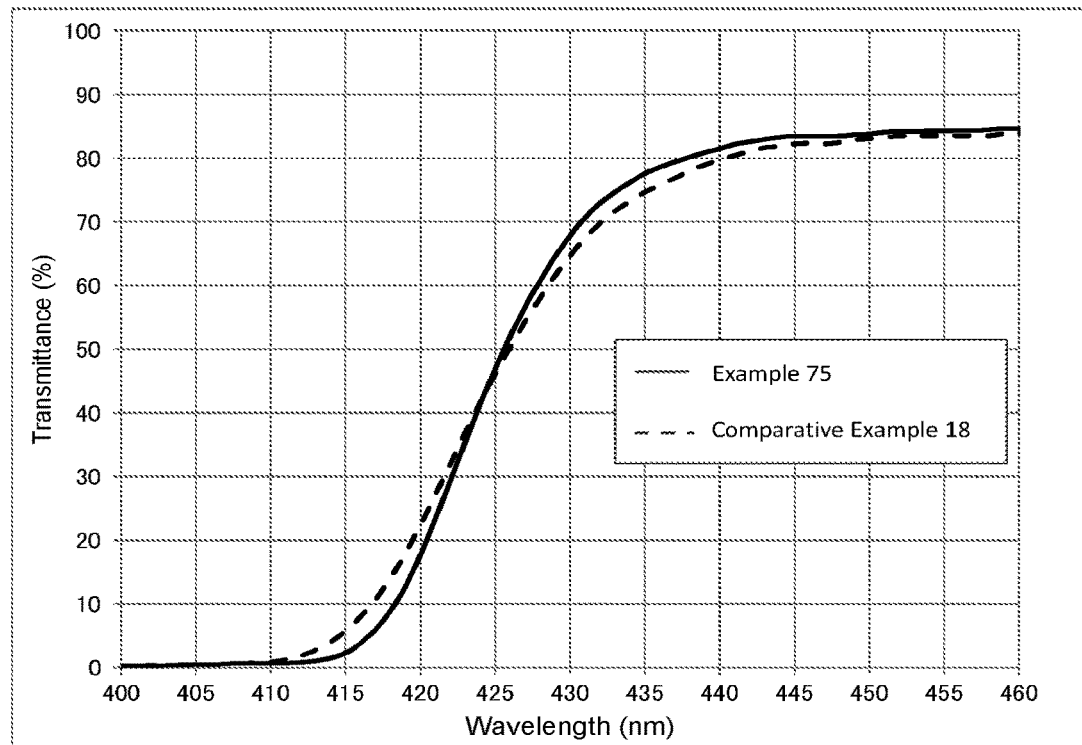
FIG. 14 shows transmission spectra of plastic lenses of Example 75 and Comparative Example 18.
Figure 15:
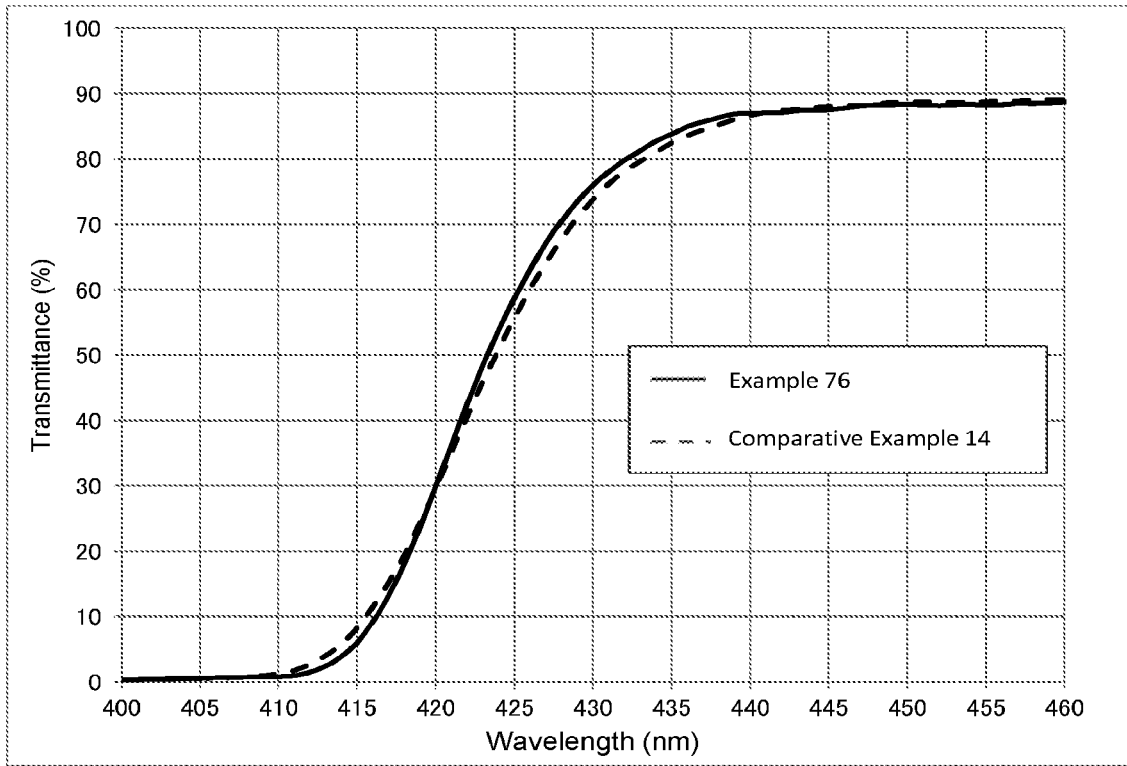
FIG. 15 shows transmission spectra of plastic lenses of Example 76 and Comparative Example 14.
Figure 16:
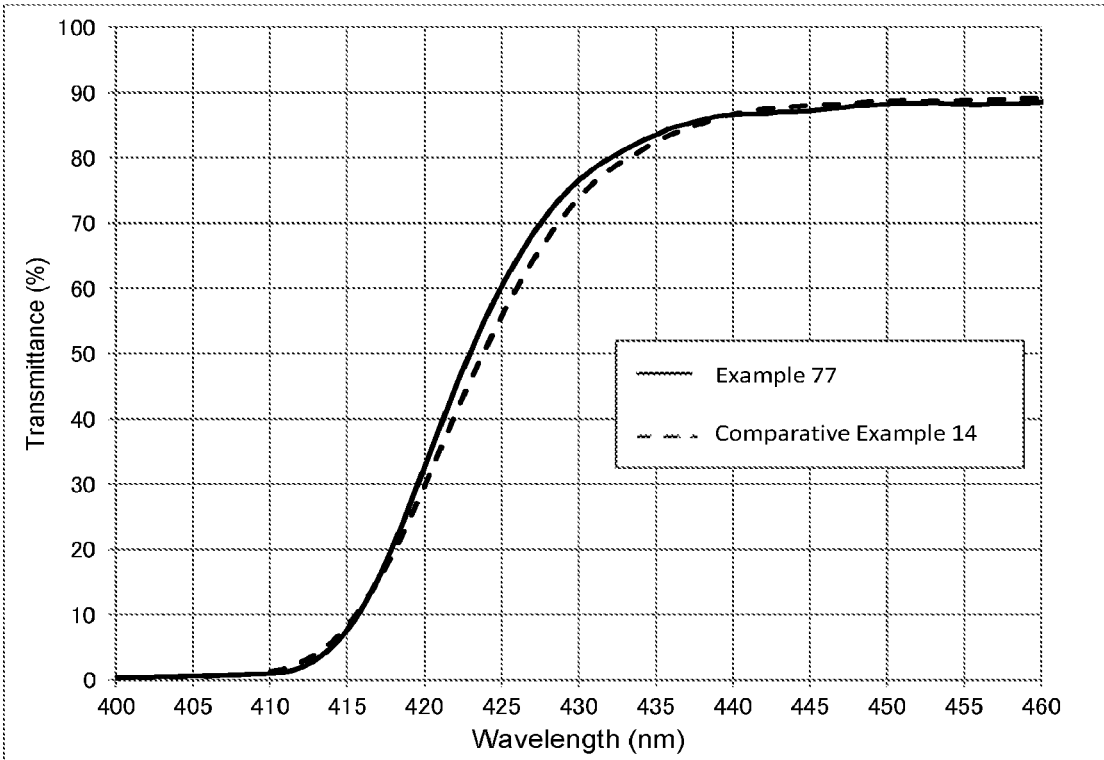
FIG. 16 shows transmission spectra of plastic lenses of Example 77 and Comparative Example 14.

Hereinafter, the present invention will be explained in detail.

The additives represented by Formula (I) to Formula (IV) described above have a feature that sulfur-containing groups have been introduced into benzotriazole-based, benzophenone-based, salicylate-based, and triazine-based ultraviolet-absorbing skeletons. Owing to this introduction of sulfur-containing groups, compatibility with a resin serving as a matrix is improved, and high transparency can be maintained even if added in high concentrations. Furthermore, the weight reduction temperature increases, and heat resistance is also enhanced. In addition, the additives exhibit ultraviolet absorbency due to the ultraviolet-absorbing skeletons, and may also exhibit performance as high refractive index-imparting agents depending on the sulfur-containing group.

[Substituents]

According to the present invention, examples of the "monovalent or divalent group selected from an aromatic group, an unsaturated group, a sulfur-containing group, an oxygen-containing group, a phosphorus-containing group, an alicyclic group, and a halogen atom" include a group capable of imparting a high refractive index, a group capable of adjusting heat resistance and compatibility with a resin, and a group capable of reacting with a resin and/or a monomer of a resin. For example, the following groups are included.

(Aromatic Group)

An aromatic group contains an aromatic ring such as a benzene ring, a naphthalene ring, or an anthracene ring, and the number of carbon atoms is preferably 6 to 18, and more preferably 6 to 14. Examples of a monovalent or divalent aromatic group include a phenyl group, a 2-methylphenyl group, a 3-methylphenyl group, a 4-methylphenyl group, a 2,4-dimethylphenyl group, a 2,5-dimethylphenyl group, a 3,4-dimethylphenyl group, a 3,5-dimethylphenyl group, a 2,4,5-trimethylphenyl group, a 2,4,6-trimethylphenyl group, a 4-biphenyl group, a 1-naphthyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-chlorophenyl group, a 2-fluorophenyl group, a 4-fluorophenyl group, a 2-trifluoromethylphenyl group, a 4-trifluoromethylphenyl group, a 1-naphthyl group, and a 2-naphthyl group.

(Unsaturated Group)

An unsaturated group contains a carbon-carbon or carbon-heteroatom unsaturated bond such as a carbon-carbon double bond, a carbon-carbon triple bond, a carbon-oxygen double bond (a carbonyl group, an aldehyde group, a carboxyl group, or the like), a carbon-nitrogen double bond (an isocyanate group or the like), or a carbon-nitrogen triple bond (a cyano group, a cyanate group or the like), and the number of carbon atoms is preferably 1 to 10, and more preferably 1 to 8. Examples of the monovalent or divalent unsaturated group include an acryloyl group, a methacryloyl group, a maleic acid monoester group, a styryl group, an allyl group, a vinyl group, an amide group, a carbamoyl group, a cyano group, and an isocyanate group.

(Sulfur-Containing Group)

A sulfur-containing group contains a thiol group, a sulfide group, a disulfide group, a sulfonyl group, a sulfo group, a thiocarbonyl group, a thiocarbamoyl group, or a thiourea group, and the number of carbon atoms is preferably 0 to 10. Examples of the monovalent or divalent sulfur-containing group include a thiomethoxy group, a thioethoxy group, a thio-n-propoxy group, a thioisopropoxy group, a thio-n-butoxy group, a thio-t-butoxy group, a thiophenoxy group, a p-methylthiophenoxy group, a p-methoxythiophenoxy group, a thiophene group, a thiazole group, a thiol group, a sulfo group, a sulfide group, a disulfide group, a sulfonyl group, a thiocarbonyl group, and a thiourea group.

(Oxygen-Containing Group)

In regard to the oxygen-containing group, in a case in which the oxygen-containing group contains an aromatic ring group or an alicyclic group, the number of carbon atoms is preferably 6 to 12; and in a case in which the oxygen-containing group does not contain an aromatic ring group or an alicyclic group, the number of carbon atoms is preferably 0 to 6. Examples of a monovalent or divalent oxygen-containing group include a hydroxyl group, a methoxy group, an ethoxy group, a propoxy group, a butoxy group, a phenoxy group, a methylphenoxy group, a dimethylphenoxy group, a naphthoxy group, a phenylmethoxy group, a phenylethoxy group, an acetoxy group, an acetyl group, an aldehyde group, a carboxyl group, a carbamoyl group, a urea group, an ether group, a carbonyl group, an ester group, an oxazole group, and a morpholine group.

(Phosphorus-Containing Group)

A phosphorus-containing group contains a phosphine group, a phosphite group, a phosphonic acid group, a phosphinic acid group, a phosphoric acid group, or a phosphoric acid ester group. In a case in which the phosphorus-containing group includes an aromatic ring group or an alicyclic group, the number of carbon atoms is preferably 6 to 22, and in a case in which the phosphorus-containing group does not include an aromatic ring group or an alicyclic group, the number of carbon atoms is preferably 0 to 6. Examples of a monovalent or divalent phosphorus-containing group include a trimethylphosphine group, a tributylphosphine group, a tricyclohexylphosphine group, a triphenylphosphine group, a tritolylphosphine group, a methylphosphite group, an ethylphosphite group, a phenylphosphite group, a phosphonic acid group, a phosphinic acid group, a phosphoric acid group, and a phosphoric acid ester group.

(Alicyclic Group)

In regard to an alicyclic group, the number of carbon atoms is preferably 3 to 10, and more preferably 3 to 8. Examples of a monovalent or divalent alicyclic group include a cyclopropyl group, a cyclobutyl group, a cyclopentyl group, a cyclohexyl group, a cycloheptyl group, and a cyclooctyl group.

(Halogen Atom)

Examples of the halogen atom include a fluorine atom, a chlorine atom, a bromine atom, and an iodine atom.

The additive represented by Formula (V) described above has a feature that a long-chain alkyl group has been introduced into a benzotriazole-based ultraviolet-absorbing skeleton. Owing to this introduction of a long-chain alkyl group, the additive becomes a liquid, acquires satisfactory compatibility with a resin serving as a matrix, and can maintain high transparency even if added in high concentrations. Therefore, a resin member having high transparency and also having high ultraviolet absorbency is obtained.

1. Additive Represented by Formula (I)

An additive represented by Formula (I) described above contains the above-described monovalent sulfur-containing group represented by Formula (i-1) or Formula (i-2) in a benzotriazole-based skeleton.

In Formula (i-1), $R^{10a}$ represents a divalent hydrocarbon group having 1 to 12 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{10a}$ include a linear or branched alkylene group, alkenylene group, and an alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group.

In a case in which the divalent hydrocarbon group is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group and halogen atom of the monovalent or divalent group include the groups listed as examples in the section [Substituents] described above.

In Formula (i-1), m represents an integer of 0 or 1.

In Formula (i-2), $R^{11a}$ represents a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{11a}$ include a linear or branched alkylene group, a linear or branched alkenylene group, and a linear or branched alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecan-1,13-yl group, a tetradecan-1,14-yl group, a pentadecan-1,15-yl group, a hexadecan-1,16-yl group, a heptadecan-1,17-yl group, an octadecan-1,18-yl group, a nonadecan-1,19-yl group, and an eicosan-1,20-yl group. Among these, an alkylene group is preferred, and a linear alkylene group is more preferred.

In a case in which the divalent hydrocarbon group of $R^{11a}$ is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group phosphorus-containing group, alicyclic group and halogen atom of the monovalent or divalent group include the groups listed as examples in the section [Substituents] described above.

In Formula (i-2), in a case in which p is 2 or larger, $R^{12a}$'s each independently represent a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{12a}$ include the divalent hydrocarbon groups listed above as examples of the divalent hydrocarbon groups of $R^{11a}$. Among these, an alkylene group is preferred, and a linear alkylene group is more preferred.

In a case in which the divalent hydrocarbon group of $R^{12a}$ is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In Formula (i-2), $R^{13a}$ represents a hydrogen atom, or represents a group represented by —$(R^{14a})_l$—$R^{15a}$ (wherein $R^{14a}$ represents a divalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom; $R^{15a}$ represents a hydrogen atom, or represents a substituent containing any one skeleton selected from benzotriazole, benzophenone, a benzoic acid ester, and triazine; and l represents an integer of 0 or 1).

Examples of the divalent hydrocarbon group of $R^{14a}$ include the divalent hydrocarbon groups listed above as examples of the divalent hydrocarbon groups of $R^{10a}$. Among these, an alkylene group is preferred, and a linear alkylene group is more preferred.

In a case in which the divalent group of $R^{14a}$ is substituted a hydrogen atom with, interrupted a proximal terminal by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group and halogen atom of the monovalent or divalent group include the groups listed as examples in the section [Substituents] described above.

In a case in which $R^{15a}$ is a substituent containing any one skeleton selected from benzotriazole, benzophenone, a benzoic acid ester and triazine, an example of the substituent containing benzotriazole may be a group represented by the following Formula (A), and an example of the substituent containing benzophenone may be a group represented by the following Formula (B). An example of the substituent containing a benzoic acid ester may be a group represented by the following Formula (C), and an example of the substituent containing triazine may be a group represented by the following Formula (D).

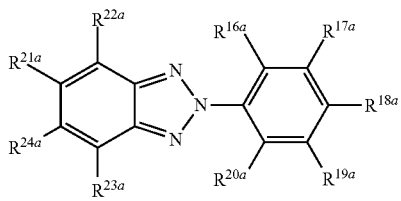

(A)

In Formula (A), any one among $R^{16a}$ to $R^{24a}$ represents a monovalent bonding moiety that is bonded to $R^{14a}$ or a terminal sulfur atom of Formula (i-2); and the others of $R^{16a}$ to $R^{24a}$ each independently represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group and a halogen atom.

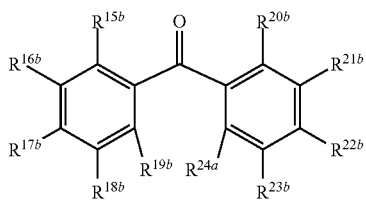

(B)

In Formula (B), any one among $R^{15b}$ to $R^{24b}$ represents a monovalent bonding moiety that is bonded to $R^{14a}$ or a terminal sulfur atom of Formula (i-2); and the others of $R^{15b}$ to $R^{24b}$ each independently represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group and a halogen atom.

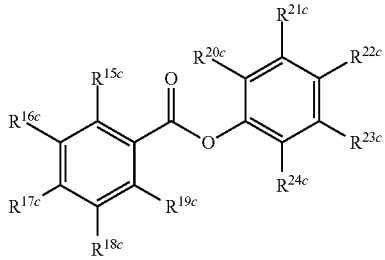

(C)

In Formula (C), any one among $R^{15c}$ to $R^{24c}$ represents a monovalent bonding moiety that is bonded to $R^{14a}$ or a terminal sulfur atom of Formula (i-2); and the others of $R^{15c}$ to $R^{24c}$ each independently represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group, and a halogen atom.

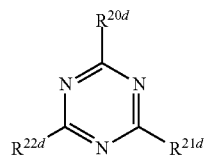

(D)

In Formula (D), $R^{20d}$ to $R^{22d}$ each represents any one of the following [a] and [b].

[a] At least one of $R^{20d}$ to $R^{22d}$ represents a monovalent bonding moiety that is bonded to $R^{14a}$ or a terminal sulfur atom of Formula (i-2), and the others of $R^{20d}$ to $R^{22d}$ each independently represent a hydrogen atom, a hydrocarbon group having 1 to 10 carbon atoms, an aromatic group, an unsaturated group, a sulfur-containing group, an oxygen-containing group, a phosphorus-containing group, an alicyclic group, a halogen atom, and a group represented by the following Formula (d):

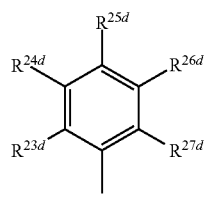

(d)

wherein $R^{23d}$ to $R^{27d}$ each independently represent a monovalent group selected from a hydrogen atom, a hydrocarbon group of 1 to 10 carbon atoms, an aromatic group, an unsaturated group, a sulfur-containing group, an oxygen-containing group, a phosphorus-containing group, an alicyclic group, and a halogen atom. That is, 1 to 3 units of the group represented by Formula (I) may be bonded to the triazine ring.

[b] At least one of $R^{20d}$ to $R^{22d}$ represents a group represented by the following Formula (d'):

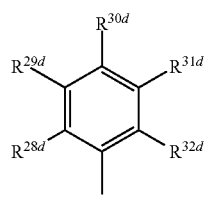

(d')

wherein at least one of $R^{28d}$ to $R^{32d}$ represents a monovalent bonding moiety that is bonded to $R^{14a}$ or a terminal sulfur atom of Formula (i-2); and the others of $R^{28d}$ to $R^{32d}$ each independently represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group, and a halogen atom, and the others of $R^{20d}$ to $R^{22d}$ each independently represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group, and a halogen atom. That is, 1 to 5 units of the group represented by Formula (I) may be bonded to the benzene ring represented by Formula (d').

In regard to Formulae (A) to (D) and (d), in a case in which $R^{16a}$ to $R^{24a}$, $R^{15b}$ to $R^{24b}$, $R^{15c}$ to $R^{24c}$, and $R^{20d}$ to $R^{27d}$ are each a monovalent hydrocarbon group, examples of this monovalent hydrocarbon group include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, and a decan-1-yl group.

In a case in which $R^{16a}$ to $R^{24a}$, $R^{15b}$ to $R^{24b}$, $R^{15c}$ to $R^{24c}$, and $R^{20d}$ to $R^{27d}$ each represent a monovalent group selected from an aromatic group, an unsaturated group, a sulfur-containing group, an oxygen-containing group, a phosphorus-containing group, an alicyclic group, and a halogen atom, specific examples thereof include the groups listed as examples in the section [Substituents] described above.

In Formula (i-2), n represents an integer of 0 or 1, and p represents an integer from 0 to 3, and preferably an integer of 0 or 1.

In Formula (i-2), the total number of carbon atoms of $R^{11a}$, p units of $R^{12a}$, and $R^{13a}$ is 25 or less.

In regard to Formula (I), in a case in which $R^{1a}$ to $R^{9a}$ each represent a group other than the monovalent sulfur-containing group represented by Formula (i-1) or Formula (i-2), $R^{1a}$ to $R^{9a}$ each represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group, and a halogen atom.

In a case in which $R^{1a}$ to $R^{9a}$ are each a monovalent hydrocarbon group, examples of this monovalent hydrocarbon group include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, and a decan-1-yl group. Among these, a linear or branched alkyl group having 1 to 8 carbon atoms is preferred.

In a case in which $R^{1a}$ to $R^{9a}$ each represent a monovalent group selected from an aromatic group, an unsaturated group, a sulfur-containing group, an oxygen-containing group, a phosphorus-containing group, an alicyclic group, and a halogen atom, specific examples thereof include the groups listed as examples in the section [Substituents] described above.

In regard to Formula (I), at least one of $R^{1a}$ to $R^{9a}$ represents a monovalent sulfur-containing group represented by Formula (i-1) or Formula (i-2). Above all, when the ease or cost of actual synthesis and heat resistance are taken into consideration, or when it is taken into consideration that by making the compatibility with a resin serving as a matrix satisfactory, clouding of the resin member to which the additive of the present invention has been added can be suppressed, and manifestation of high ultraviolet absorbency or imparting of a high refractive index under addition of the additive in high concentrations is enabled, it is preferable that one or two of $R^{1a}$ to $R^{9a}$ are monovalent sulfur-containing groups represented by Formula (i-1) or Formula (i-2).

The position of the monovalent sulfur-containing group represented by Formula (i-1) or Formula (i-2) in Formula (I) is not particularly limited, and the position may be the position of $R^{1a}$, $R^{3a}$, $R^{5a}R^{7a}$ or $R^{8a}$.

In regard to the additive of Formula (I) into which (i-1) has been introduced as the monovalent sulfur-containing group, upon considering heat resistance and the characteristics of enabling manifestation of high ultraviolet absorbency or imparting of a high refractive index when the additive is added in low concentrations to high concentrations, it is preferable for the monovalent sulfur-containing group represented by Formula (i-1) that m is 0, or m is 1, with $R^{10a}$ including an alkylene group having 10 or fewer carbon atoms.

Furthermore, these additives have a tendency that melting points are lowered when sulfur-containing groups are introduced into the additives and numbers of carbon atoms of each sulfur-containing groups are adjusted. When the melting point is lowered, particularly satisfactory compatibility with a resin serving as a matrix is obtained. From this point of view, it is preferable that in the monovalent sulfur-containing group represented by Formula (i-1), m is 0, or m is 1, with $R^{10a}$ including an alkylene group having 9 or fewer carbon atoms, and the additive has a melting point of 91° C. or lower at normal pressure (for example, standard atmospheric pressure: 101325 Pa).

According to another preferred embodiment, in the monovalent sulfur-containing group represented by Formula (i-1), m is 0, or m is 1, with $R^{10a}$ including an alkylene group having 8 or fewer carbon atoms, and the additive has a melting point of below 70° C. at normal pressure. Alternatively, in the monovalent sulfur-containing group represented by Formula (i-1), m is 0, or m is 1, with $R^{10a}$ including an alkylene group having 8 or fewer carbon atoms, and the additive has a melting point of 35° C. or lower at normal pressure. That is, when the number of carbon atoms is 8 or less, and the melting point is below 70° C., even if the additive is added in high concentrations, high transparency is obtained at large film thicknesses. Furthermore, if the additive is liquid at normal temperature (5° C. to 35° C.), high transparency can be realized even if the additive is added in high concentrations at larger film thicknesses.

In regard to the additive of Formula (I) into which (i-2) has been introduced as the monovalent sulfur-containing group, upon considering heat resistance and the characteristics of enabling manifestation of high ultraviolet absorbency or imparting of a high refractive index when the additive is added in low concentrations to high concentrations, it is preferable for the monovalent sulfur-containing group represented by Formula (i-2) that $R^{11a}$ and p units of $R^{12a}$ each includes an alkylene group having 18 or fewer carbon atoms, and $R^{13a}$ includes an alkyl group having 18 or fewer carbon atoms.

These additives have a tendency that when sulfur-containing groups which are adjusted respective numbers of carbon atoms from short chains to medium chains are introduced into the additives, melting points are lowered. When the melting point is lowered, particularly satisfactory compatibility with a resin serving as a matrix is obtained. When this is taken into consideration, it is preferable for the monovalent sulfur-containing group represented by Formula (i-2), $R^{11a}$ and p units of $R^{12a}$ each include an alkylene group having 18 or fewer carbon atoms, and $R^{13a}$ includes an alkyl group having 18 or fewer carbon atoms, while the additive has a melting point of 91° C. or lower at normal pressure.

In a case in which the additive has a monovalent sulfur-containing group represented by Formula (i-1) or Formula (i-2) at any one position of $R^{1a}$ to $R^{5a}$, according to a preferred embodiment, in the monovalent sulfur-containing group represented by Formula (i-1), m is 0, or m is 1, with $R^{10a}$ including an alkylene group having 8 or fewer carbon atoms, or in the monovalent sulfur-containing group represented by Formula (i-2), $R^{11a}$ and p units of $R^{12a}$ each includes an alkylene group having 8 or fewer carbon atoms, and $R^{13a}$ includes an alkyl group having 8 or fewer carbon atoms, while the additive has a melting point of below 70° C. at normal pressure. According to a more preferred embodiment, in the monovalent sulfur-containing group represented by Formula (i-1), m is 0, or m is 1, with $R^{10a}$ including an alkylene group having 8 or fewer carbon atoms, or in the monovalent sulfur-containing group represented by Formula (i-2), $R^{11a}$ and p units of $R^{12a}$ each includes an alkylene group having 8 or fewer carbon atoms, and $R^{13a}$ includes an alkyl group having 8 or fewer carbon atoms, while the additive has a melting point of 35° C. or lower at normal pressure.

(Ultraviolet Absorber that has Excellent Heat Resistance and is Intended for Imparting Ultraviolet Absorbency and High Refractive Index while Maintaining Transparency of Transparent Resin Matrix)

Preferred embodiments of an ultraviolet absorber that has excellent heat resistance and is intended for imparting ultraviolet absorbency and a high refractive index while maintaining transparency of a transparent resin matrix, include the following.

The ultraviolet absorber has a monovalent sulfur-containing group represented by Formula (i-2) at any one of the positions of $R^{6a}$ to $R^{9a}$, and the monovalent sulfur-containing group represented by Formula (i-2) is represented by the following formula:

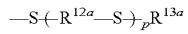

in which p units of $R^{12a}$ each includes an alkylene group having 1 to 18 carbon atoms, while $R^{13a}$ includes an alkyl group having 1 to 18 carbon atoms.

Furthermore, p units of $R^{12a}$ each includes an alkylene group having 1 to 8 carbon atoms, and $R^{13a}$ includes an alkyl group having 1 to 8 carbon atoms, while the melting point is below 70° C. at normal pressure.

$R^{13a}$ includes an alkyl group having 1 to 18 carbon atoms.

$R^{13a}$ includes an alkyl group having 1 to 18 carbon atoms, and the melting point is 91° C. or lower at normal pressure.

$R^{13a}$ includes an alkyl group having 1 to 12 carbon atoms, and the melting point is 91° C. or lower at normal pressure.

$R^{13a}$ includes an alkyl group having 1 to 10 carbon atoms, and the melting point is 91° C. or lower at normal pressure.

$R^{13a}$ includes an alkyl group having 4 to 10 carbon atoms, and the melting point is 91° C. or lower at normal pressure.

$R^{13a}$ includes an alkyl group having 6 to 10 carbon atoms, and the melting point is below 70° C. at normal pressure.

$R^{13a}$ includes an alkyl group having 6 to 10 carbon atoms, and the melting point is 35° C. or lower at normal pressure.

The substituent is selected from a methyl group, a t-butyl group, and a hydroxyl group, while there is one or fewer t-butyl group. Above all, the substituent is at any one of the positions of $R^{1a}$, $R^{2a}$ and $R^{4a}$, and particularly, the substituent of $R^{1a}$ is a hydroxyl group, the substituent of $R^{2a}$ is a t-butyl group, while the substituent of $R^{4a}$ is a methyl group.

(Ultraviolet Absorber that Absorbs Light in Long Wavelength Region and Suppresses Yellowing of Transparent Resin Matrix)

An ultraviolet absorber that absorbs light in the long wavelength region and suppresses yellowing of a transparent resin matrix according to a preferred embodiment has a monovalent sulfur-containing group represented by Formula (i-2) at any one of the positions of $R^{6a}$ to $R^{9a}$, and the monovalent sulfur-containing group represented by Formula (i-2) is represented by the following formula:

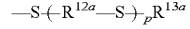

wherein $R^{12a}$, $R^{13a}$ and p respectively have the same meanings as described above.

The additive of Formula (I) has a high solubility in resin monomers, does not separate from the surface even if the resin matrix is processed into a plastic lens, and the plastic lens has high transparency, and due to its optical characteristics, the plastic lens can sufficiently absorb light in the wavelength region of up to 250 to 420 nm. Furthermore, the additive has a high ultraviolet absorption effect (molar extinction coefficient), and can sufficiently absorb light of the wavelengths even if added in a small amount. Since the slope of an absorption peak of the additive at 350 to 390 nm in a chloroform solution is larger than that of conventional ultraviolet absorbers, yellowing of the resin member can be suppressed.

Also, in order to obtain a resin member having excellent external appearance with suppressed yellowing, which absorbs harmful light in the wavelength region of up to 400 to 420 nm that has a potential of causing disorders in the eye tissues, such as age-related macular degeneration, and suppresses the absorption of light having a wavelength in the vicinity of 420 nm or larger that causes yellowing of a lens, it is preferable that the light absorption peak in a 100 μM chloroform solution is found at 350 to 390 nm, more preferably at 360 to 380 nm, and particularly preferably at 360 to 375 nm. Furthermore, it is preferable that an absorption peak in those wavelength regions is the maximum absorption wavelength ($\lambda_{max}$). Furthermore, regarding the wavelength peak, in order to suppress absorption of light having a longer wavelength than near 420 nm, it is desirable that the absorption spectrum on the longer wavelength side is sharp (the absolute value of the slope is large), and the slope on the longer wavelength side of the absorption peak (absolute value of the slope of a straight line connecting the absorption peak and the peak end of the absorption spectrum on the longer wavelength side; see FIG. 3 and Examples described below) is preferably 0.025 or larger, and more preferably 0.030 or larger. Furthermore, in order to efficiently absorb light with a small amount of the additive, the molar absorption coefficient (maximum molar absorption coefficient: $\varepsilon_{\lambda max}$) of the absorption peak at 350 to 390 nm is preferably 17,000 L/(mol·cm) or larger, more preferably 18,000 L/(mol·cm) or larger, and particularly preferably 20,000 L/(mol·cm) or larger.

2. Additive Represented by Formula (II)

An additive represented by Formula (II) described above contains the above-described monovalent sulfur-containing group represented by Formula (ii-1) or (ii-2) in a benzophenone-based skeleton.

In regard to Formula (ii-1), $R^{11b}$ represents a divalent hydrocarbon group having 1 to 12 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{11b}$ include a linear or branched alkylene group, an alkenylene group, and an alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group.

In a case in which the divalent hydrocarbon group is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group and halogen atom of the monovalent or divalent group include the groups listed as examples in the section [Substituents] described above.

In regard to Formula (ii-1), q represents an integer of 0 or 1.

In regard to Formula (ii-2), $R^{12b}$ represents a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{12b}$ include a linear or branched alkylene group, a linear or branched alkenylene group, and a linear or branched alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group an octane-1,8-diyl group, a nonane-1,9-diyl group, a decane-1,10-diyl group, an undecane-1,11-diyl group, a dodecane-1,12-diyl group, a tridecan-1,13-yl group, a tetradecan-1,14-yl group, a pentadecan-1,15-yl group, a hexadecan-1,16-yl group, a heptadecan-1,17-yl group, an octadecan-1,18-yl group, a nonadecan-1,19-yl group, and an eicosan-1,20-yl group. Among these, an alkylene group is preferred, and a linear alkylene group is more preferred.

In a case in which the divalent hydrocarbon group of $R^{12b}$ is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (ii-2), in a case in which s of $R^{13b}$ is 2 or larger, $R^{13b}$'s each independently represent a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{13b}$ include the groups listed above as examples of the divalent hydrocarbon groups of $R^{12b}$. Among these, an alkylene group is preferred, and a linear alkylene group is more preferred.

In a case in which the divalent hydrocarbon group of $R^{13b}$ which may be substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (ii-2), $R^{14b}$ represents a monovalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the monovalent hydrocarbon group of $R^{14b}$ include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, a decan-1-yl group, an undecan-1-yl group, a dodecan-1-yl group, a tridecan-1-yl group, a tetradecan-1-yl group, a pentadecan-1-yl group, a hexadecan-1-yl group, a heptadecan-1-yl group, an octadecan-1-yl group, a nonadecan-1-yl group, and an eicosan-1-yl group. Among these, an alkyl group is preferred, and a linear alkyl group is more preferred.

In a case in which the monovalent hydrocarbon group of $R^{14b}$ is substituted a hydrogen atom with, interrupted a proximal terminal by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (ii-2), r represents an integer of 0 or 1, and s represents an integer from 0 to 3, and preferably 0 or 1.

In regard to Formula (ii-2), the total number of carbon atoms of $R^{12b}$, S units of $R^{13b}$, and $R^{14b}$ is 25 or less.

In regard to Formula (II), in a case in which $R^{1b}$ to $R^{10b}$ each represent a group other than the monovalent sulfur-containing group represented by Formula (ii-1) or Formula (ii-2), $R^{1b}$ to $R^{10b}$ each represent a monovalent group selected from a hydrogen atom, a monovalent hydrocarbon group having 1 to 10 carbon atoms, an aromatic group, an unsaturated group, a sulfur-containing group, an oxygen-containing group, a phosphorus-containing group, an alicyclic group, and a halogen atom.

In a case in which $R^{1b}$ to $R^{10b}$ each represent a monovalent hydrocarbon group, examples of this monovalent hydrocarbon group include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methyl-propan-1-yl group, a 2-methylpropan-2-yl group, a pentan-1-yl group, a pentan-2-yl group, a hexan-1-yl group, a heptan-1-yl group, an octan-1-yl group, a nonan-1-yl group, and a decan-1-yl group. Among these, a linear or branched alkyl group having 1 to 8 carbon atoms is preferred.

In a case in which $R^{1b}$ to $R^{10b}$ each represent a monovalent group selected from an aromatic group, an unsaturated group, a sulfur-containing group, an oxygen-containing group, a phosphorus-containing group, an alicyclic group, and a halogen atom, specific examples thereof include the groups listed as examples in the section [Substituents] described above.

In regard to Formula (II), at least one of $R^{1b}$ to $R^{10b}$ represents a monovalent sulfur-containing group represented by Formula (ii-1) or Formula (ii-2). Above all, when the ease of actual synthesis, production cost and heat resistance are taken into consideration, or when it is considered that by improving the compatibility with a resin serving as a matrix, clouding of the resin member to which the additive of the present invention has been added can be suppressed, and manifestation of high ultraviolet absorbency or imparting of a high refractive index under addition of the additive in high concentrations is enabled, it is preferable that one or two of $R^{1b}$ to $R^{10b}$ are monovalent sulfur-containing groups represented by Formula (ii-1) or Formula (ii-2).

The position of the monovalent sulfur-containing group represented by Formula (ii-1) or Formula (ii-2) in Formula (II) is not particularly limited, and the position may be the position of $R^{3b}$ or $R^{8b}$.

3. Additive Represented by Formula (III)

An additive represented by Formula (III) described above contains the above-described monovalent sulfur-containing group represented by Formula (iii-1) or (iii-2) in a salicylate-based skeleton.

In regard to Formula (iii-1), $R^{11c}$ represents a divalent hydrocarbon group having 1 to 12 carbon atoms, which may have a hydrogen atom substituted with a monovalent or divalent group selected from an aromatic group, an unsaturated group, a sulfur-containing group, an oxygen-containing group, a phosphorus-containing group, an alicyclic group and a halogen atom, which may have at least any one of two terminals interrupted by the monovalent or divalent group, or which may have a carbon-carbon bond interrupted by the monovalent or divalent group.

Examples of the divalent hydrocarbon group of $R^{11c}$ include a linear or branched alkylene group, an alkenylene group, and an alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group.

In a case in which the divalent hydrocarbon group of $R^{11c}$ has a hydrogen atom substituted with the monovalent or divalent group, has at least any one of two terminals interrupted by the monovalent or divalent group, or has a carbon-carbon bond interrupted by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (iii-1), t represents an integer of 0 or 1.

In regard to Formula (iii-2), $R^{12c}$ represents a divalent hydrocarbon group having 1 to 20 carbon atoms, which may have a hydrogen atom substituted with a monovalent or divalent group selected from an aromatic group, an unsaturated group, a sulfur-containing group, an oxygen-containing group, a phosphorus-containing group, an alicyclic group and a halogen atom, which may have at least any one of two terminals interrupted by the monovalent or divalent group, or which may have a carbon-carbon bond interrupted by the monovalent or divalent group.

Examples of the divalent hydrocarbon group of $R^{12c}$ include a linear or branched alkylene group, a linear or branched alkenylene group, and a linear or branched alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecan-1,13-yl group, a tetradecan-1,14-yl group, a pentadecan-1,15-yl group, a hexadecan-1,16-yl group, a heptadecan-1,17-yl group, an octadecan-1,18-yl group, a nonadecan-1,19-yl group, and an eicosan-1,20-yl group. Among these, an alkylene group is preferred, and a linear alkylene group is more preferred.

In a case in which the divalent hydrocarbon group of $R^{12c}$ has a hydrogen atom substituted with the monovalent or divalent group, has at least any one of two terminals interrupted by the monovalent or divalent group, or has a carbon-carbon bond interrupted by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (iii-2), in a case in which v is 2 or larger, $R^{13c}$'s each independently represent a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{13c}$ include the groups listed above as examples of the divalent hydrocarbon group of $R^{12c}$. Among these, an alkylene group is preferred, and a linear alkylene group is more preferred.

In a case in which the divalent hydrocarbon group of $R^{13c}$ is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (iii-2), $R^{14c}$ represents a monovalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the monovalent hydrocarbon group of $R^{14c}$ include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, a decan-1-yl group, an undecan-1-yl group, a dodecan-1-yl group, a tridecan-1-yl group, a tetradecan-1-yl group, a pentadecan-1-yl group, a hexadecan-1-yl group, a heptadecan-1-yl group, an octadecan-1-yl group, a nonan-1-yl group, and an eicosan-1-yl group. Among these, an alkyl group is preferred, and a linear alkyl group is more preferred.

In a case in which the monovalent hydrocarbon group of $R^{14c}$ is substituted a hydrogen atom with, interrupted a proximal terminal by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (iii-2), u represents an integer of 0 or 1, and v represents an integer from 0 to 3, and preferably 0 or 1.

In regard to Formula (iii-2), the total number of carbon atoms of $R^{12c}$, v units of $R^{13c}$, and $R^{14c}$ is 25 or less.

In regard to Formula (III), in a case in which $R^{1c}$ to $R^{10c}$ are each a group other than a monovalent sulfur-containing group represented by Formula (iii-1) or Formula (iii-2), $R^{1c}$ to $R^{10c}$ each represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group, and a halogen atom.

In a case in which $R^{1c}$ to $R^{10c}$ each represent a monovalent hydrocarbon group, examples of this monovalent hydrocarbon group include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, and a decan-1-yl group. Among these, a linear or branched alkyl group having 1 to 8 carbon atoms is preferred.

In a case in which $R^{1c}$ to $R^{10c}$ each represent an aromatic group, an unsaturated group, a sulfur-containing group, an oxygen-containing group, a phosphorus-containing group, an alicyclic group, or a halogen atom, specific examples thereof include the groups listed as examples in the section [Substituents] described above.

In regard to Formula (III), at least one of $R^{1c}$ to $R^{10c}$ is a monovalent sulfur-containing group represented by Formula (iii-1) or (Formula iii-2). Above all, when the ease or cost of actual synthesis and heat resistance are taken into consideration, or when it is taken into consideration that by making the compatibility with a resin serving as a matrix satisfactory, clouding of the resin member to which the additive of the present invention has been added can be suppressed, and manifestation of high ultraviolet absorbency or imparting of a high refractive index under addition of the additive in high concentrations is enabled, it is preferable that one or two of $R^{1c}$ to $R^{10c}$ are monovalent sulfur-containing groups represented by Formula (iii-1) or Formula (iii-2).

The position of the monovalent sulfur-containing group represented by Formula (iii-1) or Formula (iii-2) in Formula (III) is not particularly limited, and the position may be the position of $R^{7c}$ or $R^{9c}$.

In regard to the additives of Formulae (II) and (III), into which (ii-1) to (iii-1) have been introduced as monovalent sulfur-containing groups, upon considering heat resistance and the characteristics of enabling manifestation of high ultraviolet absorbency or imparting of a high refractive index when the additive is added in low concentrations to high concentrations, it is preferable that for the monovalent sulfur-containing group represented by Formula (ii-1), q is 0, or q is 1, with $R^{11b}$ including an alkylene group having 10 or fewer carbon atoms, and for the monovalent sulfur-containing group represented by Formula (iii-1), t is 0, or t is 1, with $R^{11c}$ including an alkylene group having 10 or fewer carbon atoms.

Compatibility with a resin serving as a matrix (transparency) is dependent on, in view of the structure of the additive, the number of carbon atoms of an alkyl group among the functional groups of Formula (i-v-1) and Formula (i-v-2) in the benzotriazole, benzophenone, salicylate and triazine skeletons in Formulae (I), (II), (III), (IV) and (V), and in view of properties, the melting point. However, regarding the melting point, there is no clear correlation between the number of carbon atoms of Formula (i-v-1) and Formula (i-v-2) and the melting point, and it is difficult to achieve a balance between the two factors, structure and properties.

These additives have a tendency that when the respective numbers of carbon atoms are adjusted by introducing sulfur-containing groups into the additives, melting points are lowered. When the melting point is lowered, particularly satisfactory compatibility with a resin serving as a matrix is obtained. From this point of view, it is preferable that for the monovalent sulfur-containing group represented by Formula (ii-1), q is 0, or q is 1, with $R^{11b}$ including an alkylene group having 9 or fewer carbon atoms, and for the monovalent sulfur-containing group represented by (iii-1), t is 0, or t is 1, with $R^{11c}$ including an alkylene group having 9 or fewer carbon atoms, while the melting point is 91° C. or lower at normal pressure (for example, standard atmospheric pressure 101325 Pa).

According to another preferred embodiment, the monovalent sulfur-containing group represented by Formula (ii-1) is such that q is 0, or q is 1, with $R^{11b}$ including an alkylene group having 8 or fewer carbon atoms, and the monovalent sulfur-containing group represented by Formula (iii-1) is such that t is 0, or t is 1, with $R^{11c}$ including an alkylene group having 8 or fewer carbon atoms, while the melting point is below 70° C. at normal pressure. Alternatively, the monovalent sulfur-containing group represented by Formula (ii-1) is such that q is 0, or q is 1, with $R^{11b}$ including an alkylene group having 8 or fewer carbon atoms, and the monovalent sulfur-containing group represented by Formula (iii-1) is such that t is 0, or t is 1, with $R^{11c}$ including an alkylene group having 8 or fewer carbon atoms, while the melting point is 35° C. or lower at normal pressure. That is, when the number of carbon atoms is 8 or less, and the melting point is below 70° C., even if the additive is added in high concentrations, high transparency is obtained at large film thicknesses. Furthermore, if the additive is liquid at normal temperature (5° C. to 35° C.), high transparency can be realized even if the additive is added in high concentrations at larger film thicknesses.

Regarding the additives of Formulae (II) and (III) into which (ii-2) to (iii-2) have been introduced as monovalent sulfur-containing groups, when it is taken into consideration that manifestation of high ultraviolet absorbency or imparting of a high refractive index is enabled through addition in low concentrations to high concentrations, it is preferable that for the monovalent sulfur-containing group represented by Formula (ii-2), $R^{12b}$ and s units of $R^{13b}$ each includes an alkylene group having 18 or fewer carbon atoms, with $R^{14b}$ including an alkyl group having 18 or fewer carbon atoms, and for the monovalent sulfur-containing group represented by Formula (iii-2), $R^{12c}$ and v units of $R^{13c}$ each includes an alkylene group having 18 or fewer carbon atoms, with $R^{14c}$ including an alkyl group having 18 or fewer carbon atoms.

Furthermore, these additives have a tendency that when the respective numbers of carbon atoms are adjusted from short chain to medium chains by introducing sulfur-containing groups into the additives, melting points are lowered. When the melting point is lowered, particularly satisfactory compatibility with a resin serving as a matrix is obtained. When this is taken into consideration, it is preferable that for the monovalent sulfur-containing group represented by Formula (ii-2), $R^{12b}$ and s units of $R^{13b}$ each includes an alkylene group having 18 or fewer carbon atoms, with $R^{14b}$ including an alkyl group having 18 or fewer carbon atoms, and for the monovalent sulfur-containing group represented by Formula (iii-2), $R^{12c}$ and v units of $R^{13c}$ each includes an alkylene group having 18 or fewer carbon atoms, with $R^{14c}$ including an alkyl group having 18 or fewer carbon atoms, while the melting point is 91° C. or lower at normal pressure.

According to another preferred embodiment, the monovalent sulfur-containing group represented by Formula (ii-2) is such that $R^{12b}$ and s units of $R^{13b}$ each includes an alkylene group having 8 or fewer carbon atoms, with $R^{14b}$ including an alkyl group having 8 or fewer carbon atoms, and the monovalent sulfur-containing group represented by Formula (iii-2) is such that $R^{12c}$ and v units of $R^{13c}$ each includes an alkylene group having 8 or fewer carbon atoms, with $R^{14c}$ including an alkyl group having 8 or fewer carbon atoms, while the melting point is below 70° C. at normal pressure. Alternatively, the monovalent sulfur-containing group represented by Formula (ii-2) is such that $R^{12b}$ and s units of $R^{13b}$ each includes an alkylene group having 8 or fewer carbon atoms, with $R^{14b}$ including an alkyl group having 8 or fewer carbon atoms, and the monovalent sulfur-containing group represented by Formula (iii-2) is such that $R^{12c}$ and v units of $R^{13c}$ each includes an alkylene group having 8 or fewer carbon atoms, with $R^{14c}$ including an alkyl group having 8 or fewer carbon atoms, while the melting point is 35° C. or lower at normal pressure. That is, when the number of carbon atoms is 8 or less, and the melting point is below 70° C., even if the additive is added in high concentrations, high transparency is obtained at large film thicknesses. Furthermore, if the additive is liquid at normal temperature (5° C. to 35° C.), high transparency can be realized even if the additive is added in high concentrations at larger film thicknesses. 4. Additive Represented by Formula (IV)

An additive represented by Formula (IV) described above contains the above-described monovalent sulfur-containing group represented by Formula (iv-1) or (iv-2) in a triazine-based skeleton.

The additive represented by Formula (IV) may be solid or may be liquid, and when a monovalent sulfur-containing group is introduced thereinto, heat resistance is increased, particularly satisfactory compatibility with a resin serving as a matrix is obtained, and even if the additive is added in high concentrations, high transparency is obtained.

In regard to Formula (iv-1), $R^{16d}$ represents a divalent hydrocarbon group having 1 to 12 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{16d}$ include a linear or branched alkylene group, an alkenylene group, and an alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group.

In a case in which the divalent hydrocarbon group of $R^{16d}$ is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

Among these, when it is considered that by improving the compatibility with a resin serving as a matrix, clouding of the resin member to which the additive of the present invention has been added can be suppressed, and manifestation of high ultraviolet absorbency or imparting of a high refractive index under addition of the additive in high concentrations is enabled, a divalent hydrocarbon group having 1 to 9 carbon atoms is preferred, and a divalent hydrocarbon group having 1 to 8 carbon atoms is more preferred. Furthermore, when this is taken into consideration, an embodiment in which w=0, that is, Formula (iv-1) represents —SH, is also similarly preferable. Among the hydrocarbon groups, an alkylene group is preferred, and the monovalent sulfur-containing group represented by Formula (iv-1) according to a preferred embodiment is such that w is 0, or w is 1, with $R^{16d}$ including an alkylene group having 8 or fewer carbon atoms. The alkylene group is particularly preferably a linear alkylene group.

In regard to Formula (iv-1), w represents an integer of 0 or 1.

In regard to Formula (iv-2), $R^{17d}$ represents a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{17d}$ include a linear or branched alkylene group, a linear or branched alkenylene group, and a linear or branched alkynylene group. Specific examples include a methylene group, an ethane-1,2-diyl group, a propane-1,3-diyl group, a 1-methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecan-1,13-yl group, a tetradecan-1,14-yl group, a pentadecan-1,15-yl group, a hexadecan-1,16-yl group, a heptadecan-1,17-yl group, an octadecan-1,18-yl group, a nonadecan-1,19-yl group, and an eicosan-1,20-yl group. Among these, an alkylene group is preferred, and a linear alkylene group is more preferred.

In a case in which the divalent hydrocarbon group of $R^{17d}$ is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, halogen atom of the monovalent or divalent group include the groups listed as examples in the section [Substituents] described above.

In regard to Formula (iv-2), in a case in which y of $R^{18d}$ is 2 or larger, $R^{18d}$'s each independently represent a divalent hydrocarbon group having 1 to 20 carbon atoms which may be substituted a hydrogen atom with, interrupted at least any one of two terminals by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the divalent hydrocarbon group of $R^{18d}$ include the groups listed above as examples of the divalent hydrocarbon group of $R^{17d}$. Among these, an alkylene group is preferred, and a linear alkylene group is more preferred.

In a case in which the divalent hydrocarbon group of $R^{18d}$ is substituted a hydrogen atom with, interrupted at least any one of two terminals by or interrupted a carbon-carbon bond by the monovalent or divalent group, the number of the monovalent or divalent groups is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (iv-2), $R^{19d}$ represents a monovalent hydrocarbon group having 1 to 20 carbon atoms which may be substituted a hydrogen atom with, interrupted a proximal terminal by or interrupted a carbon-carbon bond by a monovalent or divalent group selected from an aromatic group, an unsaturated group, a sulfur-containing group, an oxygen-containing group, a phosphorus-containing group, an alicyclic group and a halogen atom.

Examples of the monovalent hydrocarbon group of $R^{19d}$ include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, a decan-1-yl group, an undecan-1-yl group, a dodecan-1-yl group, a tridecan-1-yl group, a tetradecan-1-yl group, a pentadecan-1-yl group, a hexadecan-1-yl group, a heptadecan-1-yl group, an octadecan-1-yl group, a nonan-1-yl group, and an eicosan-1-yl group. Among these, an alkyl group is preferred, and a linear alkyl group is more preferred.

In a case in which the monovalent hydrocarbon group of $R^{19d}$ is substituted a hydrogen atom with, interrupted a proximal terminal by or interrupted a carbon-carbon bond by the monovalent or divalent group, the number of substituents is preferably 2 or less, and more preferably 1 or less.

Specific examples of the aromatic group, unsaturated group, sulfur-containing group, oxygen-containing group, phosphorus-containing group, alicyclic group, and halogen atom of the monovalent or divalent group include the groups listed as examples in the section [Substituents] described above.

In regard to Formula (iv-2), x represents an integer of 0 or 1, and y represents an integer from 0 to 3, and preferably 0 or 1.

In regard to Formula (iv-2), the total number of carbon atoms of $R^{17d}$, y units of $R^{18d}$, and $R^{19d}$ is preferably 54 or less, more preferably 36 or less, and particularly preferably 25 or less. Above all, when it is considered that by improving the compatibility with a resin serving as a matrix, clouding of the resin member to which the additive of the present invention has been added can be suppressed, and manifestation of high ultraviolet absorbency or imparting of a high refractive index under addition of the additive in high concentrations is enabled, it is preferable that the monovalent sulfur-containing group represented by Formula (iv-2)

is such that $R^{17d}$ and y units of $R^{18d}$ each include an alkylene group having 18 or fewer carbon atoms, while $R^{19d}$ is an alkyl group having 18 or fewer carbon atoms; it is more preferable that $R^{17d}$ and y units of $R^{18d}$ each include an alkylene group having 12 or fewer carbon atoms, while $R^{19d}$ is an alkyl group having 12 or fewer carbon atoms; and it is particularly preferable that $R^{17d}$ and y units of $R^{18d}$ each include an alkylene group having 8 or fewer carbon atoms, while $R^{19d}$ is an alkyl group having 8 or fewer carbon atoms. Furthermore, it is preferable that $R^{17d}$, y units of $R^{18d}$, and $R^{19d}$ are all straight chains, and $R^{17d}$, $R^{18d}$ and $R^{19d}$ each have 1 to 18 carbon atoms. It is more preferable that $R^{17d}$, $R^{18d}$, and $R^{19d}$ each have 1 to 12 carbon atoms, and it is even more preferable that $R^{17d}$, $R^{18d}$, and $R^{19d}$ each have 1 to 8 carbon atoms, still more preferably 1 to 6 carbon atoms, and particularly preferably one carbon atom (here, the case in which x=0, and the case in which y=0 are also included).

In regard to Formula (IV), in a case in which $R^{1d}$ to $R^{15d}$ each represent a group other than the monovalent sulfur-containing group represented by Formula (iv-1) or Formula (iv-2), $R^{1d}$ to $R^{15d}$ each represent a monovalent group selected from a hydrogen atom, a hydrocarbon group having 1 to 10 carbon atoms, an aromatic group, an unsaturated group, a sulfur-containing group, an oxygen-containing group, a phosphorus-containing group, an alicyclic group, and a halogen atom.

In a case in which $R^{1d}$ to $R^{15d}$ each represent a monovalent hydrocarbon group, examples of this monovalent hydrocarbon group include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, and a decan-1-yl group. Among these, a linear or branched alkyl group having 1 to 8 carbon atoms is preferred.

In a case in which $R^{1d}$ to $R^{15d}$ each represent a monovalent group selected from an aromatic group, an unsaturated group, a sulfur-containing group, an oxygen-containing group, a phosphorus-containing group, an alicyclic group, and a halogen atom, specific examples thereof include the groups listed as examples in the section [Substituents] described above.

In regard to Formula (IV), at least one of $R^{1d}$ to $R^{15d}$ is a monovalent sulfur-containing group represented by Formula (iv-1) or Formula (iv-2). Above all, when the ease or cost of actual synthesis and heat resistance are taken into consideration, or when it is taken into consideration that by making the compatibility with a resin serving as a matrix satisfactory, clouding of the resin member to which the additive of the present invention has been added can be suppressed, and manifestation of high ultraviolet absorbency or imparting of a high refractive index under addition of the additive in high concentrations is enabled, it is preferable that one to three among $R^{1d}$ to $R^{15d}$ are monovalent sulfur-containing groups represented by Formula (iv-1) or Formula (iv-2).

The position of the monovalent sulfur-containing group represented by Formula (iv-1) or Formula (iv-2) in Formula (IV) is not particularly limited; however, the position may be the position of $R^{3d}$, $R^{8d}$ or $R^{13d}$.

The monovalent sulfur-containing group represented by Formula (iv-1) or Formula (iv-2) is incorporated into a triazine-based skeleton. Alkyl group having 10 to 24 carbon atoms.

5. Additive Represented by Formula (V)

An additive represented by Formula (V) described above includes a long-chain alkyl group in a benzotriazole-based skeleton.

In regard to Formula (V), at least one of $R^{1e}$ to $R^{9e}$ is an alkyl group having 10 to 24 carbon atoms. This alkyl group having 10 to 24 carbon atoms has a linear chain having 10 to 20 carbon atoms, and hydrogen atom of the linear chain may be substituted by two or fewer alkyl groups each having 1 or 2 carbon atoms. Among them, a linear alkyl group is preferred.

Specific examples of this alkyl group having 10 to 24 carbon atoms include a decan-1-yl group, an undecan-1-yl group, a dodecan-1-yl group, a tridecan-1-yl group, a tetradecan-1-yl group, a pentadecan-1-yl group, a hexadecan-1-yl group, a heptadecan-1-yl group, an octadecan-1-yl group, a nonan-1-yl group, an eicosan-1-yl group, a heneicosan-1-yl group, a docosan-1-yl group, a tricosan-1-yl group, and a tetracosan-1-yl group.

In regard to Formula (V), in a case in which $R^{1e}$ to $R^{9e}$ each represent a group other than the alkyl group having 10 to 24 carbon atoms as described above, $R^{1e}$ to $R^{9e}$ each represent a monovalent group selected from a hydrogen atom, a hydrocarbon group having 1 to 4 carbon atoms, an aromatic group, an unsaturated group, an oxygen-containing group, a phosphorus-containing group, an alicyclic group, and a halogen atom.

In a case in which $R^{1e}$ to $R^{9e}$ each represent a monovalent hydrocarbon group, examples of this monovalent hydrocarbon group include a linear or branched alkyl group, a linear or branched alkenyl group, and a linear or branched alkynyl group. Specific examples include a methyl group, an ethan-1-yl group, a propan-1-yl group, a 1-methylethan-1-yl group, a butan-1-yl group, a butan-2-yl group, a 2-methylpropan-1-yl group, and a 2-methylpropan-2-yl group.

In a case in which $R^{1e}$ to $R^{9e}$ each represent an aromatic group, an unsaturated group, a sulfur-containing group, an oxygen-containing group, a phosphorus-containing group, an alicyclic group, or a halogen atom, specific examples thereof include the groups listed as examples in the section [Substituents] described above.

In regard to Formula (V), at least one of $R^{1e}$ to $R^{9e}$ is the alkyl group having 10 to 24 carbon atoms described above. Above all, when the ease or cost of actual synthesis is taken into consideration, or when it is taken into consideration that by making the compatibility with a resin serving as a matrix satisfactory, clouding of the resin member to which the additive of the present invention has been added can be suppressed, and manifestation of high ultraviolet absorbency or imparting of a high refractive index under addition of the additive in high concentrations is enabled, it is preferable that one or two of $R^{1e}$ to $R^{9e}$ are the alkyl group having 10 to 24 carbon atoms described above.

The position of the alkyl group having 10 to 24 carbon atoms described above in regard to Formula (V) is not particularly limited, and the position may be the position of $R^{2e}$ or $R^{4e}$.

According to the present invention, in regard to the relation between the fact that compatibility between an additive and a resin can be enhanced, and the melting point of the additive, the following is considered. In a case in which the intermolecular interaction of the additive is strong, the interaction between the molecules of the additive and the molecules of the resin is difficult, and compatibility thereof is decreased. On the other hand, in a case in which the intermolecular interaction of the additive is strong, the melting point of the additive rises. That is, the melting point of the additive serves as an index for the interaction between the molecules of the additive and for compatibility between the additive and the resin, and it is speculated that by incorporating a sulfur-containing group into the additive and incorporating an appropriately selected alkyl group into the additive, and by reducing the interaction between the molecules of the additive (lowering of the melting point), compatibility between the additive and the resin can be increased.

The additives of the present invention exhibit ultraviolet absorbency by means of the benzotriazole-based ultraviolet absorbing skeleton or the like, the additives cut the wavelengths in the ultraviolet region by having an ultraviolet absorption band in the vicinity of 250 to 400 nm while transmitting the wavelengths in the visible light region. There is a demand for an ultraviolet absorber that can even absorb light in the UV-A region (315 to 400 nm), which region affects photodegradation of all organic substances. However, the additives of the present invention have excellent ultraviolet absorbency for the UV-A region, and depending on the chemical structure, the additives are even capable of cutting ultraviolet ray up to a region near 400 nm. Furthermore, through introduction of the functional groups of Formulae (i-1,2) to (iv-1,2), the increase of the refractive index as well as the region of the ultraviolet absorption band can be controlled, and the functions can be enhanced. An additive of the present invention obtained by introducing a thioether group (i-2 or iv-2) into a benzotriazole group of a benzotriazole-based compound or into an a triazine-based compound, shifts significantly to a long wavelength without cutting 450 to 500 nm (visible range) and is capable of cutting ultraviolet ray in the vicinity of 360 to 400 nm, which is considered as a longer wavelength range even in the UV-A region. On the other hand, regarding an additive of the present invention obtained by introducing a thioether group of (i-2) into the phenyl group on a nitrogen atom of the benzotriazole-based compound, the absorption band shifts to a short wavelength, and the additive may have an absorption band near 290 nm in a short wavelength region. Furthermore, an additive of the present invention obtained by introducing one thioether group (iv-2) into the triazine-based compound of the present invention, has an ultraviolet absorption band in the region of short wavelength ultraviolet ray, namely, 260 to 280 nm, in addition to an ultraviolet absorption band in a long wavelength region in the vicinity of 360 to 400 nm, so that those the additive enables ultraviolet absorption in a wider range.

The additives of the present invention can retain transparency of resins when the additives are added to the resins. Also, since the additives of the present invention have excellent heat resistance, the additives are not easily thermally decomposed in the course of heating, molding and processing a resin member containing such an additive, and therefore, a resin member that does not have impaired external appearance and in which the ultraviolet absorbency and high refractive index characteristics are not deteriorated, is obtained. Furthermore, regarding a transparent resin member, a member having high transparency is obtained.

A transparent resin member containing an additive of the present invention represented by Formula (I), in which the thioether group of (i-2) has been introduced into any one of $R^{6a}$ to $R^{9a}$, enables absorption of wavelengths in a long wavelength region while suppressing yellowing, by the benefit of peak characteristics of ultraviolet absorption in addition to the heat resistance of such an additive, the transparency of the resin based on compatibility to the resin, and an increased refractive index of the resin.

On the other hand, in regard to the additives of the present invention represented by Formula (I) to Formula (V) having reactive functional groups such as a hydroxyl group, a thiol group, a carboxyl group, an amino group and a silyl group, which include polymerizable functional groups and cross-linkable functional groups such as a carbon-carbon double bond, a vinyl group, a vinyloxy group, an allyl group, a (meth)acryloyl group, a maleoyl group, a styryl group and a cinnamoyl group, in the thiol groups of (i-1) to (iv-1) and the thioether groups of (i-2) to (iv-2), in a case in which a resin member is obtained by performing reaction, copolymerization and molding processing using raw material monomers and a resin for films and resin members containing functional groups (for example, an isocyanate group, an epoxy group, a carboxylic acid group, a carbonyl group, a hydroxyl group, an alkenyl group, an alkynyl group, an ether group, a thioisocyanate group, a thioepoxy group, a thiocarboxylic acid group, a thiocarbonyl group, and a thiol group) that react with those functional groups, the above-described additives are copolymerized with those monomers or react with the functional groups of the resin, thereby being immobilized in the matrix. Thus, transparency can be maintained, and the respective functions of ultraviolet absorbency and increase of refractive index can be maintained for a long period of time, without any bleed-out of the additives.

Furthermore, as sulfur-containing groups are introduced, the refractive index is increased, and a high refractive index can be imparted to a resin member. The values of refractive index of the additives of the present invention are not particularly limited; however, the values are, for example, 1.55 or larger, preferably 1.58 to 1.62, and more preferably in the range of 1.60 to 1.62.

The additives of the present invention have increased compatibility with resin members and can be dissolved in high concentrations such as 0.4 wt % or more, even 10 wt % or more, and particularly 30 wt % or more, while maintaining high transparency, by having a sulfur-containing group, particularly a sulfur-containing group having a short-chain to medium-chain hydrocarbon as a spacer, into a benzotriazole-based ultraviolet-absorbing skeleton. Therefore, at least any one of high ultraviolet absorbency and a high refractive index can be imparted while high transparency is maintained. That is, dissolution in high concentrations in a resin member in which dissolution in high concentrations is impossible with existing ultraviolet absorbers and refractive index enhancers is enabled, and thus, transparency as well as higher ultraviolet absorbency or a high refractive index can be imparted to a resin member.

Above all, if an additive of the present invention has a melting point of below 70° C. and is a liquid at normal temperature of 35° C. or lower, the additive has particularly satisfactory compatibility with a resin member. In particular, benzotriazole-based, benzophenone-based, and salicylate-based additives are such that even if the additives are added at a high concentration of 50 wt % or more, a matrix having high transparency is obtained.

Furthermore, imparting of ultraviolet absorbency and imparting of a high refractive index to a matrix can be both achieved simply by adding one additive to one sheet of film or sheet. For example, in regard to a film or member having a functional optical layer, such as a multilayer optical film, it is also possible to make two layers (an ultraviolet absorbing layer and a high refractive index layer) into a single layer using only one additive.

When the additives represented by Formula (I) to Formula (V) are produced, reference may be made to the disclosure of the following Examples and known technologies.

6. Resin Member Using Additive of Present Invention

A resin member of the present invention contains an additive of the present invention such as explained above.

The shape of the resin member of the present invention is not particularly limited, and any arbitrary shape may be adopted. However, from the viewpoint that high ultraviolet absorbency and/or a high refractive index can be imparted while maintaining transparency, a laminated multilayer structure can be simplified, and thus the number of production processes and the production cost can be reduced. Above all, one layer in a member having a multilayer structure, a film or sheet having softness or flexibility, or a plate-like member having a plate-sheet with rigidity is preferred, and in addition to those, optical molded articles, for example, optical lenses such as glasses lens and contact lenses, are preferred.

Resin members containing the additives of the present invention can maintain transparency of the resins. Also, since the additives of the present invention have excellent heat resistance, the additives are not easily thermally decomposed in the course of heating, molding and processing a resin member containing such an additive, and therefore, a resin member that does not have impaired external appearance and in which the ultraviolet absorbency and high refractive index characteristics of the resin member are not deteriorated, is obtained. Furthermore, regarding a transparent resin member, a member having high transparency is obtained.

Furthermore, transparent resin members containing the additives of the present invention represented by Formula (I) to Formula (V) in which the thioether group of (iv-2) has been introduced into $R^{6a}$ to $R^{9a}$, enable absorption of the wavelengths in a long wavelength region while suppressing yellowing, due to the transparency and increased refractive indices of resins obtainable by the heat resistance of the those additives and compatibility with the resins, as well as the characteristics of ultraviolet absorption peaks. In regard to resin members containing the additives of the present invention represented by Formula (I) to Formula (V) having reactive functional groups such as a thiol group, a vinyl group and a hydroxyl group in the thiol groups of (i-1) to (iv-1) and the thioether groups of (i-2) to (iv-2), in a case in which a resin member is obtained by performing reaction and molding processing using raw material monomers and a resin for films and resin members containing functional groups (for example, an isocyanate group, an epoxy group, a carboxylic acid group, a carbonyl group, a hydroxyl group, an alkenyl group, an alkynyl group, an ether group, a thioisocyanate group, a thioepoxy group, a thiocarboxylic acid group, a thiocarbonyl group, and a thiol group) that react with the reactive functional groups such as a thiol group, a vinyl group and a hydroxyl group contained in those additives, the above-described additives in the resulting resin react with the functional groups of those monomers and the resin, thereby being immobilized in the matrix. Thus, the resin can maintain the respective functions of ultraviolet absorbency and increase of the refractive index for a long period of time, without any bleed-out of the additives.

A transparent resin member containing an additive of the present invention in which the substituent represented by Formula (i-1) or Formula (i-2) has been introduced into $R^{6a}$ to $R^{9a}$ of Formula (I), maintains transparency and a high refractive index, and due to the characteristics of ultraviolet absorbency of the additive, the transparent resin member is capable of sharply cutting ultraviolet ray in the vicinity of 360 to 400 nm, which is considered as a longer wavelength range even in the UV-A region, without cutting the wavelengths of 450 to 500 nm (visible range). For this reason, a resin member having suppressed yellow coloration and excellent external appearance is obtained.

The resin member of the present invention is not particularly limited, and examples thereof include acrylic resins such as polymethyl (meth)acrylate, polyethyl (meth)acrylate, and a methyl (meth)acrylate-butyl (meth)acrylate copolymer; polyolefin-based resins such as polyethylene, polypropylene, polymethylpentene, and a cyclic olefin-based polymer; thermoplastic polyester resins such as a polycarbonate resin, polyethylene terephthalate, and polyethylene naphthalate; thermoplastic resins such as polyurethane, polythiourethane, polystyrene, polyamide, polyimide, an acrylonitrile-styrene copolymer, a polyether sulfone, a polysulfone, a cellulose-based resin such as triacetyl cellulose, polyvinyl acetate, an ethylene-vinyl acetate copolymer, polyvinylpyrrolidone, polyvinyl chloride, polyvinylidene chloride, polyether ether ketone, polyacetal, and nylon; thermosetting resins of urethane, thiourethane, urea, melamine, acrylic melamine, episulfide, epoxy, allyl, silicone, phenol, urea, and unsaturated polyesters; and ultraviolet-curable resins such as acrylics, for example, a monofunctional or polyfunctional (meth)acrylate compound such as an acrylic acid ester of a polyhydric alcohol, 2-hydroxyethyl methacrylate, or a methacrylic acid ester; a polyfunctional urethane (meth)acrylate compound synthesized from a diisocyanate and a polyhydric alcohol, or a hydroxy ester of acrylic acid or methacrylic acid; and ultraviolet-curable resins such as a polyether, a polyester, an epoxy resin, an alkyd resin, a spiroacetal resin, a polybutadiene, and a polythiol-polyene, all of which have acrylate-based functional groups.

The resin member of the present invention can be produced by, for example, the following methods (1) to (4), without any particular limitations.

(1) A method of forming a film by applying a coating liquid containing an additive of the present invention and a resin or raw material monomers, on a base material, and subjecting the coating liquid to heating, irradiation with ultraviolet ray or drying.

(2) A method of mixing and then kneading an additive of the present invention with a resin or raw material monomers, and molding the mixture and processing it into a film using an extruder or the like.

(3) A method of incorporating an additive of the present invention into a resin adhesive, and applying the resin adhesive on a film.

(4) A method of dissolving an additive of the present invention in raw material monomers, casting the solution into a mold or a glass mold, curing the raw material monomers by heating, irradiating with ultraviolet radiation, or drying to thereby mold a resin.

Among these methods, the method of (1) of forming a film by applying a coating liquid containing an additive of the present invention and a resin or raw material monomer materials, is suitable for the present invention from the viewpoint of obtaining a transparent multilayer structure, a film, or a sheet.

In this method, a coating liquid is produced by diluting the additive of the present invention and the resin or raw material monomers in an organic solvent or a water-based solvent, or without diluting the materials, and a film is formed by applying the coating liquid on a base material. If necessary, drying, cooling, heating, and irradiation with ultraviolet ray are performed, and thus the film strength is increased.

The resin is not particularly limited, and for example, any film or member having a functional optical layer can be selected as appropriate, while considering necessary properties such as adhesiveness to a base material and hardness. Specific examples include an ultraviolet-curable resin, an electron beam-curable resin, a thermosetting resin, and a thermoplastic resin. More specific examples include a polyester resin, an acrylic resin, a urethane resin, a thiourethane resin, a polyethylene terephthalate resin, a polystyrene resin, a polycarbonate resin, a urea resin, a melamine resin, an acrylic melamine resin, an epoxy resin, an alkyd resin, a spiroacetal resin, a polybutadiene resin, a polyolefin resin, a polyvinyl resin, a polyvinyl alcohol resin, a polyvinyl-based modified resin (PVB, EVA and the like), a silicone resin, a polyamide resin, a polyether resin, an episulfide resin, a nylon resin, and copolymer resins thereof.

In regard to a film or member having a functional optical layer, an ultraviolet-curable resin, an electron beam-curable resin, a thermosetting resin, a thermoplastic resin, and the like can be used. A coating liquid containing these resins is applied on a transparent base material to form a coating film, and this coating film is subjected to a drying treatment as necessary. Subsequently, the coating film is subjected to a curing reaction by irradiating the coating film with ultraviolet ray or an electron beam or heating the coating film, and thus a transparent optical layer can be formed.

Regarding the ultraviolet-curable resin, an acrylic material can be used. Examples of the acrylic material that can be used include a monofunctional or polyfunctional (meth)acrylate compound such as an acrylic acid or methacrylic acid ester; and a polyfunctional urethane (meth)acrylate compound synthesized from a diisocyanate, a polyhydric alcohol, and a hydroxy ester of acrylic acid or methacrylic acid. In addition to these, a polyether resin, a polyester resin, an epoxy resin, an alkyd resin, a spiroacetal resin, a polybutadiene resin, a polythiol-polyene resin and the like, all of which have acrylate-based functional groups, can also be used.

In the case of using an ultraviolet-curable resin, a photopolymerization initiator is added to the coating liquid. The photopolymerization initiator may be any agent capable of generating a radical when irradiated with ultraviolet ray. For example, an acetophenone, a benzoin, a benzophenone, a phosphine oxide, a ketal, an anthraquinone, and a thioxanthone can be used.

Examples of the thermosetting resin that can be used include a urethane resin, a thiourethane resin, a melamine resin, an acrylic melamine resin, a urea resin, a phenolic resin, an epoxy resin, and an episulfide resin.

Examples of the thermoplastic resin that can be used include a urethane resin, a thiourethane resin, a polyethylene terephthalate resin, a polystyrene resin, a polycarbonate resin, a polyester resin, a polyethylene resin, a polypropylene resin, an acrylic resin, and a nylon resin.

If necessary, a solvent for diluting the coating liquid may be added to the coating liquid. Examples of the solvent include aromatic hydrocarbons such as toluene, xylene, cyclohexane, and cyclohexylbenzene; hydrocarbons such as n-hexane; ethers such as dibutyl ether, dimethoxymethane, dimethoxyethane, diethoxyethane, propylene oxide, dioxane, dioxolane, trioxane, tetrahydrofuran, anisole, and phenetole; ketones such as methyl isobutyl ketone, methyl butyl ketone, acetone, methyl ethyl ketone, diethyl ketone, dipropyl ketone, diisobutyl ketone, cyclopentanone, cyclohexanone, and methylcyclohexanone; esters such as ethyl formate, propyl formate, n-pentyl formate, methyl acetate, ethyl acetate, methyl propionate, ethyl propionate, n-pentyl acetate, and γ-butyrolactone; cellosolves such as methyl cellosolve, cellosolve, butyl cellosolve, and cellosolve acetate; alcohols such as methanol, ethanol, and isopropyl alcohol; and water.

If necessary, additives such as an antifoaming agent, a leveling agent, an oxidation inhibitor, a photostabilizer, a polymerization inhibitor, a catalyst, a dye, and a pigment may also be incorporated into the coating liquid.

The amount of use of the additives of the present invention varies depending on the purpose, and is not particularly limited in consideration of ultraviolet absorbency, increase of refractive index, transparency and the like. However, the additives can be added in an amount of 0.4 wt % or more, even 10 wt % or more, even 30 wt % or more, and particularly 50 wt % or more, with respect to the total amount of the coating liquid excluding volatile components such as a solvent. Even if the additives are added in such high concentrations, the additives of the present invention uniformly dissolve in a resin serving as a matrix, and thus high transparency can be maintained.

The coating liquid thus produced can be applied on a base material according to an appropriate method such as bar coating, gravure coating, comma coating, lip coating, curtain coating, roll coating, blade coating, spin coating, reverse coating, die coating, spraying, or dipping.

The base material for coating is not particularly limited; however, examples include a resin plate, a resin film, a resin sheet, a glass, and a construction material.

In a case in which the resin member of the present invention is used as a portion of a film or member having a functional optical layer such as an antireflection film, the material can be selected by taking into consideration of optical characteristics such as transparency and light refractive index, and various properties such as impact resistance, heat resistance and durability, for a base material for coating. Such a material is not particularly limited; however, examples include acrylic resins such as polymethyl (meth)acrylate, polyethyl (meth)acrylate, and a methyl (meth)acrylate-butyl (meth)acrylate copolymer; polyolefin-based resins such as polyethylene, polypropylene, polymethylpentene, and a cyclic olefin-based polymer; thermoplastic polyester resins such as a polycarbonate resin, polyethylene terephthalate, and polyethylene naphthalate; thermoplastic resin materials such as polyamide, polyimide, polystyrene, an acrylonitrile-styrene copolymer, polyether sulfone, polysulfone, a cellulose-based resin such as triacetyl cellulose, polyvinyl acetate, an ethylene-vinyl acetate copolymer, polyvinyl chloride, polyvinylidene chloride, polyether ether ketone, and polyurethane; glasses (including ceramics) such as soda glass, potash glass, and lead glass; and light-transmitting inorganic materials such as quartz, fluorite, and diamond.

To these materials, known additives, for example, an ultraviolet absorber, an infrared absorber, a refractive index enhancer, a plasticizer, a lubricating agent, a colorant, an oxidation inhibitor, and a flame retardant, may also be used.

The thickness of the base material in the case of being used as a film having a functional optical layer is not particularly limited; however, the thickness is, for example, 50 nm to 150 m. Furthermore, such a base material may have a single layer, or may be a laminate of a plurality of layers.

Furthermore, among the above-described methods for producing the resin member of the present invention, in the (2) method of mixing and then kneading an additive of the present invention with a resin, and molding the mixture and processing it into a film using an extruder or the like, the resin member can be produced by adding the additive of the present invention to a powder or pellets of the resin, heating and melting the resin powder or pellets, and then molding the molten resin.

The powder or pellets of the resin are not particularly limited; however, examples include acrylic resins such as polymethyl (meth)acrylate, polyethyl (meth)acrylate, and a methyl (meth)acrylate-butyl (meth)acrylate copolymer; polyolefin-based resins such as polyethylene, polypropylene, polymethylpentene, and cyclic olefin-based polymers; thermoplastic polyester resins such as a polycarbonate resin, polyethylene terephthalate, and polyethylene naphthalate; and thermoplastic resin materials such as polyamide, polyimide, polystyrene, an acrylonitrile-styrene copolymer, polyether sulfone, polysulfone, a cellulose-based resin such as triacetyl cellulose, polyvinyl acetate, an ethylene-vinyl acetate copolymer, polyvinylpyrrolidone, polyvinyl chloride, polyvinylidene chloride, polyether ether ketone, polyacetal, nylon, and polyurethane.

The method for molding a resin member is not particularly limited; however, an injection molding method, an extrusion molding method, a calender molding method, a blow molding method, a compression molding method or the like can be used. In the case of using an extruder, a resin member can be produced by producing a film using an extruder, or producing a original sheet using an extruder, and then stretching the original sheet uniaxially or biaxially to produce a film.

The additive of the present invention acquires enhanced heat resistance by having a thioether group introduced thereinto. Since the 5% weight reduction temperature of the additive of the present invention is higher than 100° C. to 250° C., which correspond to the softening points of general resins ("Well-Known Plastics", reviewed by Japan Plastics Industry Federation, published by Nippon Jitsugyo Publishing Co., Ltd.), the additive of the present invention can be applied to thermosetting resins and thermoplastic resins having molding processing temperatures of 100° C. to 200° C., as well as thermoplastic resins which require molding processing temperatures higher than 200° C. to 250° C.

When the additive and a resin are kneaded, those additives used for conventional resin molding, such as an infrared absorber, an ultraviolet absorber, a refractive index enhancer, an oxidation inhibitor, a photostabilizer, a flame retardant, and a plasticizer may also be added.

Among the above-described methods for producing the resin member of the present invention, in the (3) method of incorporating an additive of the present invention into a resin adhesive, and applying the resin adhesive on a film, a composite material including the resin member of the present invention can be produced by using known transparent adhesive such as a silicone-based, urethane-based, acrylic, polyvinyl butyral adhesive (PVB), ethylene-vinyl acetate-based, or epoxy-based adhesives, which are generally used as resin adhesives, adhering resin films using a resin adhesive to which the additive of the present invention has been added, and curing the resin films.

The film thickness in a case in which the resin member of the present invention is used as a portion of a film or member having a functional optical layer is not particularly limited as long as the film thickness is in a range that can satisfy required properties such as type of the resin material, adhesiveness and hardness, and the film thickness is, for example, in the range of 50 nm to 200 μm.

Furthermore, among the above-described methods for producing the resin member of the present invention, in the (4) method of dissolving an additive of the present invention in raw material monomers, casting the solution into a mold or a glass mold, curing the raw material monomers by heating, irradiating with ultraviolet radiation, or drying to thereby mold a resin, in the case of curing by heating, monomers for thermosetting resins can be used, and examples include, without particular limitations, the resin raw material monomers capable of producing urethane, thiourethane, epoxy, thioepoxy, melamine, silicone, phenol, urea, and unsaturated polyester resins can be used. The additive of the present invention is dissolved in at least one kind of monomer among the resin raw material monomers, the other resin monomers needed for resin production are mixed thereinto, and then the mixture is cast into a mold or a glass mold and heated. Thereby, a resin member containing the additive of the present invention can be produced. As an ultraviolet-curable resin, an acrylic material can be used. Examples of the acrylic material that can be used include monofunctional or polyfunctional (meth)acrylate compounds such as 2-hydroxyethyl acrylate or methacrylate, and a methacrylic acid ester; and a polyfunctional urethane (meth)acrylate compound synthesized from a diisocyanate, a polyhydric alcohol, and a hydroxy ester of an acrylic acid or methacrylic acid. In addition to these, a polyether resin, a polyester resin, an epoxy resin, an alkyd resin, a spiroacetal resin, a polybutadiene resin, a polythiol-polyene resin and the like, all of which have acrylate-based functional groups, can also be used.

The resin member of the present invention can be used in all applications where synthetic resins are used, and without any particular limitations, the resin member can be particularly suitably used for applications with a possibility for exposure to light including sunlight or ultraviolet ray. Examples of the applications include coating agents or protective agents for glass substrate (the glass substrate including glass substitutes, window panes, lighting glass, and light source protecting glass); members for light sources emitting ultraviolet ray, such as a fluorescent lamp and a mercury lamp; containers or packaging materials for foods and medicines; and discoloration preventing agents for agricultural and industrial sheets, printed matter, dyed goods, dyes and pigments, signboards, signal lamps, and cards.

Among them, the resin member of the present invention is particularly suitable for optical material, among others, a film or member having a functional optical layer, and an optical molded article, from the viewpoint of enabling imparting of ultraviolet absorbency or a high refractive index while maintaining transparency of the matrix.

The film or member having a functional optical layer may be a single layer film, a multilayer film or an optical layer-attached substrate in which a single-layered or multi-layered optical layer intended for various applications is provided on a base material film or substrate. In a case in which a multilayered optical layer is provided, the resin member of the present invention is used in at least one of the layers.

In regard to the film or member having a functional optical layer, the optical film may be a base material film provided with functional layers intended for various applications, and examples thereof include various optical disc substrate protective film, a reflective film, an antireflective film, an oriented film, a polarizing film, a polarizing layer protective film, a retardation film, a light diffusing film, a viewing angle increasing film, an electromagnetic wave shielding film, an antiflare film, a light-shielding film, and a brightness increasing film.

Examples of the member having a functional optical layer include members obtained by laminating a single layer or multiple layers of at least any one of an antireflective layer, a hard coat layer, an antistatic layer, an adhesion stabilizing layer, a protective layer, an electromagnetic wave shielding layer and an infrared cutting layer on the surface of a panel substrate or the like.

Furthermore, the resin member of the present invention is suitable for a solar cell surface protective film. A solar cell element usually has a configuration in which an active layer working as a solar cell is provided between a pair of substrates; however, a flexible solar cell needs an ultraviolet-absorbing protective film because a polyester material for a gas barrier film, which is used as a member of the solar cell, or an active layer itself in an organic solar cell absorbs ultraviolet ray and is deteriorated. Furthermore, since solar cells are installed outdoors for a long period of time, such a protective film is required to have high weather resistance. Furthermore, since a solar cell absorbs light energy and converts the light energy to electric power, such a protective film is required to have high transparency. That is, a protective film for protecting a flexible solar cell is required to have high transparency, high ultraviolet absorbency, high weather resistance, and flexibility, and the resin member of the present invention is adequate for such an application.

The resin member of the present invention can be suitably used for optical molded articles such as lens elements for glasses lens plastics; optical lenses such as contact lenses, optical pickup lenses, camera lenses, and lenticular lenses; optical substrates such as prisms, filters, substrates for touch panels, and light-guiding plates; optical fibers, and optical molded articles such as information recording media. Regarding optical lenses, the resin member of the present invention is also suitable for plastic lenses such as lens films such as a Fresnel screen film and a lenticular lens film; or a microlens array using microlenses having a several micrometer-sized minute diameter, which are used for the purpose of increasing light collecting properties or light diffusibility in miniaturized optical functional elements, or for the purpose of collecting light in an image-capturing element or a light-receiving element.

Furthermore, the resin member of the present invention is also suitable for display substrates, for example, substrates for flat panel displays such as liquid crystal displays, organic EL displays, plasma displays, field emission displays, and electronic papers; and substrates for backlights of liquid crystal displays, signals, and neon signs.

In a case in which ultraviolet ray having wavelengths in a wide range is absorbed by a resin member such as a film, it is necessary to use multiple additives, to add an additive at a high concentration, or to make the film or resin thicker. However, in this case, it is likely to have problems in view of transparency and coloration. However, a triazine-based compound obtained by introducing one thioether group, which is used as an additive of the present invention, has an ultraviolet absorption band in a long wavelength region of 360 to 400 nm and in a short wavelength ultraviolet region of 260 to 280 nm, and enables ultraviolet absorption in a wider range. Thus, ultraviolet ray having wavelengths in a wide range can be absorbed by a single additive in low concentrations.

For example, it is desirable for a light-shielding film to be capable of cutting ultraviolet ray up to 360 to 400 nm; however, general additives cut light up to 450 to 500 nm (visible range) and thereby have a problem of attenuating visible light or being discolored. However, an additive of the present invention obtained by introducing a thioether group (i-2, iv-2) into a benzotriazole group of a benzotriazole-based compound or into a triazine-based compound, is capable of cutting ultraviolet ray having a longer wavelength of 360 to 400 nm even in the range of 315 to 400 nm (UV-A region), without cutting 450 to 500 nm (visible range). Thus, the additive of the present invention is highly useful.

The additive of the present invention that is obtained by introducing a thioether group of (i-2) into the phenyl group on a nitrogen atom of a benzotriazole-based compound, and has an ultraviolet absorption peak top near 290 nm in a short wavelength region, can efficiently prevent deterioration in, for example, a resin that is deteriorated at wavelengths in the vicinity of 290 to 300 nm, such as polyethylene, polymethyl methacrylate, or polycarbonate.

Furthermore, the additives of the present invention can be used not only in films and resin members but also in, for example, dyes, pigments, coloring materials, inks, paints, pharmaceutical products, surface coatings, cosmetics, photographic materials, and fabrics, which are required to be stabilized and functionalized by ultraviolet absorbers while having the above-described functions.

EXAMPLES

Hereinafter, the present invention will be described in more detail by way of Examples; however, the present invention is not intended to be limited to these Examples.

<Synthesis Example 1> Synthesis of Intermediate 1

(Intermediate 1)

Dibromohexane (50.0 g, 204.9 mmol) and S-potassium thioacetate (10.6 g, 102.5 mmol) were heated to reflux for 6 hours in 150 mL of acetonitrile. After completion of the reaction, a solid thus produced was separated by filtration, and the solvent was distilled off from the filtrate. Thus, a liquid crude product was obtained. Then, the crude product was purified using a column, and thereby Intermediate 1 was obtained as a transparent liquid.

<Synthesis Example 2> Synthesis of Intermediate 2

(Intermediate 2)

Dibromodecane (50.0 g, 166.6 mmol) and S-potassium thioacetate (8.6 g, 83.3 mmol) were heated to reflux for 6 hours in 150 mL of acetonitrile. After completion of the reaction, a solid thus produced was separated by filtration, and the solvent was distilled off from the filtrate. Thus, a liquid crude product was obtained. Then, the crude product was purified using a column, and thereby Intermediate 2 was obtained as a transparent liquid.

<Synthesis Example 3> Synthesis of Intermediate 3

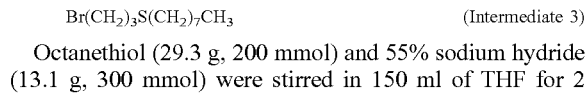

(Intermediate 3)

Octanethiol (29.3 g, 200 mmol) and 55% sodium hydride (13.1 g, 300 mmol) were stirred in 150 ml of THF for 2 hours under ice cooling, and then a suspension solution thus obtained was added dropwise to 100 mL of a THF solution of dibromopropane (121.1 g, 600 mmol) under ice cooling. The mixture was allowed to react for 2 hours. Toluene was added thereto, the mixture was washed with water, and then the resultant was subjected to distillation under reduced pressure. Thus, Intermediate 3 was obtained.

<Synthesis Example 4> Synthesis of Intermediate 4

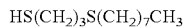  (Intermediate 4)

Intermediate 3 (7.5 g, 28.2 mmol) and S-potassium thioacetate (3.4 g, 29.6 mmol) were heated to reflux for 6 hours in 100 mL of acetonitrile. After completion of the reaction, a solid thus produced was separated by filtration, and the solvent was distilled off from the filtrate. Thus, a liquid compound was obtained. The compound thus obtained and an ethanol (100 mL) solution of sodium hydroxide (2.2 g, 55.6 mmol) were heated to reflux for 6 hours, and then the mixture was cooled to room temperature and was acidified using hydrochloric acid. Toluene was added to the reaction liquid, and the mixture was subjected to washing with water, solvent distillation, and purification with a column. Thus, Intermediate 4 was obtained as a liquid.

<Synthesis Example 5> Synthesis of Intermediate 5

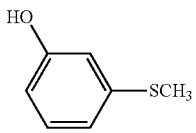  (Intermediate 5)

Hydroxybenzenethiol (10.0 g, 79.2 mmol), iodomethane (10.7 g, 75.2 mmol), and potassium carbonate (13.4 g, 96.9 mmol) were heated to reflux for 6 hours in 150 mL of acetonitrile. After completion of the reaction, toluene was added to the reaction liquid, and the mixture was subjected to washing with water, distillation of the solvent, and purification using a column. Thus, Intermediate 5 was obtained as a liquid.

<Synthesis Example 6> Synthesis of Intermediate 6

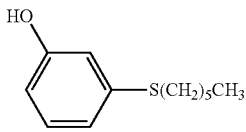  (Intermediate 6)

Hydroxybenzenethiol (15.0 g, 118.8 mmol), bromohexane (18.63 g, 112.8 mmol), and potassium carbonate (24.6 g, 178.2 mmol) were heated to reflux for 6 hours in 150 mL of acetonitrile. After completion of the reaction, toluene was added to the reaction liquid, and the mixture was subjected to washing with water, distillation of the solvent, and purification using a column. Thus, Intermediate 6 was obtained as a liquid.

<Synthesis Example 7> Synthesis of Intermediate 7

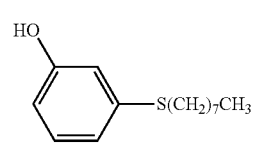  (Intermediate 7)

Hydroxybenzenethiol (10.0 g, 79.2 mmol), bromooctane (14.6 g, 75.6 mmol), and potassium carbonate (13.4 g, 96.9 mmol) were heated to reflux for 6 hours in 150 mL of acetonitrile. After completion of the reaction, toluene was added to the reaction liquid, and the mixture was subjected to washing with water, distillation of the solvent, and purification using a column. Thus, Intermediate 7 was obtained as a liquid.

<Synthesis Example 8> Synthesis of Intermediate 8

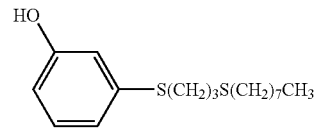  (Intermediate 8)

Hydroxybenzenethiol (10.0 g, 79.2 mmol), Intermediate 3 (20.2 g, 75.6 mmol), and potassium carbonate (13.4 g, 96.9 mmol) were heated to reflux for 6 hours in 150 mL of acetonitrile. After completion of the reaction, toluene was added to the reaction liquid, and the mixture was subjected to washing with water, distillation of the solvent, and purification using a column. Thus, Intermediate 8 was obtained as a liquid.

<Synthesis Example 9> Synthesis of Compound 1

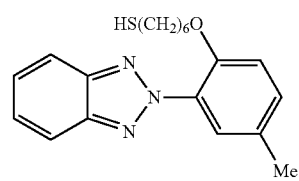  (Compound 1)

2-(2-Hydroxy-5-methylphenyl)benzotriazole (10.0 g, 44.4 mmol), Intermediate 1 (11.6 g, 48.8 mmol), and potassium carbonate (12.3 g, 88.8 mmol) were heated to reflux for 6 hours in 100 mL of acetonitrile. After completion of the reaction, toluene was added to the reaction liquid, and the mixture was subjected to washing with water, distillation of the solvent, and purification using a column. Thus, Intermediate 9 as described below was obtained as a liquid.

(Intermediate 9)

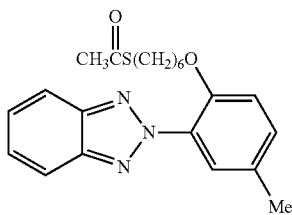

Intermediate 9 (5.0 g, 13.1 mmol) and an ethanol (100 mL) solution of sodium hydroxide (1.0 g, 26.1 mmol) were heated to reflux for 6 hours, and then the mixture was cooled to room temperature and was acidified using hydrochloric acid. Toluene was added to the reaction liquid, and the mixture was subjected to washing with water, distillation of the solvent, and purification using a column. Thus, Compound 1 was obtained as a liquid.

FT-IR (KBr): 2550 cm$^{-1}$: S—H stretching vibration, 1464, 1403 cm$^{-1}$: triazole ring stretching vibration, 1073 cm$^{-1}$: —O—CH$_2$ antisymmetric stretching vibration $^1$H-NMR (CDCl$_3$ 400 MHz): δ 1.24 (m, 5H, O—(CH$_2$)$_2$C$\underline{H}_2$ C$\underline{H}_2$(CH$_2$)$_2$—S$\underline{H}$), 1.43 (m, 2H, O—(CH$_2$)$_4$C$\underline{H}_2$CH$_2$—SH), 1.63 (m, 2H, O—CH$_2$C$\underline{H}_2$(CH$_2$)$_4$—SH), 2.34 (m, 5H, O—(CH$_2$)$_5$C$\underline{H}_2$—SH, -Ph-C$\underline{H}_3$—O—), 3.99 (tri, 2H, O—C$\underline{H}_2$(CH$_2$)$_5$—SH), 7.00 (d, 1H), 7.24 (d, 1H), 7.42 (m, 2H), 7.47 (s, 1H), 7.97 (m, 2H) (insg.7arom. C$\underline{H}$)

$^{13}$C-NMR (CDCl$_3$ 400 MHz): δ20.0 (C$_{arom}$—$\underline{C}$H$_3$), 24.4 (O—(CH$_2$)$_5$$\underline{C}$H$_2$—SH), 25.4 (O—(CH$_2$)$_2$ $\underline{C}$H$_2$(CH$_2$)$_3$—SH), 27.8 (O—(CH$_2$)$_3$$\underline{C}$H$_2$(CH$_2$)$_2$—SH), 28.8 (O—CH$_2$ $\underline{C}$H$_2$(CH$_2$)$_4$—SH), 33.8 (O—(CH$_2$)$_4$ $\underline{C}$H$_2$ CH$_2$—SH), 69.6 (O—$\underline{C}$H$_2$(CH$_2$)$_5$—SH), 117.6, 127.7, 129.6, 131.5 ($\underline{C}$H$_{arom}$), 114.5, 147.5 ($\underline{C}_{arom}$), 130.5 ($\underline{C}_{arom}$—CH$_3$), 151.0 ($\underline{C}_{arom}$O—)

<Synthesis Example 10> Synthesis of Compound 2

(Compound 2)

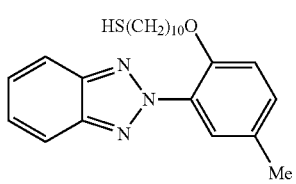

Compound 2 was synthesized by a synthesis method similar to that used for Compound 1, using Intermediate 2 (14.3 g, 48.8 mmol). The properties values are shown below.

FT-IR (KBr): 2559 cm$^{-1}$: S—H stretching vibration, 1465, 1403 cm$^{-1}$: triazole ring stretching vibration, 1073 cm$^{-1}$: —O—CH$_2$ antisymmetric stretching vibration $^1$H-NMR (CDCl$_3$ 400 MHz): δ 1.18 (m, 10H, O—(CH$_2$)$_3$ (C$\underline{H}_2$)$_5$(CH$_2$)$_2$—SH), 1.32 (m, 3H, O—(CH$_2$)$_2$C$\underline{H}_2$ (CH$_2$)$_7$—S$\underline{H}$), 1.60 (m, 4H, O—CH$_2$C$\underline{H}_2$(CH$_2$)$_6$C$\underline{H}_2$CH$_2$SH), 2.37 (s, 3H, -Ph-C$\underline{H}_3$—O—), 2.50 (quin, 2H, O—(CH$_2$)$_9$C$\underline{H}_2$SH), 4.00 (tri, 2H, O—C$\underline{H}_2$(CH$_2$)$_9$SH), 7.03 (d, 1H), 7.25 (d, 1H), 7.42 (m, 2H), 7.47 (s, 1H), 7.97 (m, 2H) (insg.7arom. C$\underline{H}$)

$^{13}$C-NMR (CDCl$_3$ 400 MHz): δ20.0 (C$_{arom}$—$\underline{C}$H$_3$), 24.6 (O—(CH$_2$)$_9$$\underline{C}$H$_2$—SH), 25.7 (O—(CH$_2$)$_2$ $\underline{C}$H$_2$(CH$_2$)$_7$—SH), 28.3 (O—(CH$_2$)$_3$$\underline{C}$H$_2$(CH$_2$)$_6$—SH), 28.9 (O—(CH$_2$)$_4$$\underline{C}$H$_2$(CH$_2$)$_5$—SH), 29.0 (O—(CH$_2$)$_5$ $\underline{C}$H$_2$(CH$_2$)$_4$—SH), 29.1 (O—(CH$_2$)$_6$$\underline{C}$H$_2$(CH$_2$)$_3$—SH), 29.2 (O—(CH$_2$)$_7$$\underline{C}$H$_2$(CH$_2$)$_2$—SH), 29.4 (O—(CH$_2$)$_8$ $\underline{C}$H$_2$CH$_2$—S$\underline{H}$), 34.0 (O—CH$_2$$\underline{C}$H$_2$(CH$_2$)$_8$—SH), 69.6 (O—$\underline{C}$H$_2$(CH$_2$)$_9$—SH), 117.6, 127.7, 129.6, 131.5 ($\underline{C}$H$_{arom}$), 114.5, 147.5 ($\underline{C}_{arom}$), 130.5 ($\underline{C}_{arom}$—CH$_3$), 151.0 ($\underline{C}_{arom}$O—)

<Synthesis Example 11> Synthesis of Compound 3

(Compound 3)

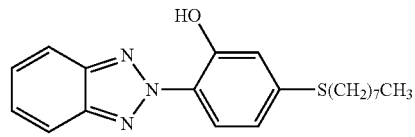

Concentrated hydrochloric acid (11 ml, 0.13 mol) was added to an aqueous solution (100 mL) of nitroaniline (2.64 g, 19.1 mmol), and then an aqueous solution (15 mL) of sodium nitrite (2.64 g, 19.1 mmol) was added dropwise thereto for 30 minutes under ice cooling. The mixture was allowed to react for 30 minutes, and thereby a diazonium salt of an intermediate was obtained. Next, an aqueous solution of the aforementioned diazonium salt was added dropwise to an aqueous solution (150 mL) obtained by mixing Intermediate 7 (5.0 g, 20.1 mmol) with sodium hydroxide (0.96 g, 23.9 mmol) for one hour under ice cooling, and the mixture was allowed to react for one hour. After completion of the reaction, the reaction mixture was acidified with hydrochloric acid, toluene was added thereto, and the mixture was washed with water. Subsequently, the solvent was distilled off, and the residue was subjected to recrystallization. Thus, Intermediate 10 as described below was obtained.

(Intermediate 10)

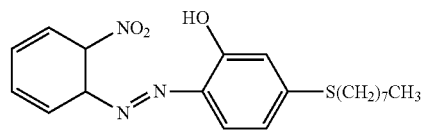

Intermediate 10 (4.50 g, 9.7 mmol), a 1.2% aqueous solution of hydrazine (50 ml), and sodium hydroxide (1.73 g, 34.13 mmol) were reacted for 12 hours in toluene (100 mL) while the mixture was heated to reflux. The reaction mixture was cooled to room temperature, subsequently the reaction mixture was washed with water, and the solvent was distilled off. Thus, a liquid intermediate was obtained. That intermediate, concentrated sulfuric acid (0.78 mL), and zinc (3.04 g, 46.5 mmol) were reacted for 12 hours in toluene (100 mL), while the mixture was heated to reflux. Subsequently, the reaction liquid was subjected to washing with water, distillation of the solvent, and purification using a column, and thus Compound 3 was obtained as a liquid.

FT-IR (KBr): 3270 cm$^{-1}$: O—H stretching vibration, 1437, 1411 cm$^{-1}$: triazole ring stretching vibration, 660 cm$^{-1}$: C—S stretching vibration $^1$H-NMR (CDCl$_3$ 400 MHz): δ 0.83 (t, 3H, C$\underline{H}_3$(CH$_2$)$_7$—S), 1.27 (m, 10H, CH$_3$ (C$\underline{H}_2$)$_5$(CH$_2$)$_2$—S), 1.54 (quin, 2H, CH$_3$ (CH$_2$)$_5$C$\underline{H}_2$CH$_2$—S), 2.79 (t, 2H, CH$_3$ (CH$_2$)$_6$C$\underline{H}_2$—S), 6.40 (s, 1H, Ph-O$\underline{H}$), 6.70 (d, 1H), 6.91 (s, 1H), 7.46 (m, 2H), 7.51 (d, 1H), 7.98 (m, 2H) (insg.7arom. C$\underline{H}$)

$^{13}$C-NMR (CDCl$_3$ 400 MHz): δ 13.0 (CH$_3$(CH$_2$)$_7$—S), 21.6 (CH$_3$ CH$_2$(CH$_2$)$_6$—S), 28.0 (CH$_3$CH$_2$ (CH$_2$)$_4$ (CH$_2$)$_2$—S), 30.7 (CH$_3$(CH$_2$)$_5$CH$_2$CH$_2$—S), 32.0 (CH$_3$(CH$_2$)$_5$CH$_2$ CH$_2$—S), 111.6, 113.6, 117.3, 126.1, 126.9, 135.4 (CH$_{arom}$), 131.3 (C$_{arom}$—S), 143.5 (C$_{arom}$), 156.4 (C$_{arom}$OH)

<Synthesis Example 12> Synthesis of Compound 4

(Compound 4)

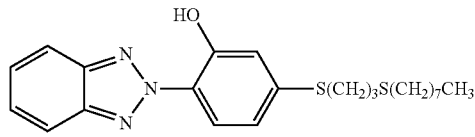

Compound 4 was synthesized by a synthesis method similar to that used for Compound 3, using Intermediate 8 (5.7 g, 20.1 mmol). The properties values are shown below.

FT-IR (KBr): 3059 cm$^{-1}$: O—H stretching vibration, 1437, 1399 cm$^{-1}$: triazole ring stretching vibration, 669 cm$^{-1}$: C—S stretching vibration $^1$H-NMR (CDCl$_3$ 400 MHz): δ 0.87 (t, 3H, CH$_3$(CH$_2$)$_7$—S), 1.25 (m, 10H, CH$_3$(CH$_2$)$_5$(CH$_2$)$_2$—S), 1.53 (quin, 2H, CH$_3$(CH$_2$)$_5$CH$_2$CH$_2$—S), 1.86 (quin, 2H, S—CH$_2$CH$_2$CH$_2$—S-Ph), 2.43 (t, 2H, CH$_3$(CH$_2$)$_6$CH$_2$—S), 2.54 (t, 2H, S—CH$_2$CH$_2$CH$_2$—S-Ph), 2.96 (t, 2H, S—CH$_2$CH$_2$CH$_2$—S-Ph), 5.95 (s, 1H, Ph-OH), 6.74 (d, 1H), 6.97 (s, 1H), 7.44 (m, 2H), 7.57 (d, 1H), 7.98 (m, 2H) (insg.7arom. CH)

$^{13}$C-NMR (CDCl$_3$ 400 MHz): δ14.1 (CH$_3$(CH$_2$)$_7$—S), 22.6 (CH$_3$CH$_2$(CH$_2$)$_6$—S), 28.2 (CH$_3$(CH$_2$)$_2$CH$_2$(CH$_2$)$_4$—S), 28.9 (CH$_3$(CH$_2$)$_5$CH$_2$CH$_2$—S), 29.2 (CH$_3$(CH$_2$)$_3$CH$_2$CH$_2$(CH$_2$)$_2$—S), 29.6 (CH$_3$(CH$_2$)$_6$CH$_2$—S), 30.9 (S—CH$_2$CH$_2$CH$_2$—S), 31.8 (CH$_3$CH$_2$CH$_2$(CH$_2$)$_5$—S), 32.1 (S—CH$_2$CH$_2$CH$_2$—S), 112.9, 114.8, 118.4, 128.0, 135.7 (C$_{arom}$H), 127.0 (C$_{arom}$—N), 144.6 (C$_{arom}$), 134.1 (C$_{arom}$—S), 156.9 (C$_{arom}$—OH)

<Synthesis Example 13> Synthesis of Compound 6

(Compound 6)

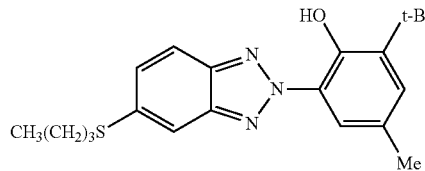

2-(2-Hydroxy-3-tert-butyl-5-methylphenyl)-5-chlorobenzotriazole (60.0 g, 0.190 mol), butanethiol (34.3 g, 0.380 mol), potassium carbonate (57.8 g, 0.418 mol), and potassium iodide (2.21 g, 0.013 mol) were allowed to react for 12 hours at 125° C. in 150 g of DMF. After completion of the reaction, the pH was adjusted, subsequently the reaction liquid was subjected to filtration, washing with MeOH, and washing with water, and recrystallization was performed. Thus, Compound 6 was obtained.

FT-IR (KBr): 3000 cm$^{-1}$: O—H stretching vibration, 1445, 1392 cm$^{-1}$: triazole ring stretching vibration, 661 cm$^{-1}$: C—S stretching vibration $^1$H-NMR (CDCl$_3$ 400 MHz): δ 0.96 (t, 3H, CH$_3$(CH$_2$)$_3$—S), 1.49 (m, 11H, -Ph-OH—CH$_3$—C(CH$_3$)$_3$, CH$_3$CH$_2$CH$_2$CH$_2$—S), 1.75 (quin, 2H, CH$_3$ CH$_2$ CH$_2$ CH$_2$—S), 2.38 (s, 3H, -Ph-OH—CH$_3$—C(CH$_3$)$_3$), 3.03 (t, 2H, CH$_3$CH$_2$CH$_2$CH$_2$—S), 7.16 (s, 1H), 7.37 (d, 1H), 7.70 (s, 1H), 7.81 (d, 1H), 8.05 (d, 1H), (insg.5arom. CH), 11.61 (s, 1H, -Ph-OH—CH$_3$—C(CH$_3$)$_3$)

$^{13}$C-NMR (CDCl$_3$ 400 MHz): δ 13.7 (CH$_3$(CH$_2$)$_3$—S), 20.9 (-Ph-OH—CH$_3$—C(CH$_3$)$_3$), 22.1 (CH$_3$CH$_2$CH$_2$CH$_2$—S), 29.5 (-Ph-OH—CH$_3$—C(CH$_3$)$_3$), 30.8 (-Ph-OH—CH$_3$—C(CH$_3$)$_3$), 32.8 (CH$_3$CH$_2$CH$_2$CH$_2$—S), 35.4 (CH$_3$CH$_2$CH$_2$CH$_2$—S), 113.6, 117.5, 119.3, 128.7, 129.3 (CH$_{arom}$), 125.4, 141.2, 143.4 (C$_{arom}$), 128.3 (C$_{arom}$—CH$_3$), 138.0 (C$_{arom}$—S), 139.1 (C$_{arom}$—C(CH$_3$)$_3$), 146.7 (C$_{arom}$—OH)

<Synthesis Example 14> Synthesis of Compound 7

(Compound 7)

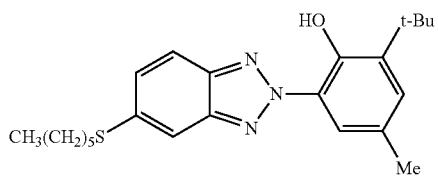

2-(2-Hydroxy-3-tert-butyl-5-methylphenyl)-5-chlorobenzotriazole (50.0 g, 0.158 mol), hexanethiol (37.4 g, 0.316 mol), potassium carbonate (48.1 g, 0.348 mol), and potassium iodide (1.8 g, 0.011 mol) were allowed to react for 12 hours at 125° C. in 125 g of DMF. After completion of the reaction, the pH was adjusted, subsequently the reaction liquid was subjected to filtration, washing with MeOH, and washing with water, and recrystallization was performed. Thus, Compound 7 was obtained.

FT-IR (KBr): 2956 cm$^{-1}$: O—H stretching vibration, 1445, 1392 cm$^{-1}$: triazole ring stretching vibration, 662 cm$^{-1}$: C—S stretching vibration $^1$H-NMR (CDCl$_3$ 400 MHz): δ 0.89 (t, 3H, CH$_3$(CH$_2$)$_5$—S), 1.33 (m, 4H, CH$_3$(CH$_2$)$_2$(CH$_2$)$_3$—S), 1.49 (m, 11H, -Ph-OH—CH$_3$—C(CH$_3$)$_3$, CH$_3$(CH$_2$)$_2$ CH$_2$(CH$_2$)$_2$—S), 1.73 (quin, 2H, CH$_3$ (CH$_2$)$_3$ CH$_2$CH$_2$—S), 2.38 (s, 3H, -Ph-OH—CH$_3$—C(CH$_3$)$_3$), 3.02 (t, 2H, CH$_3$ (CH$_2$)$_3$CH$_2$CH$_2$—S), 7.16 (s, 1H), 7.36 (d, 1H), 7.69 (s, 1H), 7.78 (d, 1H), 8.04 (s, 1H), (insg.5arom. CH), 11.62 (s, 1H, -Ph-OH—CH$_3$—C(CH$_3$)$_3$)

$^{13}$C-NMR (CDCl$_3$ 400 MHz): δ 14.0 (CH$_3$(CH$_2$)$_5$—S), 20.9 (-Ph-OH—CH$_3$—C(CH$_3$)$_3$), 22.6 (CH$_3$CH$_2$(CH$_2$)$_3$CH$_2$—S), 28.7 (CH$_3$ CH$_2$ (CH$_2$)$_2$ CH$_2$CH$_2$—S), 29.5 (-Ph-OH—CH$_3$—C(CH$_3$)$_3$), 31.8 (-Ph-OH—CH$_3$—C(CH$_3$)$_3$), 33.8 (CH$_3$(CH$_2$)$_3$CH$_2$CH$_2$—S), 35.4 (CH$_3$(CH$_2$)$_3$CH$_2$CH$_2$—S), 113.6, 117.5, 119.3, 128.7, 129.2 (CH$_{arom}$), 125.4, 141.2, 143.4 (C$_{arom}$), 128.3 (C$_{arom}$—CH$_3$), 138.0 (C$_{arom}$—S), 139.1 (C$_{arom}$—C(CH$_3$)$_3$), 146.7 (C$_{arom}$—OH)

<Synthesis Example 15> Synthesis of Compound 8

(Compound 8)

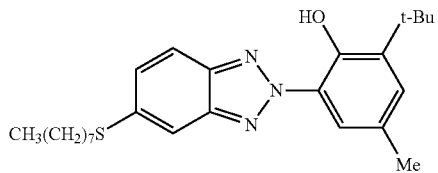

2-(2-Hydroxy-3-tert-butyl-5-methylphenyl)-5-chlorobenzotriazole (5.00 g, 15.8 mmol), octanethiol (7.63 g, 52.1 mmol), potassium carbonate (7.20 g, 52.1 mmol), and potassium iodide (0.18 g, 1.1 mmol) were allowed to react for 20 hours at 150° C. in 50 m of DMF. After completion of the reaction, toluene was added thereto, and the mixture was subjected to washing with water, distillation of the solvent, and purification using a column. Thus, Compound 8 was obtained.

FT-IR (KBr): 3125 cm$^{-1}$: O—H stretching vibration, 1438, 1391 cm$^{-1}$: triazole ring stretching vibration, 661 cm$^{-1}$: C—S stretching vibration $^1$H-NMR (CDCl$_3$ 400 MHz): δ 0.88 (t, 3H, C$\underline{H}_3$(CH$_2$)$_7$—S), 1.27 (m, 8H, CH$_3$ (C$\underline{H}_2$)$_4$(CH$_2$)$_3$—S), 1.49 (m, 11H, -Ph-OH—CH$_3$—C(C$\underline{H}_3$)$_3$, CH$_3$(CH$_2$)$_4$ C$\underline{H}_2$(CH$_2$)$_2$—S), 1.75 (quin, 2H, CH$_3$ (CH$_2$)$_5$ C$\underline{H}_2$CH$_2$—S), 2.38 (s, 3H, -Ph-OH—C$\underline{H}_3$—C(CH$_3$)$_3$), 3.03 (t, 2H, CH$_3$ (CH$_2$)$_5$CH$_2$C$\underline{H}_2$—S), 7.16 (s, 1H), 7.37 (d, 1H), 7.70 (s, 1H), 7.81 (d, 1H), 8.05 (s, 1H), (insg.5arom. C$\underline{H}$), 11.61 (s, 1H, -Ph-O$\underline{H}$—CH$_3$—C(CH$_3$)$_3$)

$^{13}$C-NMR (CDCl$_3$ 400 MHz): δ 14.0 ($\underline{C}$H$_3$(CH$_2$)$_7$—S), 20.0 (-Ph-OH—$\underline{C}$H$_3$—C(CH$_3$)$_3$), 22.6 (-Ph-OH—CH$_3$—$\underline{C}$(CH$_3$)$_3$), 28.7 (CH$_3$($\underline{C}$H$_2$)$_5$CH$_2$ CH$_2$—S), 31.9 (-Ph-OH—CH$_3$—C($\underline{C}$H$_3$)$_3$), 33.2 (CH$_3$(CH$_2$)$_5$$\underline{C}$H$_2$CH$_2$—S), 35.4 (CH$_3$(CH$_2$)$_5$CH$_2$$\underline{C}$H$_2$—S), 113.6, 117.5, 119.3, 128.7, 129.3 ($\underline{C}$H$_{arom}$), 141.2, 143.4 ($\underline{C}_{arom}$), 125.4 ($\underline{C}_{arom}$—N), 128.3 ($\underline{C}_{arom}$—$\underline{C}$H$_3$), 138.0 ($\underline{C}_{arom}$—S), 139.1 ($\underline{C}_{arom}$—C(CH$_3$)$_3$), 146.7 ($\underline{C}_{arom}$—OH)

<Synthesis Example 16> Synthesis of Compound 9

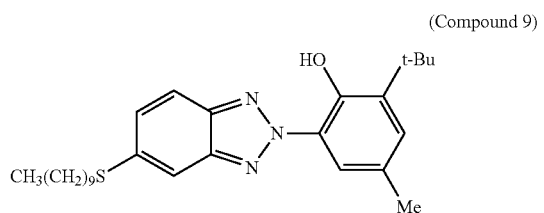

(Compound 9)

2-(2-Hydroxy-3-tert-butyl-5-methylphenyl)-5-chlorobenzotriazole (50.0 g, 0.158 mol), decanol (55.2 g, 0.317 mol), potassium carbonate (48.1 g, 0.348 mol), and potassium iodide (1.8 g, 0.011 mol) were allowed to react for 12 hours at 125° C. in 125 g of DMF. After completion of the reaction, the pH was adjusted, subsequently the reaction liquid was subjected to filtration, washing with MeOH, and washing with water, and recrystallization was performed. Thus, Compound 9 was obtained.

FT-IR (KBr): 2958 cm$^{-1}$: O—H stretching vibration, 1448, 1392 cm$^{-1}$: triazole ring stretching vibration, 641 cm$^{-1}$: C—S stretching vibration $^1$H-NMR (CDCl$_3$ 400 MHz): δ 0.89 (t, 3H, C$\underline{H}_3$(CH$_2$)$_9$—S), 1.26 (m, 12H, CH$_3$ (C$\underline{H}_2$)$_6$(CH$_2$)$_3$—S), 1.49 (m, 11H, -Ph-OH—CH$_3$—C(C$\underline{H}_3$)$_3$, CH$_3$(CH$_2$)$_6$ C$\underline{H}_2$(CH$_2$)$_2$—S), 1.74 (quin, 2H, CH$_3$ (CH$_2$)$_7$ C$\underline{H}_2$CH$_2$—S), 2.38 (s, 3H, -Ph-OH—C$\underline{H}_3$—C(CH$_3$)$_3$), 3.03 (t, 2H, CH$_3$ (CH$_2$)$_7$CH$_2$C$\underline{H}_2$—S), 7.16 (s, 1H), 7.36 (d, 1H), 7.69 (s, 1H), 7.78 (d, 1H), 8.05 (s, 1H), (insg.5arom. C$\underline{H}$), 11.62 (s, 1H, -Ph-O$\underline{H}$—CH$_3$—C(CH$_3$)$_3$)

$^{13}$C-NMR (CDCl$_3$ 400 MHz): δ 14.0 ($\underline{C}$H$_3$(CH$_2$)$_9$—S), 20.9 (-Ph-OH—$\underline{C}$H$_3$—C(CH$_3$)$_3$), 22.7 (CH$_3$ $\underline{C}$H$_2$(CH$_2$)$_7$CH$_2$—S), 28.7~29.5 (CH$_3$ CH$_2$ ($\underline{C}$H$_2$)$_6$ CH$_2$CH$_2$—S), 29.6 (-Ph-OH—CH$_3$—C($\underline{C}$H$_3$)$_3$), 31.9 (-Ph-OH—CH$_3$—$\underline{C}$(CH$_3$)$_3$), 33.1 (CH$_3$(CH$_2$)$_7$$\underline{C}$H$_2$CH$_2$—S), 35.4 (CH$_3$(CH$_2$)$_7$CH$_2$$\underline{C}$H$_2$—S), 113.6, 117.5, 119.3, 128.7, 129.3 ($\underline{C}$H$_{arom}$), 125.4, 141.2, 143.4 ($\underline{C}_{arom}$), 128.3 ($\underline{C}_{arom}$—CH$_3$), 138.0 ($\underline{C}_{arom}$—S), 139.1 ($\underline{C}_{arom}$—C(CH$_3$)$_3$), 146.7 ($\underline{C}_{arom}$—OH)

<Synthesis Example 17> Synthesis of Compound 10

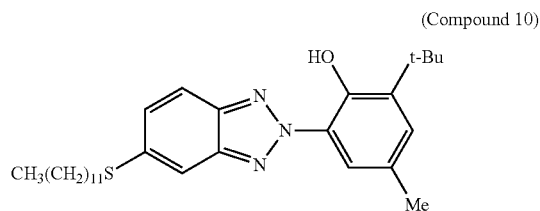

(Compound 10)

Compound 10 was synthesized by a synthesis method similar to that used for Compound 8, using dodecanethiol (10.5 g, 52.1 mmol) instead of octanethiol. The properties values are shown below.

FT-IR (KBr): 3009 cm$^{-1}$: O—H stretching vibration, 1441, 1390 cm$^{-1}$: triazole ring stretching vibration, 662 cm$^{-1}$: C—S stretching vibration $^1$H-NMR (CDCl$_3$ 400 MHz): δ 0.88 (t, 3H, C$\underline{H}_3$(CH$_2$)$_{11}$—S), 1.25 (m, 16H, CH$_3$ (C$\underline{H}_2$)$_8$(CH$_2$)$_3$—S), 1.49 (m, 11H, -Ph-OH—CH$_3$—C(C$\underline{H}_3$)$_3$, CH$_3$(CH$_2$)$_8$ C$\underline{H}_2$(CH$_2$)$_2$—S), 1.74 (quin, 2H, CH$_3$ (CH$_2$)$_9$ C$\underline{H}_2$CH$_2$—S), 2.38 (s, 3H, -Ph-OH—C$\underline{H}_3$—C(CH$_3$)$_3$), 3.03 (t, 2H, CH$_3$(CH$_2$)$_{10}$C$\underline{H}_2$—S), 7.16 (s, 1H), 7.37 (d, 1H), 7.70 (s, 1H), 7.81 (d, 1H), 8.05 (s, 1H) (insg.5arom. C$\underline{H}$), 11.61 (s, 1H, -Ph-O$\underline{H}$—CH$_3$—C(CH$_3$)$_3$)

$^{13}$C-NMR (CDCl$_3$ 400 MHz): δ 14.0 ($\underline{C}$H$_3$(CH$_2$)$_{11}$—S), 20.9 (-Ph-OH—$\underline{C}$H$_3$—C(CH$_3$)$_3$), 22.7 (-Ph-OH—CH$_3$—$\underline{C}$(CH$_3$)$_3$), 28.7~29.7 (CH$_3$($\underline{C}$H$_2$)$_9$CH$_2$CH$_2$—S), 31.9 (-Ph-OH—CH$_3$—C($\underline{C}$H$_3$)$_3$), 33.2 (CH$_3$(CH$_2$)$_9$$\underline{C}$H$_2$CH$_2$—S), 35.4 (CH$_3$(CH$_2$)$_9$CH$_2$$\underline{C}$H$_2$—S), 113.5, 117.5, 119.3, 128.6, 129.3 ($\underline{C}$H$_{arom}$), 141.2, 143.4 ($\underline{C}_{arom}$), 125.4 ($\underline{C}_{arom}$—N), 128.3 ($\underline{C}_{arom}$—$\underline{C}$H$_3$), 138.0 ($\underline{C}_{arom}$—S), 139.1 ($\underline{C}_{arom}$—C(CH$_3$)$_3$), 146.7 ($\underline{C}_{arom}$—OH)

<Synthesis Example 18> Synthesis of Compound 11

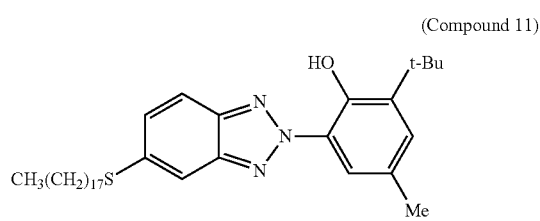

(Compound 11)

Compound 11 was synthesized by a synthesis method similar to that used for Compound 8, using octadecanethiol (14.9 g, 52.1 mmol) instead of octanethiol. The properties values are shown below.

FT-IR (KBr): 3059 cm$^{-1}$: O—H stretching vibration, 1445, 1391 cm$^{-1}$: triazole ring stretching vibration, 664 cm$^{-1}$: C—S stretching vibration $^1$H-NMR (CDCl$_3$ 400 MHz): δ 0.88 (t, 3H, C$\underline{H}_3$(CH$_2$)$_{17}$—S), 1.25 (m, 30H, CH$_3$(C$\underline{H}_2$)$_{15}$(CH$_2$)$_2$—S), 1.49 (s, 9H, -Ph-OH—CH$_3$—C(CH$_3$)$_3$, 1.74 (quin, 2H, CH$_3$(CH$_2$)$_{15}$C$\underline{H}_2$CH$_2$—S), 2.38 (s, 3H, -Ph-OH—C$\underline{H}_3$—C(CH$_3$)$_3$), 3.03 (t, 2H, CH$_3$(CH$_2$)$_{15}$CH$_2$C$\underline{H}_2$—S), 7.16 (s, 1H), 7.37 (d, 1H), 7.70 (s, 1H), 7.81 (d, 1H), 8.05 (s, 1H) (insg.5arom. C$\underline{H}$), 11.61 (s, 1H, -Ph-O$\underline{H}$—CH$_3$—C(CH$_3$)$_3$) $^{13}$C-NMR (CDCl$_3$ 400 MHz): δ 13.1 ($\underline{C}$H$_3$(CH$_2$)$_{17}$—S), 19.9 (-Ph-OH—$\underline{C}$H$_3$—C(CH$_3$)$_3$), 21.6 (-Ph-OH—CH$_3$—$\underline{C}$(CH$_3$)$_3$), 28.5 (CH$_3$($\underline{C}$H$_2$)$_{16}$CH$_2$—S), 30.6 (C$_{arom}$—(-Ph-OH—CH$_3$—C(CH$_3$)$_3$), 34.4 (CH$_3$(CH$_2$)$_{16}$$\underline{C}$H$_2$—S), 115.5, 117.6, 118.2, 127.2, 128.0 ($\underline{C}$H$_{arom}$), 141.9, 142.9 ($\underline{C}_{arom}$), 124.2 ($\underline{C}_{arom}$—N), 128.1 ($\underline{C}_{arom}$—$\underline{C}$H$_3$), 132.3 ($\underline{C}_{arom}$—S), 140.0 ($\underline{C}_{arom}$—C(CH$_3$)$_3$), 145.6 ($\underline{C}_{arom}$—OH)

<Synthesis Example 19> Synthesis of Compound 12

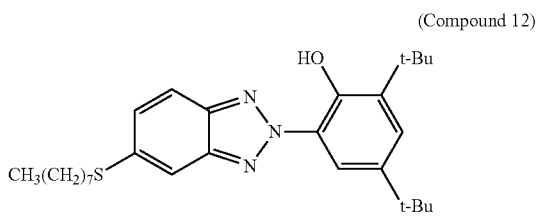

(Compound 12)

2-(3,5-Di-tert-butyl-2-hydroxyphenyl)-5-chlorobenzotriazole (25.0 g, 69.85 mmol), butanethiol (20.43 g, 139.71 mmol), potassium carbonate (21.23 g, 153.68 mmol), and potassium iodide (2.21 g, 4.82 mmol) were allowed to react for 12 hours at 125° C. in 150 g of DMF. After completion of the reaction, the pH was adjusted, and then the reaction liquid was subjected to filtration and washing with MeOH. Subsequently, the pH was adjusted again, the resultant was washed with water, and recrystallization was performed. Thus, Compound 12 was obtained.

FT-IR (KBr): 2953 cm$^{-1}$: O—H stretching vibration, 1439, 1392 cm$^{-1}$: triazole ring stretching vibration, 667 cm$^{-1}$: C—S stretching vibration $^1$H-NMR (CDCl$_3$400 MHz): δ 0.88 (t, 3H, C$\underline{H}_3$(CH$_2$)$_7$—S), 1.27 (m, 8H, CH$_3$ (C$\underline{H}_2$)$_4$(CH$_2$)$_3$—S), 1.39 (s, 9H, -Ph-OH—C(C$\underline{H}_3$)$_3$—C(CH$_3$)$_3$), 1.51 (m, 11H, -Ph-OH—C(CH$_3$)$_3$—C(C$\underline{H}_3$)$_3$, CH$_3$ (CH$_2$)$_2$ C$\underline{H}_2$(CH$_2$)$_2$—S), 1.75 (quin, 2H, CH$_3$ (CH$_2$)$_5$ C$\underline{H}_2$CH$_2$—S), 3.03 (t, 2H, CH$_3$ (CH$_2$)$_5$CH$_2$C$\underline{H}_2$—S), 7.37 (d, 1H), 7.40 (s, 1H), 7.71 (s, 1H), 7.82 (d, 1H), 8.24 (d, 1H), (insg.5arom. C$\underline{H}$), 11.66 (s, 1H, -Ph-O$\underline{H}$—C(CH$_3$)$_3$—C(CH$_3$)$_3$)

$^{13}$C-NMR (CDCl$_3$ 400 MHz): δ 14.1 ($\underline{C}$H$_3$(CH$_2$)$_7$—S), 22.6 (CH$_3$ $\underline{C}$H$_2$ (CH$_2$)$_6$—S), 28.7~29.2 (CH$_3$ CH$_2$ ($\underline{C}$H$_2$)$_4$ CH$_2$CH$_2$—S), 29.6 (-Ph-OH—C(CH$_3$)$_3$—C($\underline{C}$H$_3$)$_3$), 31.5 (-Ph-OH—C($\underline{C}$H$_3$)$_3$—C(CH$_3$)$_3$), 31.8 (CH$_3$ CH$_2$ (CH$_2$)$_4$ $\underline{C}$H$_2$CH$_2$—S), 33.2 (-Ph-OH—$\underline{C}$(CH$_3$)$_3$—C(CH$_3$)$_3$), 34.6 (CH$_3$(CH$_2$)$_4$CH$_2$$\underline{C}$H$_2$—S), 35.7 (-Ph-OH—C(CH$_3$)$_3$—$\underline{C}$(CH$_3$)$_3$), 113.6, 116.0, 117.6, 129.2, 143.4 ($\underline{C}$H$_{arom}$), 125.0, 141.2, 143.4 ($\underline{C}_{arom}$), 137.9 ($\underline{C}_{arom}$—S), 125.2, 138.6 ($\underline{C}_{arom}$—C(CH$_3$)$_3$), 146.6 ($\underline{C}_{arom}$—OH)

<Synthesis Example 20> Synthesis of Compound 13

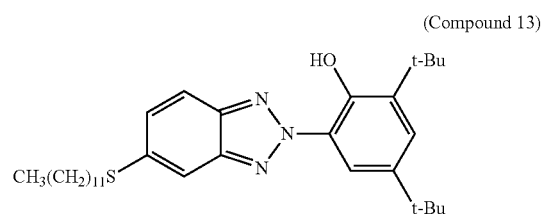

(Compound 13)

2-(3,5-D I-tert-butyl-2-hydroxyphenyl)-5-chlorobenzotriazole (25.0 g, 69.85 mmol), dodecanethiol (28.28 g, 139.72 mmol), potassium carbonate (21.24 g, 153.68 mmol), and potassium iodide (0.81 g, 4.88 mmol) were allowed to react for 12 hours at 125° C. in 62.5 g of DMF. After completion of the reaction, the pH was adjusted, and then the reaction liquid was subjected to filtration and washing with MeOH. Subsequently, the pH was adjusted again, the resultant was washed with water, and recrystallization was performed. Thus, Compound 13 was obtained.

FT-IR (KBr): 2962 cm$^{-1}$: O—H stretching vibration, 1434, 1389 cm$^{-1}$: triazole ring stretching vibration, 668 cm$^{-1}$: C—S stretching vibration $^1$H-NMR (CDCl$_3$400 MHz): δ 0.87 (t, 3H, C$\underline{H}_3$(CH$_2$)$_{11}$—S), 1.26 (m, 16H, CH$_3$ (C$\underline{H}_2$)$_8$(CH$_2$)$_3$—S), 1.39 (s, 9H, -Ph-OH—C(C$\underline{H}_3$)$_3$—C(CH$_3$)$_3$), 1.51 (m, 11H, -Ph-OH—C(CH$_3$)$_3$—C(C$\underline{H}_3$)$_3$, CH$_3$ (CH$_2$)$_8$ C$\underline{H}_2$(CH$_2$)$_2$—S), 1.74 (quin, 2H, CH$_3$ (CH$_2$)$_9$ C$\underline{H}_2$CH$_2$—S), 3.03 (t, 2H, CH$_3$ (CH$_2$)$_9$CH$_2$C$\underline{H}_2$—S), 7.35 (d, 1H), 7.41 (s, 1H), 7.71 (s, 1H), 7.82 (d, 1H), 8.24 (d, 1H), (insg.5arom. C$\underline{H}$), 11.67 (s, 1H, -Ph-O$\underline{H}$—C(CH$_3$)$_3$—C(CH$_3$)$_3$)

$^{13}$C-NMR (CDCl$_3$400 MHz): δ 14.1 ($\underline{C}$H$_3$(CH$_2$)$_{11}$—S), 22.7 (CH$_3$ $\underline{C}$H$_2$ (CH$_2$)$_{10}$—S), 28.7~29.7 (CH$_3$ CH$_2$ ($\underline{C}$H$_2$)$_8$CH$_2$ CH$_2$—S), 29.6 (-Ph-OH—C(CH$_3$)$_3$—C($\underline{C}$H$_3$)$_3$), 31.5 (-Ph-OH—C($\underline{C}$H$_3$)$_3$—C(CH$_3$)$_3$), 31.9 (CH$_3$(CH$_2$)$_9$ $\underline{C}$H$_2$CH$_2$—S), 33.2 (-Ph-OH—$\underline{C}$(CH$_3$)$_3$—C(CH$_3$)$_3$), 34.6 (CH$_3$(CH$_2$)$_9$CH$_2$$\underline{C}$H$_2$—S), 35.7 (-Ph-OH—C(CH$_3$)$_3$—$\underline{C}$(CH$_3$)$_3$), 113.6, 116.0, 117.6, 129.2, 143.4 ($\underline{C}$H$_{arom}$), 125.0, 141.2, 143.4 ($\underline{C}_{arom}$), 137.9 ($\underline{C}_{arom}$—S), 125.2, 138.6 ($\underline{C}_{arom}$—C(CH$_3$)$_3$), 146.6 ($\underline{C}_{arom}$—OH)

<Synthesis Example 21> Synthesis of Compound 14

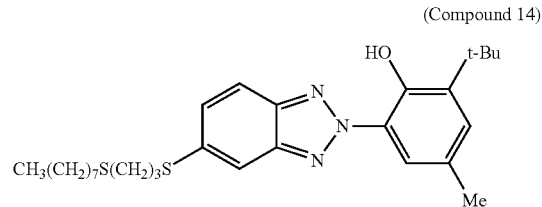

(Compound 14)

Compound 14 was synthesized by a synthesis method similar to that used for Compound 7, using Intermediate 4 (11.5 g, 52.1 mmol). The properties values are shown below.

FT-IR (KBr): 3057 cm$^{-1}$: O—H stretching vibration, 1437, 1391 cm$^{-1}$: triazole ring stretching vibration, 664 cm$^{-1}$: C—S stretching vibration $^1$H-NMR (CDCl$_3$ 400 MHz): δ 0.81 (t, 3H, C$\underline{H}_3$(CH$_2$)$_7$—S), 1.20 (m, 8H, CH$_3$(C H$_2$)$_4$(CH$_2$)$_3$—S), 1.30 (m, 2H, CH$_3$(CH$_2$)$_4$CH$_2$(CH$_2$)$_2$—S), 1.49 (s, 9H, -Ph-OH—CH$_3$—C(CH$_3$)$_3$), 1.54 (quin, 2H, CH$_3$(CH$_2$)$_4$CH$_2$CH$_2$CH$_2$—S), 1.91 (quin, 2H, S—CH$_2$C H$_2$CH$_2$—S-Ph), 2.38 (s, 3H, -Ph-OH—CH$_3$—C(CH$_3$)$_3$), 2.48 (t, 2H, CH$_3$(CH$_2$)$_4$CH$_2$CH$_2$CH$_2$—S), 2.68 (t, 2H, S—C H$_2$CH$_2$CH$_2$—S-Ph), 3.17 (t, 2H, S—CH$_2$CH$_2$CH$_2$—S-Ph), 7.16 (s, 1H), 7.37 (d, 1H), 7.70 (s, 1H), 7.81 (d, 1H), 8.05 (d, 1H), (insg.5arom. CH), 11.61 (s, 1H, -Ph-OH—CH$_3$—C(CH$_3$)$_3$)

$^{13}$C-NMR (CDCl$_3$, 400 MHz): δ14.0 (CH$_3$(CH$_2$)$_7$—S), 20.1 (-Ph-OH—CH$_3$—C(CH$_3$)$_3$), 22.6 (-Ph-OH—CH$_3$—C(CH$_3$)$_3$), 28.4 (CH$_3$CH$_2$(C H$_2$)$_6$—S), 28.9 (CH$_3$(CH$_2$)$_5$ CH$_2$CH$_2$—S), 29.2 (CH$_3$(CH$_2$)$_3$CH$_2$CH$_2$(CH$_2$)$_2$—S), 29.6 (CH$_3$(CH$_2$)$_6$CH$_2$—S), 30.9 (S—CH$_2$CH$_2$CH$_2$—S), 31.8 (CH$_3$CH$_2$ CH$_2$(CH$_2$)$_5$—S), 31.9 (-Ph-OH—CH$_3$—C (CH$_3$)$_3$), 32.2 (S—CH$_2$CH$_2$CH$_2$—S), 35.4 (S—CH$_2$CH$_2$ CH$_2$—S), 114.4, 117.6, 119.3, 128.7, 129.4 (CH$_{arom}$), 141.3, 143.3 (C$_{arom}$), 125.4 (C$_{arom}$—N), 128.3 (C$_{arom}$—CH$_3$), 137.1 (C$_{arom}$—S), 139.1 (C$_{arom}$—C(CH$_3$)$_3$), 146.7 (C$_{arom}$—OH)

<Synthesis Example 22> Synthesis of Compound 15

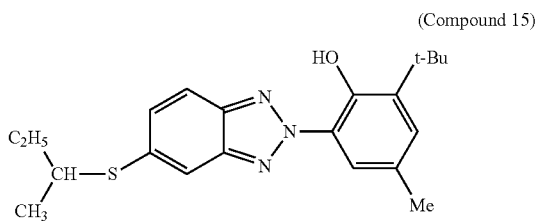 [SMILES: CCC(C)Sc1ccc2nn(-c3cc(C)cc(C(C)(C)C)c3O)nc2c1]
(Compound 15)

2-(2-Hydroxy-3-tert-butyl-5-methylphenyl)-5-chlorobenzotriazole (36.3 g, 0.115 mol), sec-butylmercaptan (20.8 g, 0.231 mol), potassium carbonate (35.0 g, 0.253 mol), and potassium iodide (1.3 g, 0.008 mol) were allowed to react for 12 hours at 125° C. in 100 g of DMF. After completion of the reaction, the reaction liquid was subjected to pH adjustment, filtration, washing with MeOH, and washing with water, and recrystallization was performed. Thus, Compound 15 was obtained.

FT-IR (KBr): 2961 cm$^{-1}$: O—H stretching vibration, 1448, 1391 cm$^{-1}$: triazole ring stretching vibration, 665 cm$^{-1}$: C—S stretching vibration $^1$H-NMR (CDCl$_3$ 400 MHz): δ 1.06 (t, 3H, CH$_3$CH$_2$CH(CH$_3$)—S), 1.37 (d, 3H, CH$_3$CH$_2$CH(CH$_3$)—S), 1.49 (S, 9H, -Ph-OH—CH$_3$—C (CH$_3$)$_3$), 1.61 (m, 2H, CH$_3$CH$_2$CH(CH$_3$)—S), 2.38 (s, 3H, -Ph-OH—CH$_3$—C(CH$_3$)$_3$), 3.32 (m, 1H, CH$_3$CH$_2$C H(CH$_3$)—S), 7.17 (s, 1H), 7.42 (d, 1H), 7.80 (s, 1H), 7.84 (d, 1H), 8.06 (d, 1H), (insg.5arom. CH), 11.62 (s, 1H, -Ph-OH—CH$_3$—C(CH$_3$)$_3$) $^{13}$C-NMR (CDCl$_3$ 400 MHz): δ 11.5 (CH$_3$CH$_2$CH(CH$_3$))—S), 20.3 (CH$_3$CH$_2$CH(CH$_3$)—S), 20.9 (-Ph-OH—CH$_3$—C(CH$_3$)$_3$), 29.4 (CH$_3$CH$_2$CH(CH$_3$)—S), 29.5 (-Ph-OH—CH$_3$—C(CH$_3$)$_3$), 35.4 (-Ph-OH—CH$_3$—C(CH$_3$)$_3$), 44.6 (CH$_3$CH$_2$CH(CH$_3$)—S), 117.3, 117.5, 119.3, 128.3, 128.8 (CH$_{arom}$), 141.5, 143.2 (C$_{arom}$), 125.4 (C$_{arom}$—N), 131.2 (C$_{arom}$—CH$_3$), 136.4 (C$_{arom}$—S), 139.1 (C$_{arom}$—C(CH$_3$)$_3$), 146.7 (C$_{arom}$—OH)

<Synthesis Example 23> Synthesis of Compound 16

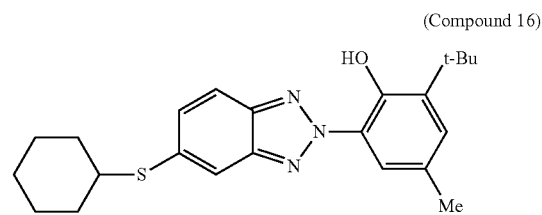 [SMILES: Cc1cc(-n2nc3ccc(SC4CCCCC4)cc3n2)c(O)c(C(C)(C)C)c1]
(Compound 16)

2-(2-Hydroxy-3-tert-butyl-5-methylphenyl)-5-chlorobenzotriazole (32.3 g, 0.102 mol), cyclohexanethiol (23.8 g, 0.205 mol), potassium carbonate (31.1 g, 0.225 mol), and potassium iodide (1.2 g, 0.007 mol) were allowed to react for 12 hours at 125° C. in 100 g of DMF. After completion of the reaction, the reaction liquid was subjected to pH adjustment, filtration, washing with MeOH, and washing with water, and recrystallization was performed. Thus, Compound 16 was obtained.

FT-IR (KBr): 2930 cm$^{-1}$: O—H stretching vibration, 1450, 1391 cm$^{-1}$: triazole ring stretching vibration, 667 cm$^{-1}$: C—S stretching vibration $^1$H-NMR (CDCl$_3$ 400 MHz): δ 1.40 (m, 4H, CH$_2$(CH$_2$)$_2$(CH$_2$)$_2$CH—S), 1.49 (S, 9H, -Ph-OH—CH$_3$—C(CH$_3$)$_3$), 1.54 (m, 2H, C H$_2$(CH$_2$)$_2$(CH$_2$)$_{22}$(CH$_2$)$_2$CH—S), 1.83 (m, 2H, CH$_2$(CH$_2$)$_2$ CH$_2$CH$_2$CH—S), 2.06 (m, 2H, CH$_2$(CH$_2$)$_2$C H$_2$CH$_2$CH—S), 2.38 (s, 3H, -Ph-OH—CH$_3$—C(CH$_3$)$_3$), 3.29 (m, 1H, CH$_2$CH$_2$CH$_2$CH—S), 7.17 (s, 1H), 7.43 (d, 1H), 7.80 (s, 1H), 7.84 (d, 1H), 8.06 (d, 1H), (insg.5arom. C H), 11.62 (s, 1H, -Ph-OH—CH$_3$—C(CH$_3$)$_3$) $^{13}$C-NMR (CDCl$_3$ 400 MHz): δ 20.9 (-Ph-OH—CH$_3$—C(CH$_3$)$_3$), 25.7 (CH$_2$(CH$_2$)$_2$(CH$_2$)$_2$CH—S), 26.0 (CH$_2$(CH$_2$)$_2$ (CH$_2$)$_2$CH—S), 29.5 (-Ph-OH—CH$_3$—C(CH$_3$)$_3$), 33.1 (CH$_2$(CH$_2$)$_2$ (CH$_2$)$_2$CH—S), 35.4 (-Ph-OH—CH$_3$—C(CH$_3$)$_3$), 46.3 (CH$_2$(CH$_2$)$_2$(CH$_2$)$_2$CH—S), 117.2, 117.5, 119.3, 128.3, 128.8 (CH$_{arom}$), 141.5, 143.2 (C$_{arom}$), 125.4 (C$_{arom}$—N), 131.2 (C$_{arom}$—CH$_3$), 136.1 (C$_{arom}$—S), 139.1 (C$_{arom}$—C(CH$_3$)$_3$), 146.7 (C$_{arom}$—OH)

<Synthesis Example 24> Synthesis of Compound 17

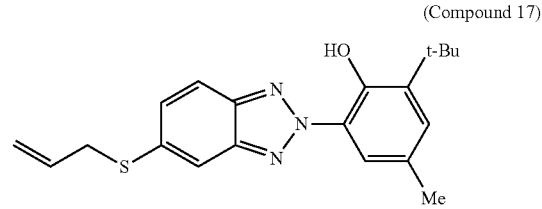 [SMILES: C=CCSc1ccc2nn(-c3cc(C)cc(C(C)(C)C)c3O)nc2c1]
(Compound 17)

2-(2-Hydroxy-3-tert-butyl-5-methylphenyl)-5-chlorobenzotriazole (50.0 g, 0.158 mol), allylmercaptan (23.5 g, 0.317 mol), potassium carbonate (48.1 g, 0.348 mol), and potassium iodide (1.8 g, 0.011 mol) were allowed to react for 12 hours at 125° C. in 125 g of DMF. After completion of the reaction, the reaction liquid was subjected to pH adjustment, filtration, washing with MeOH, and washing with water, and recrystallization was performed. Thus, Compound 17 was obtained.

FT-IR (KBr): 3092 cm$^{-1}$: O—H stretching vibration, 2999 cm$^{-1}$: =C—H stretching vibration, 1449, 1390 cm$^{-1}$: triazole ring stretching vibration, 664 cm$^{-1}$: C—S stretching vibration $^1$H-NMR (CDCl$_3$ 400 MHz): δ 1.49 (S, 9H, -Ph-OH—CH$_3$—C(CH$_3$)$_3$), 1.55 (m, 2H, CH$_2$=CHCH$_2$—S), 2.38 (s, 3H, -Ph-OH—CH$_3$—C(CH$_3$)$_3$), 3.38 (m, 1H, CH$_2$=CHCH$_2$—S), 3.78 (m, 1H, CH$_2$=CHCH$_2$—S), 4.23 (m, 1H, CH$_2$=CHCH$_2$—S), 7.16 (s, 1H), 7.31 (d, 1H), 7.71 (s, 1H), 7.73 (d, 1H), 8.05 (d, 1H), (insg.5arom. CH), 11.66 (s, 1H, -Ph-OH—CH$_3$—C(CH$_3$)$_3$) $^{13}$C-NMR (CDCl$_3$ 400 MHz): δ 21.0 (-Ph-OH—CH$_3$—C(CH$_3$)$_3$), 22.5 (CH$_2$=CHCH$_2$—S), 29.6 (-Ph-OH—CH$_3$—C(CH$_3$)$_3$), 35.4 (-Ph-OH—CH$_3$—C(CH$_3$)$_3$), 41.8 (CH$_2$=CHCH$_2$—S), 46.3 (CH$_2$=CHCH$_2$—S), 116.7, 119.3, 123.3, 128.2, 128.6 (CH$_{arom}$), 140.8, 141.7 (C$_{arom}$), 125.4 (C$_{arom}$—N), 124.1 (C$_{arom}$—CH$_3$), 140.7 (C$_{arom}$—S), 139.0 (C$_{arom}$—C(CH$_3$)$_3$), 146.6 (C$_{arom}$—OH)

<Synthesis Example 25> Synthesis of Compound 18

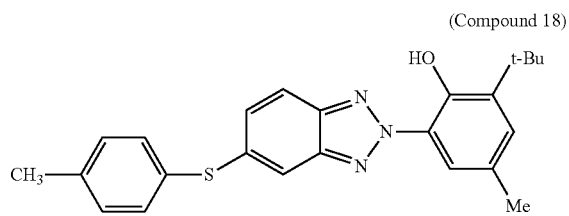 [SMILES: Cc1ccc(Sc2ccc3nn(-c4cc(C)cc(C(C)(C)C)c4O)nc3c2)cc1]
(Compound 18)

2-(2-Hydroxy-3-tert-butyl-5-methylphenyl)-5-chlorobenzotriazole (25.0 g, 79.2 mmol), p-toluenethiol (19.7 g, 158.3 mmol), potassium carbonate (24.1, 174.2 mmol), and potassium iodide (0.92 g, 5.54 mmol) were allowed to react for 12 hours at 125° C. in 62.5 g of DMF. After completion of the reaction, the pH was adjusted, subsequently the reaction liquid was subjected to filtration, washing with MeOH, and washing with water, and recrystallization was performed. Thus, Compound 18 was obtained.

FT-IR (KBr): 3000 cm$^{-1}$: O—H stretching vibration, 1444, 1389 cm$^{-1}$: triazole ring stretching vibration, 667 cm$^{-1}$: C—S stretching vibration $^1$H-NMR (CDCl$_3$400 MHz): δ1.48 (s, 9H, -Ph-OH—CH$_3$—C(CH$_3$)$_3$), 2.37 (s, 3H, -Ph-OH—CH$_3$—C(CH$_3$)$_3$), 2.40 (s, 3H, CH$_3$-Ph-S—), 7.16 (s, 1H), 7.23 (s, 2H), 7.32 (d, 1H), 7.43 (s, 2H), 7.56 (s, 1H), 7.81 (d, 1H), 8.02 (d, 1H), (insg.9arom. CH), 11.56 (s, 1H, -Ph-OH—CH$_3$—C(CH$_3$)$_3$)

$^{13}$C-NMR (CDCl$_3$400 MHz): δ20.9 (-Ph-OH—CH$_3$—C(CH$_3$)$_3$), 21.2 (CH$_3$-Ph-S—), 29.5 (-Ph-OH—CH$_3$—C(CH$_3$)$_3$), 35.4 (-Ph-OH—CH$_3$—C(CH$_3$)$_3$), 115.3, 117.8, 119.3, 128.7, 129.3 130.5, 133.7 (CH$_{arom}$), 125.4, 141.2, 143.4 (C$_{arom}$), 128.3 (C$_{arom}$—CH$_3$), 138.9 (C$_{arom}$—S), 138.7 (S—C$_{arom}$), 139.1 (C$_{arom}$—C(CH$_3$)$_3$), 146.7 (C$_{arom}$—OH)

<Synthesis Example 26> Synthesis of Compound 19

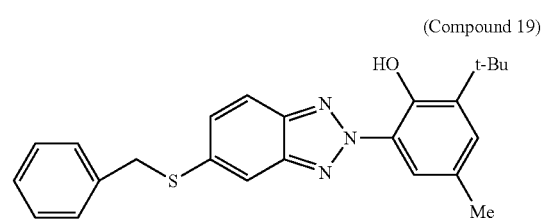 [SMILES: Cc1cc(-n2nc3ccc(SCc4ccccc4)cc3n2)c(O)c(C(C)(C)C)c1]
(Compound 19)

2-(2-Hydroxy-3-tert-butyl-5-methylphenyl)-5-chlorobenzotriazole (20.0 g, 63.3 mmol), benzylmercaptan (15.7 g, 126.6 mmol), potassium carbonate (19.3 g, 139.4 mmol), and potassium iodide (0.74 g, 4.5 mmol) were allowed to react for 9 hours at 125° C. in 50.0 g of DMF. After completion of the reaction, the pH was adjusted, subsequently the reaction liquid was subjected to filtration, washing with MeOH, and washing with water, and recrystallization was performed. Thus, Compound 19 was obtained.

FT-IR (KBr): 2960 cm$^{-1}$: O—H stretching vibration, 1441, 1392 cm$^{-1}$: triazole ring stretching vibration, 664 cm$^{-1}$: C—S stretching vibration $^1$H-NMR (CDCl$_3$400 MHz): δ1.49 (s, 9H, -Ph-OH—CH$_3$—C(CH$_3$)$_3$), 2.38 (s, 3H, -Ph-OH—CH$_3$—C(CH$_3$)$_3$), 4.24 (s, 2H, Ph-CH$_2$—S—), 7.16 (s, 1H), 7.26~7.38 (m, 6H), 7.72 (s, 1H), 7.80 (d, 1H), 8.04 (d, 1H), (insg.10arom. CH), 11.58 (s, 1H, -Ph-OH—CH$_3$—C(CH$_3$)$_3$)

$^{13}$C-NMR (CDCl$_3$400 MHz): δ20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 38.6 (Ph-CH$_2$—S—), 115.4, 117.6, 119.3, 128.7, 128.8, 128.8, 129.7, 137.0 (CH$_{arom}$), 125.4, 141.4, 143.4 (C$_{arom}$), 128.3 (C$_{arom}$—CH$_3$), 136.5 (C$_{arom}$—CH$_2$—S—), 138.7 (S—C$_{arom}$), 139.1 (C$_{arom}$—C(CH$_3$)$_3$), 146.7 (C$_{arom}$—OH)

<Synthesis Example 27> Synthesis of Compound 20

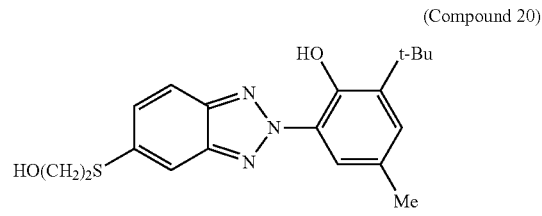
(Compound 20)

2-(2-Hydroxy-3-tert-butyl-5-methylphenyl)-5-chlorobenzotriazole (50.5 g, 0.160 mol), 2-mercaptoethanol (25.0 g, 0.320 mol), potassium carbonate (48.6 g, 0.352 mol), and potassium iodide (1.9 g, 0.011 mol) were allowed to react for 12 hours at 125° C. in 125 g of DMF. After completion of the reaction, the reaction liquid was subjected to pH adjustment, filtration, washing with MeOH, and washing with water, and recrystallization was performed. Thus, compound 20 was obtained.

FT-IR (KBr): 3350 cm$^{-1}$: O—H stretching vibration, 1437, 1392 cm$^{-1}$: triazole ring stretching vibration, 666 cm$^{-1}$: C—S stretching vibration $^1$H-NMR (CDCl$_3$ 400 MHz): δ 1.49 (S, 9H, -Ph-OH—CH$_3$—C(CH$_3$)$_3$), 2.38 (s, 3H, -Ph-OH—C<u>H</u>₃—C(CH₃)₃), 2.79 (t, 2H, HOCH₂C<u>H</u>₂—S), 3.25 (t, 2H, HOC<u>H</u>₂CH₂—S), 7.17 (s, 1H), 7.41 (d, 1H), 7.83 (s, 1H), 7.84 (d, 1H), 8.05 (d, 1H), (insg.5arom. C<u>H</u>), 11.56 (s, 1H, -Ph-O<u>H</u>—CH₃—C(CH₃)₃) ¹³C-NMR (CDCl₃ 400 MHz): δ 20.9 (-Ph-OH—<u>C</u>H₃—C(CH₃)₃), 29.5 (-Ph-OH—CH₃—C(<u>C</u>H₃)₃), 35.4 (-Ph-OH—CH₃—<u>C</u>(CH₃)₃), 36.8 (HO<u>C</u>H₂CH₂—S), 60.3 (HOCH₂<u>C</u>H₂—S), 115.8, 118.0, 119.3, 128.4, 129.7 (<u>C</u>H<sub>arom</sub>), 141.5, 143.2 (<u>C</u><sub>arom</sub>), 125.3 (<u>C</u><sub>arom</sub>—N), 128.9 (<u>C</u><sub>arom</sub>—CH₃), 135.7 (<u>C</u><sub>arom</sub>—S), 139.2 (<u>C</u><sub>arom</sub>—C(CH₃)₃), 146.7 (<u>C</u><sub>arom</sub>—OH)

<Synthesis Example 28> Synthesis of Compound 21

(Compound 21)

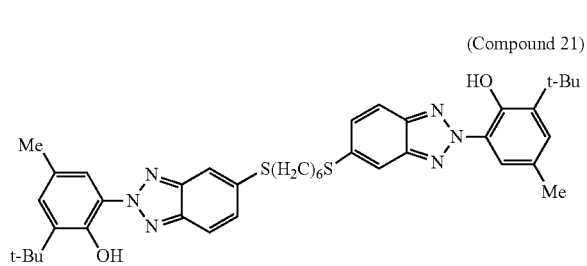

2-(2-Hydroxy-3-tert-butyl-5-methylphenyl)-5-chlorobenzotriazole (10.0 g, 31.7 mmol), hexanedithiol (4.76 g, 31.7 mmol), potassium carbonate (8.75 g, 63.3 mmol), and potassium iodide (0.37 g, 2.2 mmol) were allowed to react for 12 hours at 130° C. in 50 mL of DMF. After completion of the reaction, toluene was added thereto, and the reaction liquid was subjected to washing with water, distillation of the solvent, and recrystallization. Thus, Compound 21 was obtained.

FT-IR (KBr): 3009 cm⁻¹: O—H stretching vibration, 1431, 1391 cm⁻¹: triazole ring stretching vibration, 656 cm⁻¹: C—S stretching vibration ¹H-NMR (CDCl₃ 400 MHz): δ1.49 (s, 18H, (-Ph-OH—CH₃—C(C<u>H</u>₃)₃)₂), 1.55 (m, 4H, —S—CH₂CH₂C<u>H</u>₂C<u>H</u>₂CH₂CH₂—S—), 1.77 (m, 4H, —S—CH₂C<u>H</u>₂CH₂CH₂C<u>H</u>₂CH₂—S—), 2.38 (s, 6H, (-Ph-OH—C<u>H</u>₃—C(CH₃)₃)₂), 3.04 (t, 4H, —S—C<u>H</u>₂CH₂CH₂CH₂CH₂C<u>H</u>₂—S—), 7.16 (s, 2H), 7.37 (d, 2H), 7.70 (s, 2H), 7.81 (d, 2H), 8.05 (s, 2H) (insg.10arom. C<u>H</u>), 11.60 (s, 2H, -Ph-O<u>H</u>—CH₃—C(CH₃)₃)

¹³C-NMR (CDCl₃ 400 MHz): δ20.9 (-Ph-OH—<u>C</u>H₃—C(CH₃)₃)₂, 28.4 (-Ph-OH—CH₃—C(<u>C</u>H₃)₃)₂, 28.6 (—S—CH₂<u>C</u>H₂<u>C</u>H₂CH₂CH₂—S—), 29.5 (-Ph-OH—CH₃—C(<u>C</u>H₃)₃)₂, 33.1 (—S—<u>C</u>H₂CH₂CH₂CH₂<u>C</u>H₂CH₂—S—), 35.4 (—S—<u>C</u>H₂CH₂CH₂CH₂CH₂<u>C</u>H₂—S—), 113.7, 117.6, 119.3, 128.3, 129.3 (<u>C</u>H<sub>arom</sub>), 141.2, 143.4 (<u>C</u><sub>arom</sub>), 125.4 (<u>C</u><sub>arom</sub>—N), 128.3 (<u>C</u><sub>arom</sub>—CH3), 137.7 (<u>C</u><sub>arom</sub>—S), 139.1 (<u>C</u><sub>arom</sub>—C(CH₃)₃), 146.7 (<u>C</u><sub>arom</sub>—OH)

<Synthesis Example 29> Synthesis of Compound 22

(Compound 22)

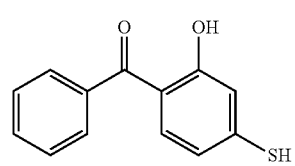 [SMILES: O=C(c1ccccc1)c1ccc(S)cc1O]

2,4-Dihydroxybenzophenone (8.6 g, 40 mmol), 1,4-diazabicyclo[2.2.2]octane (9.0 g, 80 mmol), and dimethylthiocarbamoyl chloride (6.18 g, 50 mmol) were allowed to react for 12 hours at 80° C. in 100 mL of DMF. After completion of the reaction, toluene was added to the reaction mixture, and the mixture was subjected to washing with water, distillation of the solvent, and purification using a column. Thus, Intermediate 11 as described below was obtained.

(Intermediate 11)

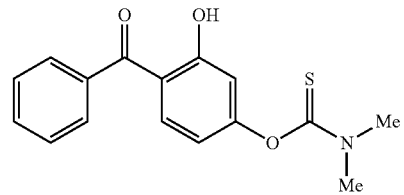

Intermediate 11 (5.0 g, 16.6 mmol) was allowed to react for 40 minutes at 240° C. in 10 mL of sulfolane. After completion of the reaction, toluene was added thereto, and the mixture was subjected to washing with water, distillation of the solvent, and purification using a column. Thus, Intermediate 12 as described below was obtained.

(Intermediate 12)

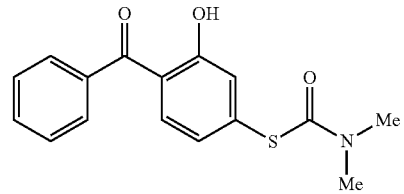

Intermediate 12 (3.46 g, 11.4 mmol) and potassium hydroxide (3.22 g, 57.4 mmol) were allowed to react for 6 hours in 100 mL of ethanol, while the mixture was heated to reflux. After completion of the reaction, the reaction mixture was acidified with hydrochloric acid, toluene was added thereto, and the mixture was subjected to washing with water, distillation of the solvent, and purification using a column. Thus, Compound 22 was obtained.

FT-IR (KBr): 3055 cm⁻¹: O—H stretching vibration, 2559 cm⁻¹: S—H stretching vibration, 1624 cm⁻¹: C=O stretching vibration ¹H-NMR (CDCl₃ 400 MHz): δ 3.65 (s, 1H, -Ph-OH—S<u>H</u>), 6.68 (d, 1H), 6.93 (s, 1H), 7.44 (d, 1H), 7.51 (m, 2H), 7.58 (m, 1H), 7.65 (d, 2H) (insg.8arom. C<u>H</u>), 12.28 (s, 1H, -Ph-O<u>H</u>—SH)

¹³C-NMR (CDCl₃ 400 MHz): δ 115.4, 117.5, 127.4, 128.0 (<u>C</u>H<sub>arom</sub>), δ 130.9, 132.9 (<u>C</u><sub>arom</sub>), δ 142.26 (<u>C</u><sub>arom</sub>SH), δ 162.5 (<u>C</u><sub>arom</sub>—OH), δ 199.6 (<u>C</u>(=O))

\<Synthesis Example 30\> Synthesis of Compound 23

(Compound 23)

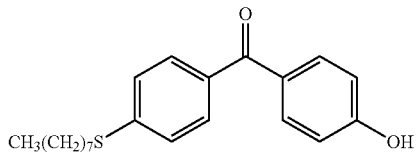

4-Chloro-4'-hydroxybenzophenone (5.44 g, 23.4 mmol), octanethiol (6.84 g, 46.8 mmol), and potassium carbonate (13.7 g, 99.2 mmol) were allowed to react for 4 hours at 200° C. in 2 mL of N-methylpyrrolidone. After completion of the reaction, toluene was added thereto, and the mixture was subjected to washing with water, distillation of the solvent, and purification using a column. Thus, Compound 23 was obtained.

FT-IR (KBr): 3266 cm$^{-1}$: O—H stretching vibration, 1630 cm$^{-1}$: C=O stretching vibration, 646 cm$^{-1}$: C—S stretching vibration $^1$H-NMR (CDCl$_3$ 400 MHz): δ 0.88 (t, 3H, C$\underline{H}_3$(CH$_2$)$_7$—S), 1.28 (m, 8H, CH$_3$(C$\underline{H}_2$)$_4$(CH$_2$)$_3$—S), 1.45 (m, 2H, CH$_3$(CH$_2$)$_4$C$\underline{H}_2$CH$_2$CH$_2$—S), 1.71 (quin, 2H, CH$_3$(CH$_2$)$_5$C$\underline{H}_2$CH$_2$—S), 3.00 (t, 2H, CH$_3$(CH$_2$)$_5$CH$_2$C$\underline{H}_2$—S), 6.22 (s, 1H, —S-Ph-C=O-Ph-O$\underline{H}$), 6.92 (d, 2H), 7.31 (d, 2H), 7.68 (d, 2H), 7.74 (d, 2H) (insg.8arom. C$\underline{H}$)

$^{13}$C-NMR (CDCl$_3$ 400 MHz): δ14.1 ($\underline{C}$H$_3$(CH$_2$)$_7$—S), 22.6 (CH$_3$$\underline{C}$H$_2$(CH$_2$)$_5$—S), 28.8 (CH$_3$(CH$_2$)$_4$$\underline{C}$H$_2$(CH$_2$)$_2$—S), 28.9 (CH$_3$(CH$_2$)$_3$$\underline{C}$H$_2$(CH$_2$)$_3$—S), 29.1 (CH$_3$CH$_2$$\underline{C}$H$_2$(CH$_2$)$_4$—S), 31.8 (CH$_3$$\underline{C}$H$_2$CH$_2$(CH$_2$)$_4$—S), 32.2 (CH$_3$(CH$_2$)$_6$$\underline{C}$H$_2$—S), 115.3, 126.3, 130.5, 132.8 ($\underline{C}$H$_{arom}$), 134.4 ($\underline{C}_{arom}$), 143.9 ($\underline{C}_{arom}$S—), 160.3 ($\underline{C}_{arom}$—OH), 195.4 (Ph-$\underline{C}$(=O)-Ph)

\<Synthesis Example 31\> Synthesis of Compound 24

(Compound 24)

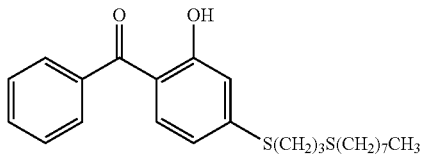

Intermediate 3 (1.20 g, 4.7 mmol), Compound 22 (2.00 g, 8.6 mmol), and potassium carbonate (2.40 g, 17.2 mmol) were allowed to react for 6 hours in 30 mL of acetonitrile, while the mixture was heated to reflux. After completion of the reaction, toluene was added thereto, and the mixture was washed with water, distillation of the solvent, and purification using a column. Thus, Compound 24 was obtained.

FT-IR (KBr): 3059 cm$^{-1}$: O—H stretching vibration, 1615 cm$^{-1}$: C=O stretching vibration, 669 cm$^{-1}$: C—S stretching vibration $^1$H-NMR (CDCl$_3$ 400 MHz): δ 0.88 (t, 3H, C$\underline{H}_3$(CH$_2$)$_7$—S), 1.28 (m, 4H, CH$_3$(C$\underline{H}_2$)$_4$(CH$_2$)$_3$—S), 1.37 (m, 2H, CH$_3$(CH$_2$)$_4$C$\underline{H}_2$(CH$_2$)$_2$—S), 1.58 (m, 2H, CH$_3$(CH$_2$)$_5$C$\underline{H}_2$CH$_2$—S), 2.00 (quin, 2H, S—CH$_2$C$\underline{H}_2$CH$_2$—S-Ph), 2.51 (t, 2H, CH$_3$(CH$_2$)$_5$CH$_2$C$\underline{H}_2$—S), 2.67 (t, 2H, S—C$\underline{H}_2$CH$_2$CH$_2$—S-Ph), 3.12 (t, 2H, S—CH$_2$CH$_2$C$\underline{H}_2$—S-Ph), 6.71 (d, 1H), 6.90 (s, 1H), 7.44 (d, 1H), 7.51 (m, 2H), 7.58 (m, 1H), 7.65 (d, 2H) (insg.8arom. C$\underline{H}$), 12.37 (s, 1H, -Ph-O$\underline{H}$—S—)

$^{13}$C-NMR (CDCl$_3$ 400 MHz): δ14.1 ($\underline{C}$H$_3$(CH$_2$)$_7$—S), 22.7 (CH$_3$$\underline{C}$H$_2$(CH$_2$)$_6$—S), 28.3 (CH$_3$(CH$_2$)$_3$$\underline{C}$H$_2$(CH$_2$)$_3$—S), 28.9 (CH$_3$(CH$_2$)$_5$$\underline{C}$H$_2$CH$_2$—S), 29.2 (CH$_3$(CH$_2$)$_3$$\underline{C}$H$_2$CH$_2$(CH$_2$)$_2$—S), 29.7 (CH$_3$(CH$_2$)$_6$$\underline{C}$H$_2$—S), 30.1 (S—$\underline{C}$H$_2$CH$_2$CH$_2$—S), 30.9 (S—CH$_2$$\underline{C}$H$_2$CH$_2$—S), 31.8 (CH$_3$CH$_2$ $\underline{C}$H$_2$(CH$_2$)$_5$—S), 32.2 (S—CH$_2$CH$_2$$\underline{C}$H$_2$—S), 114.1, 116.0, 116.7, 128.4, 129.0, 131.8, 133.5 ($\underline{C}$H$_{arom}$), 130.9, 132.9 ($\underline{C}_{arom}$), 138.0 ($\underline{C}_{arom}$S—), 163.7 ($\underline{C}_{arom}$—OH), 200.5 (Ph-$\underline{C}$(=O)-Ph)

\<Synthesis Example 32\> Synthesis of Compound 25

(Compound 25)

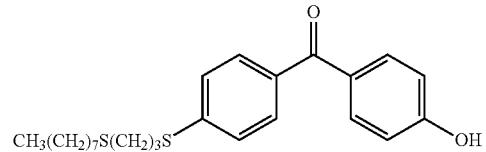

4-Chloro-4'-hydroxybenzophenone (1.68 g, 7.2 mmol), Intermediate 4 (2.54 g, 11.5 mmol), and potassium carbonate (1.60 g, 11.5 mmol) were allowed to react for 4 hours at 200° C. in 2 mL of N-methylpyrrolidone. After completion of the reaction, toluene was added thereto, and the mixture was subjected to washing with water, distillation of the solvent, and purification using a column. Thus, Compound 25 was obtained as a liquid containing 90% or more of the compound.

FT-IR (KBr): 3266 cm$^{-1}$: O—H stretching vibration, 1630 cm$^{-1}$: C=O stretching vibration, 646 cm$^{-1}$: C—S stretching vibration $^1$H-NMR (CDCl$_3$ 400 MHz): δ 0.80 (t, 3H, C$\underline{H}_3$(CH$_2$)$_7$—S), 1.20 (m, 8H, CH$_3$(C$\underline{H}_2$)$_4$(CH$_2$)$_3$—S), 1.30 (m, 2H, CH$_3$(CH$_2$)$_4$C$\underline{H}_2$CH$_2$CH$_2$—S), 1.50 (quin, 2H, CH$_3$(CH$_2$)$_5$C$\underline{H}_2$CH$_2$—S), 1.91 (quin, 2H, S—CH$_2$C$\underline{H}_2$CH$_2$—S-Ph), 2.43 (t, 2H, CH$_3$(CH$_2$)$_6$C$\underline{H}_2$—S), 2.60 (t, 2H, S—C$\underline{H}_2$CH$_2$CH$_2$—S-Ph), 3.00 (t, 2H, S—CH$_2$CH$_2$C$\underline{H}_2$—S-Ph), 5.93 (s, 1H, -Ph-C=O-Ph-O$\underline{H}$), 6.83 (d, 2H), 7.30 (d, 2H), 7.68 (d, 2H), 7.63 (d, 2H) (insg.8arom. C$\underline{H}$)

$^{13}$C-NMR (CDCl$_3$ 400 MHz): δ14.1 ($\underline{C}$H$_3$(CH$_2$)$_7$—S), 22.6 (CH$_3$$\underline{C}$H$_2$(CH$_2$)$_6$—S), 28.5 (CH$_3$(CH$_2$)$_2$$\underline{C}$H$_2$(CH$_2$)$_3$—S), 28.9 (CH$_3$(CH$_2$)$_5$$\underline{C}$H$_2$CH$_2$—S), 29.2 (CH$_3$(CH$_2$)$_3$$\underline{C}$H$_2$CH$_2$(CH$_2$)$_2$—S), 29.7 (CH$_3$(CH$_2$)$_6$$\underline{C}$H$_2$—S), 30.9 (S—$\underline{C}$H$_2$CH$_2$CH$_2$—S), 31.0 (S—CH$_2$$\underline{C}$H$_2$CH$_2$—S), 31.8 (CH$_3$CH$_2$ $\underline{C}$H$_2$(CH$_2$)$_5$—S), 32.4 (S—CH$_2$CH$_2$$\underline{C}$H$_2$—S), 114.4, 125.5, 128.6, 129.6 ($\underline{C}$H$_{arom}$), 131.9, 133.2 ($\underline{C}_{arom}$), 142.3 ($\underline{C}_{arom}$S—), 159.8 ($\underline{C}_{arom}$—OH), 194.5 (Ph-$\underline{C}$(=O)-Ph)

<Synthesis Example 33> Synthesis of Compound 26

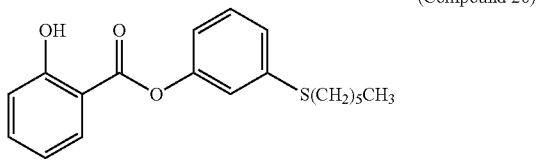
(Compound 26)

Salicylic acid (8.8 g, 63.9 mmol) and thionyl chloride (22.8 g, 191.6 mmol) were allowed to react for 3 hours at 25° C., and then unreacted thionyl chloride was distilled off under reduced pressure. Thus, salicylic acid chloride (9.8 g, 62.6 mmol) as an intermediate was obtained. Salicylic acid chloride (2.50 g, 16.0 mmol) thus obtained, Intermediate 6 (3.86 g, 18.35 mmol), and potassium carbonate (2.20 g, 15.91 mmol) were allowed to react for 12 hours in 100 mL of toluene, while the mixture was heated to reflux. After completion of the reaction, toluene was added thereto, and the mixture was subjected to washing with water, distillation of the solvent, and purification using a column. Thus, Compound 26 was obtained as a liquid.

FT-IR (KBr): 3229 cm$^{-1}$: O—H stretching vibration, 1694 cm$^{-1}$: C=O—O stretching vibration, 593 cm$^{-1}$: C—S stretching vibration $^1$H-NMR (CDCl$_3$ 400 MHz): δ 0.88 (t, 3H, CH$_3$(CH$_2$)$_5$—S), 1.29 (m, 4H, CH$_3$ (CH$_2$)$_2$(CH$_2$)$_3$—S), 1.45 (m, 2H, CH$_3$(CH$_2$)$_2$CH$_2$(CH$_2$)$_2$—S), 1.67 (quin, 2H, CH$_3$(CH$_2$)$_3$CH$_2$CH$_2$—S), 2.96 (t, 2H, CH$_3$ (CH$_2$)$_3$CH$_2$CH$_2$—S), 6.99 (m, 2H), 7.05 (d, 1H), 7.14 (s, 1H), 7.22 (d, 1H), 7.25 (t, 1H), 7.56 (t, 1H), 8.01 (d, 1H), (insg.8arom. CH), 10.47 (s, 1H, -Ph-OH)

$^{13}$C-NMR (CDCl$_3$ 400 MHz): δ 14.0 (CH$_3$(CH$_2$)$_5$—S), 22.5 (CH$_3$CH$_2$(CH$_2$)$_4$—S), 28.9 (CH$_3$CH$_2$ (CH$_2$)$_2$CH$_2$CH$_2$—S), 31.3 (CH$_3$(CH$_2$)$_3$CH$_2$CH$_2$—S), 33.3 (CH$_3$(CH$_2$)$_4$CH$_2$—S), 111.8, 118.6, 119.5, 121.2, 129.2, 130.3 (CH$_{arom}$), 117.9 (C$_{arom}$—C(=O)—O—), 139.5 (C$_{arom}$—S), 150.4 (—(O=)C—O—C$_{arom}$), δ 162.3 (C$_{arom}$—OH), δ 168.7 (C(=O)—)

<Synthesis Example 34> Synthesis of Compound 27

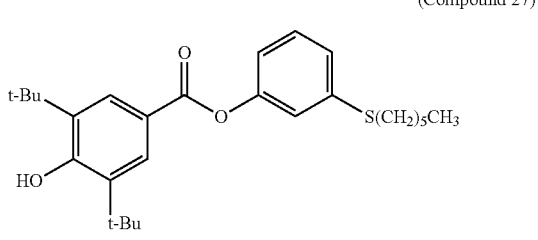
(Compound 27)

Compound 27 was synthesized by a synthesis method similar to that used for Compound 26, using 3,5-di-tert-butyl-4-hydroxybenzoic acid (16.0 g, 63.9 mmol).

FT-IR (KBr): 3622 cm$^{-1}$: O—H stretching vibration, 1732 cm$^{-1}$: C=O—O stretching vibration, 639 cm$^{-1}$: C—S stretching vibration $^1$H-NMR (CDCl$_3$ 400 MHz): δ 0.88 (t, 3H, CH$_3$(CH$_2$)$_5$—S), 1.29 (m, 4H, CH$_3$ (CH$_2$)$_2$(CH$_2$)$_3$—S), 1.43 (m, 2H, CH$_3$ (CH$_2$)$_2$ CH$_2$(CH$_2$)$_2$—S), 1.49 (s, 18H, -Ph-OH— (C(CH$_3$)$_3$)$_2$), 1.67 (quin, 2H, CH$_3$(CH$_2$)$_3$CH$_2$CH$_2$—S), 2.93 (t, 2H, CH$_3$(CH$_2$)$_3$CH$_2$CH$_2$—S), 5.77 (s, 1H, -Ph-OH—(C(CH$_3$)$_3$)$_2$), 6.98 (d, 1H), 7.13 (s, 1H), 7.17 (d, 1H), 7.30 (t, 1H), 8.04 (s, 2H) (insg.6arom. CH) $^{13}$C-NMR (CDCl$_3$ 400 MHz): δ 14.0 (CH$_3$(CH$_2$)$_6$—S), 22.5 (-Ph-OH—(C(CH$_3$)$_3$)$_2$)), 28.5 (CH$_3$CH$_2$(CH$_2$)$_4$—S), 28.9 (CH$_3$(CH$_2$)$_2$CH$_2$(CH$_2$)$_2$—S), 30.2 (-Ph-OH—(C(CH$_3$)$_3$)$_2$)), 31.3 (CH$_3$CH$_2$CH$_2$(CH$_2$)$_2$CH$_2$—S), 33.4 (CH$_3$(CH$_2$)$_3$CH$_2$CH$_2$—S), 34.1 (CH$_3$(CH$_2$)$_4$CH$_2$—S), 119.1, 120.3, 121.8, 127.8, 129.4 (CH$_{arom}$), 125.7 (C$_{arom}$—C(=O)—O—), 136.0 (—C$_{arom}$— (C(CH$_3$)$_3$)$_2$), 138.8 (C$_{arom}$—S), 151.5 (—(O=)C—O—C$_{arom}$), δ 158.8 (C$_{arom}$—OH), δ 165.5 (C(=O)—)

<Synthesis Example 35> Synthesis of Compound 28

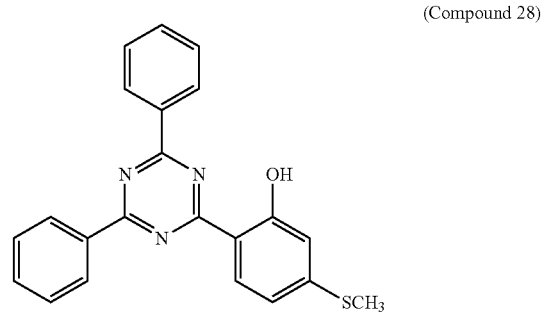
(Compound 28)

2-Chloro-4,6-diphenyl-1,3,5-triazine (1.92 g, 7.14 mmol) and aluminum chloride (2.37 g, 17.85 mmol) were reacted for 30 minutes at 25° C. in 50 mL of O-xylene, and then Intermediate 5 (2.00 g, 14.25 mmol) was added thereto. The mixture was allowed to react for 8 hours at 80° C. After completion of the reaction, toluene was added thereto, and the mixture was subjected to washing with water, distillation of the solvent, purification using a column, and recrystallization. Thus, Compound 28 was obtained.

FT-IR (KBr): 3064 cm$^{-1}$: O—H stretching vibration, 1568, 845 cm$^{-1}$: triazine ring stretching vibration, 602 cm$^{-1}$: C—S stretching vibration $^1$H-NMR (CDCl$_3$ 400 MHz): δ 2.41 (s, 3H, Ph-SCH$_3$), 6.71 (m, 2H), 7.47 (m, 6H), 8.47 (m, 5H) (insg.13arom. CH), 13.28 (s, 1H, Ph-OH)

$^{13}$C-NMR (CDCl$_3$ 400 MHz): δ 14.7 (Ph-SCH$_3$), 114.1 ((HO—)C$_{arom}$C$_{arom}$C(—N)=N), 113.2, 128.8, 129.0, 129.8, 133.0 (CH$_{arom}$), 148.2 (C$_{arom}$—SCH$_3$), 162.4 (C$_{arom}$—OH), 171.4 (N—(C$_{arom}$)—C=N).

67
<Synthesis Example 36> Synthesis of Compound 29

(Compound 29)

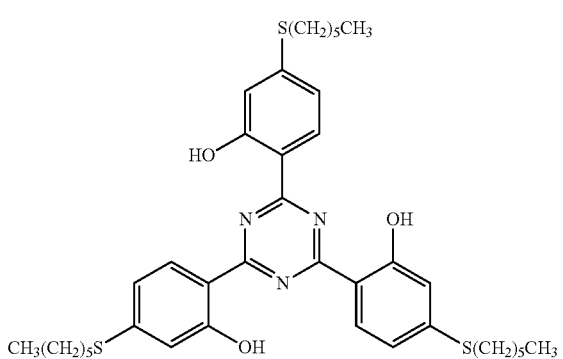

Cyanuric acid chloride (1.92 g, 7.14 mmol) and Intermediate 6 (6.75 g, 32.13 mmol) were heated to dissolve in 50 mL of 1,2-dichloroethane, and then the solution was cooled in ice. Aluminum chloride (0.95 g, 7.14 mmol) was added thereto over 30 minutes, and the mixture was allowed to react for 54 hours at 70° C. After completion of the reaction, toluene was added thereto, and the mixture was subjected to washing with water, distillation of the solvent, purification using a column, and recrystallization. Thus, Compound 29 was synthesized.

FT-IR (KBr): 3064 cm$^{-1}$: O—H stretching vibration, 1568, 846 cm$^{-1}$: triazine ring stretching vibration, 602 cm$^{-1}$: C—S stretching vibration $^1$H-NMR (CDCl$_3$ 400 MHz): δ 0.92 (t, 3H, C$\underline{H}_3$(CH$_2$)$_5$—S), 1.34 (m, 4H, CH$_3$ (C$\underline{H}_2$)$_2$(CH$_2$)$_3$—S), 1.47 (quin, 2H, CH$_3$ (CH$_2$)$_2$ C$\underline{H}_2$(CH$_2$)$_2$—S), 1.75 (quin, 2H, CH$_3$ (CH$_2$)$_3$ C$\underline{H}_2$CH$_2$—S), 3.02 (t, 2H, CH$_3$ (CH$_2$)$_3$CH$_2$C$\underline{H}_2$—S), 6.89 (d, 2H), 7.62 (m, 6H), 8.58 (d, 1H), 8.63 (m, 4H) (insg.13arom. C$\underline{H}$), 13.43 (s, 1H, Ph-O$\underline{H}$)

$^{13}$C-NMR (CDCl$_3$ 400 MHz): δ 14.0 ($\underline{C}$H$_3$(CH$_2$)$_5$—S), 22.5 (CH$_3$$\underline{C}$H$_2$(CH$_2$)$_4$—S), 28.6 (CH$_3$CH$_2$$\underline{C}$H$_2$ (CH$_2$)$_3$—S), 28.7 (CH$_3$(CH$_2$)$_2$$\underline{C}$H$_2$(CH$_2$)$_2$—S), 31.4 (CH$_3$(CH$_2$)$_3$$\underline{C}$H$_2$CH$_2$—S), 31.5 (CH$_3$(CH$_2$)$_4$$\underline{C}$H$_2$—S), 111.9 ($\underline{C}_{arom}$C=N), 114.1, 117.9, 128.5 ($\underline{C}$H$_{arom}$), 149.6 ($\underline{C}_{arom}$—S), 162.7 ($\underline{C}_{arom}$—OH), 168.4 (C$_{arom}$—$\underline{C}$=N).

<Synthesis Example 37> Synthesis of Compound 30

(Compound 30)

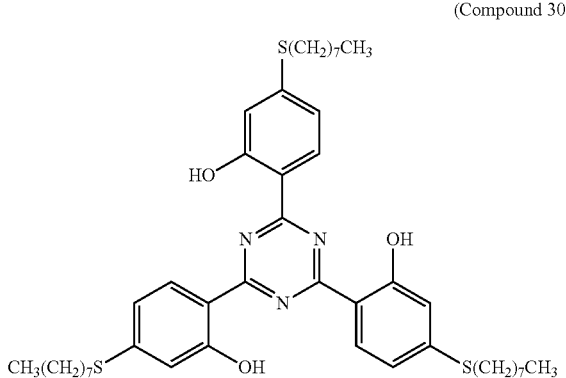

Compound 30 was synthesized by a synthesis method similar to that used for Compound 29, using Intermediate 7 (7.66 g, 32.13 mmol).

FT-IR (KBr): 2951 cm$^{-1}$: O—H stretching vibration, 1570, 843 cm$^{-1}$: triazine ring stretching vibration, 606 cm$^{-1}$: C—S stretching vibration $^1$H-NMR (CDCl$_3$ 400 MHz): δ 0.90 (t, 3H, C$\underline{H}_3$(CH$_2$)$_7$—S), 1.32 (m, 8H, CH$_3$(C$\underline{H}_2$)$_4$(CH$_2$)$_3$—S), 1.47 (quin, 2H, CH$_3$(CH$_2$)$_4$C$\underline{H}_2$(CH$_2$)$_2$—S), 1.72 (quin, 2H, CH$_3$(CH$_2$)$_5$C$\underline{H}_2$CH$_2$—S), 2.92 (t, 2H, CH$_3$(CH$_2$)$_6$C$\underline{H}_2$—S), 6.70 (d, 2H), 7.72 (d, 1H), (insg.13arom. C$\underline{H}$), 12.99 (s, 1H, Ph-O$\underline{H}$)

$^{13}$C-NMR (CDCl$_3$ 400 MHz): δ 14.1 ($\underline{C}$H$_3$(CH$_2$)$_7$—S), 22.7 (CH$_3$$\underline{C}$H$_2$(CH$_2$)$_6$—S), 28.6 (CH$_3$CH$_2$$\underline{C}$H$_2$(CH$_2$)$_5$—S), 29.2 (CH$_3$(CH$_2$)$_2$($\underline{C}$H$_2$)$_3$(CH$_2$)$_2$—S), 31.5 (CH$_3$(CH$_2$)$_5$$\underline{C}$H$_2$CH$_2$—S), 31.9 (CH$_3$(CH$_2$)$_6$$\underline{C}$H$_2$—S), 111.8 ($\underline{C}_{arom}$C=N), 113.9, 117.7, 128.4 ($\underline{C}$H$_{arom}$), 149.6 ($\underline{C}_{arom}$—S), 162.7 ($\underline{C}_{arom}$—OH), 168.2 (C$_{arom}$—$\underline{C}$=N)

<Synthesis Example 38> Synthesis of Compound 31

(Compound 31)

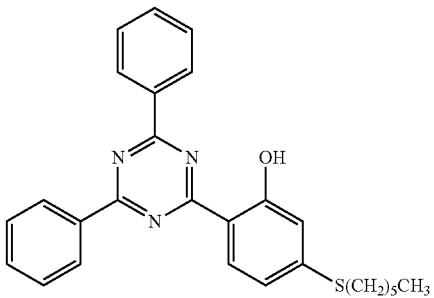

Compound 31 was synthesized by a synthesis method similar to that used for Compound 28, using Intermediate 6 (2.0 g, 8.38 mmol). The properties values are shown below.

FT-IR (KBr): 33064 cm$^{-1}$: O—H stretching vibration, 1568, 846 cm$^{-1}$: triazine ring stretching vibration, 602 cm$^{-1}$: C—S stretching vibration $^1$H-NMR (CDCl$_3$ 400 MHz): δ 0.90 (t, 3H, C$\underline{H}_3$(CH$_2$)$_5$—S), 1.34 (m, 2H, CH$_3$ (C$\underline{H}_2$)$_2$(CH$_2$)$_3$—S), 1.47 (quin, 2H, CH$_3$ (CH$_2$)$_2$ C$\underline{H}_2$(CH$_2$)$_2$—S), 1.75 (quin, 2H, CH$_3$ (CH$_2$)$_3$ C$\underline{H}_2$CH$_2$—S), 3.03 (t, 2H, CH$_3$ (CH$_2$)$_3$CH$_2$C$\underline{H}_2$—S), 6.89 (d, 2H), 7.62 (m, 6H), 8.58 (d, 1H), 8.63 (m, 4H) (insg.13arom. C$\underline{H}$), 13.43 (s, 1H, Ph-O$\underline{H}$)

$^{13}$C-NMR (CDCl$_3$ 400 MHz): δ 14.0 ($\underline{C}$H$_3$(CH$_2$)$_5$—S), 22.5 (CH$_3$$\underline{C}$H$_2$(CH$_2$)$_4$—S), 28.7 (CH$_3$CH$_2$$\underline{C}$H$_2$ (CH$_2$)$_3$—S), 28.8 (CH$_3$(CH$_2$)$_2$$\underline{C}$H$_2$(CH$_2$)$_2$—S), 31.4 (CH$_3$(CH$_2$)$_3$$\underline{C}$H$_2$CH$_2$—S), 31.8 (CH$_3$(CH$_2$)$_4$$\underline{C}$H$_2$—S), 114.3 ((HO—)C$\underline{C}_{arom}$C(—N)=N), 117.9, 129.0, 129.9, 133.0 ($\underline{C}$H$_{arom}$), 135.3 ($\underline{C}_{arom}$—C=N), 147.4 ($\underline{C}_{arom}$—S), 162.3 ($\underline{C}_{arom}$—OH), 171.4 (C$_{arom}$—$\underline{C}$=N).

Meanwhile, Compound 5 was a compound manufactured by Sigma-Aldrich Company; Compound 32 was a compound manufactured by BASF SE; Compound 33 was a compound manufactured by Tokyo Chemical Industry Co., Ltd.; Compound 34 was a compound manufactured by Wako Pure Chemical Industries, Ltd.; Compound 35 was a compound manufactured by Sigma-Aldrich Company; and Compound 36 was a compound manufactured by Tokyo Chemical Industry Co., Ltd.

Evaluation results for the melting points, film external appearance, and refractive indices of the compounds of Examples and Comparative Examples are presented in Table 1 to Table 8, and the ultraviolet-visible transmission spectra of the compounds of Examples are presented in FIG. 1 to FIG. 8.

1. Evaluation of Compounds (1) Melting Point

Melting points of the compounds of Examples and Comparative Examples 2 to 4 were measured by visual observation (liquid or solid) at room temperature (25° C.), or using a micro-melting point apparatus (MP-3 manufactured by Yanako Co., Ltd.) or a differential scanning calorimeter (DSC6220 manufactured by Seiko Instruments Inc.) (Tables 1 to 7).

In benzotriazole compounds each having a thiol group, when the number of carbon atoms of the functional group —$(CH_2)_n$—SH was from 1 to 10, the melting point became 35° C. or lower (Compounds 1 and 2). For compounds containing a thioether group in a phenyl group ($R^{1a}$ to $R^{5a}$) in benzotriazole (Compounds 3 and 4) in regard to benzotriazole compounds, and for compounds containing a thioether group in benzophenone (Compounds 24 and 25) and salicylate-based compounds (Compounds 26 and 27), the maximum number of carbon atoms in the functional group —$(CH_2)_n$—S—, —S—$(CH_2)_n$—S—, or —S—$(CH_2)_n CH_3$ was 8 or less. Thus, it was confirmed that the melting point was 35° C. or lower, the compounds were liquid at normal temperature, and there was a correlation between the number of carbon atoms and the melting point, regardless of having a benzotriazole skeleton, a benzophenone skeleton, or a salicylate skeleton. On the other hand, in regard to benzotriazole-based compounds each having a thioether group composed of a linear saturated aliphatic hydrocarbon group in the benzotriazole group ($R^{6a}$ to $R^{9a}$) (Compounds 6 to 14), compounds in which the maximum number of carbon atoms in the functional group —$(CH_2)_n$—S—, —S—$(CH_2)_n$—S—, or —S—$(CH_2)_n CH_3$ is 18 or less (Compounds 6 to 14) have melting points of 91° C. or lower; however, there is no clear correlation between the number of carbon atoms and the melting point, and it is difficult to lower the melting point.

Furthermore, when compared to Compound 32 having an ether group (—O—), Compound 3 having a thioether group (—S—) had a low melting point and was liquid at normal temperature. Furthermore, compared to Compounds 6 to 13 each having one thioether group, Compound 14 having two thioether groups had a lower melting point, so that a tendency of lowering the melting point by introduction of thioether was confirmed.

On the other hand, triazine-based Compound 28 had an increased melting point by having a sulfur-containing group introduced thereinto, and thus it was suggested that the compound had excellent heat resistance.

(2) Refractive Index

For Compounds 1, 2, 3, 4, 5, 25, 26, and 27 having melting points of 25° C. or lower, the refractive indices were measured at 20° C.; and for Compound 14 having a relatively low melting point (46° C.) and Compound 24 (34° C.), the refractive indices were measured after the compounds were heated, using an Abbe refractometer (NAR-2T manufactured by Atago Co., Ltd.) in all cases. Also, for Comparative Examples 2, 3 and 4 (Compounds 32, 33 and 34), the catalogue values provided by the manufacturers are described in the tables.

In regard to benzotriazole-based compounds, Compounds 1 to 4 and 14 had higher refractive indices compared to Compounds 5 and 32; in regard to benzophenone-based compounds, Compounds 24 and 25 had higher refractive indices compared to Compound 33; and in regard to salicylate-based compounds, Compounds 26 and 27 had higher refractive indices compared to Compound 34. Thus, an effect of imparting a high refractive index by introducing a sulfur-containing group was confirmed.

(3) 5% Weight Reduction Temperature

For Compounds 6 to 21, 23, 24, 27, 29, 30, 31, 33, 34, 35 and 36, measurement was performed in a measurement range of 25° C. to 550° C. at a temperature increasing temperature of 10° C./min, using a thermogravimetric/differential thermal analyzer (manufactured by Seiko Instruments Inc., TG/DTA 6200), and thus the temperature at which weight change (TG) occurred as reduction by 5 weight % was read.

In benzotriazole-based compounds having thioether groups composed of saturated and unsaturated hydrocarbon groups (Compounds 6 to 17), aromatic groups (Compounds 18 and 19), and oxygen-containing hydrocarbon groups (Compound 20) and a bis-form (Compound 21), heat resistance was increased by introducing thioether groups (suppressing deterioration of the ultraviolet absorbency and the ability of increasing refractive index of resin members, and deterioration of transparency of transparent resins, caused by thermal decomposition of ultraviolet absorbers). Also, their 5% weight reduction degradation temperatures were higher than the values of 2-(2-hydroxy-3-t-butyl-5-methylphenyl)chlorobenzotriazole (Compound 36, 5% weight reduction temperature: 230° C.) and Compound 5 (5% weight reduction temperature: 249° C.), which do not have sulfur-containing groups and are generally used as ultraviolet absorbers for long wavelength absorption, and their 5% weight reduction temperatures were 252° C. or higher. Similarly, also in regard to benzophenone and salicylate-based compounds, benzophenone-based compounds 23 (5% weight reduction temperature: 279° C.) and 24 (5% weight reduction temperature: 260° C.) had 5% weight reduction temperatures of 260° C. or higher and had enhanced heat resistance, compared to Compound 33 having no thioether group (5% by weight reduction temperature: 249° C.); and salicylate-based compound 27 (5% weight reduction temperature: 264° C.) had a 5% weight reduction degradation temperature of 260° C. or higher and had enhanced heat resistance, compared to Compound 34 having no thioether group (5% weight reduction temperature: 249° C.). That is, the 5% weight reduction temperatures of Compounds 6 to 21, 23, 24, and 27 were higher than 100° C. to 250° C., in which range the softening points of most general resins fall ("Well-Known Plastics", reviewed by Japan Plastics Industry Federation, published by Nippon Jitsugyo Publishing Co., Ltd.), and generally, the molding processing temperature of 100° C. to 200° C. can be applied to thermosetting resins and thermoplastic resins which require molding processing temperatures higher than 200° C. to 250° C., as well as thermosetting resins of which molding processing temperatures are general range of 100° C. to 200° C. Thus, deterioration of the ultraviolet absorbency and the ability of increasing refractive index of a resin member and transparency of a transparent resin member can be suppressed.

Also, in regard to triazine-based compounds, as compared to Compound 35 having no thioether group (5% weight reduction temperature: 319° C.), Compound 29 (5% weight reduction temperature: 369° C.), Compound 30 (5% weight reduction temperature: 372° C.), and Compound 31 (5% weight reduction temperature: 336° C.), all having thioether groups introduced thereinto, had increased 5% weight reduction temperatures as a result of introducing thioether groups, and had enhanced heat resistance (deterioration of the ultraviolet absorbency and the ability of increasing refractive index of a resin member and deterioration of transparency of a transparent resin, all caused by thermal decomposition of an ultraviolet absorber, were suppressed). Thus, it was confirmed that their compounds having thioether group is applicable to thermoplastic resins which require molding processing temperatures higher than 200° C. to 250° C.

(4) Ultraviolet Absorption

Each of Compounds 1 to 5, 8, 10, 11, 14, and 22 to 35 was diluted with chloroform to 5 μM, and the dilution was accommodated in a 10-mm quartz cell. The absorption spectrum was measured using an ultraviolet-visible spectrophotometer (V-550 manufactured by JASCO Corp.) (FIGS. 1, 2 and 6 to 8). Furthermore, Compounds 6 to 21 and 36 were measured in the same manner using chloroform at 100 μM (FIGS. 3 to 5).

From each of the absorption spectra (100 μM) of Compounds 8, 10, 11, 14, 21, and 36, an intersection point between the absorption spectrum on the long wavelength side for an absorption peak at 350 to 390 nm and the baseline (a line having a slope of 0 in the absorption spectrum at 430 to 500 nm) was designated as a peak end (e.g.: FIG. 3, Example 47), and thereby an absolute value of the slope on the long wavelength side of the absorption peak in the wavelength region of 350 to 390 nm was determined by the formula described below (Table 9). Similarly, also for each of Compounds 6, 7, 9, 12, 13, and 15 to 20, an absolute value of the slope on the long wavelength side of the absorption peak in the wavelength region of 350 to 390 nm was determined from the absorption spectrum. The absolute values are presented in Tables 2 and 4.

|Slope on long wavelength side of absorption peak in wavelength region of 350 to 390 nm|=|(Absorbance of peak end−absorbance of absorption peak in wavelength region of 350 to 390 nm)/ (absorption wavelength of peak end−wavelength of absorption peak in wavelength region of 350 to 390 nm)|

The absolute values of the slopes for Compounds 6 to 21 were all 0.030 or more, and were larger than the absolute value of Compound 36 having no thioether group (absolute value of the slope on the long wavelength side of the absorption peak in the wavelength region of 350 to 390 nm: 0.0219), while the peaks were sharp. Thus, it was suggested that the compounds have an effect of suppressing yellowing in films, resin members, and particularly transparent resin members.

Furthermore, in regard to Compound 21, the molar absorption coefficient was large, and when measurement was made at 100 μM, the absorbance exceeded the measurement range. Therefore, as shown in Table 10, the absorption peaks were measured at concentrations of 10, 25, and 50 μM, and the absolute value of the slope on the long wavelength side of the absorption peak in the wavelength region of 350 to 390 nm was plotted against the concentration of the ultraviolet absorber. As shown in FIG. 9, in a linear first-order relation, the absolute value of the slope at 100 μM of Compound 21 was calculated by the equation of the graph (Y=0.0006X−0.0024). As a result, the slope of Compound 21 at 100 μM was 0.0576, and this was larger than the slopes of other compounds. It was considered that Compound 21 had a superior effect of suppressing yellowing in a film, a resin member, and particularly a transparent resin member.

From the absorption spectra of Compounds 6 to 21 and 36, the absorption peak (maximum absorption wavelength: $\lambda_{max}$) in the wavelength region of 350 to 390 nm and the absorbance were read, and the molar absorption coefficient (maximum molar absorption coefficient: $\varepsilon_{max}$) of the peak was determined by the following formula (Table 11).

Molar absorption coefficient: $\varepsilon_{max}$ (L/(mol·cm)=$A$: absorbance/[$c$: molar concentration (mol/L)×$l$: light path length of cell (cm)]

As a result, since Compounds 6 to 21 had thioether introduced thereinto, the molar absorption coefficients were as high as 17,000 or higher compared to Compound 36, and it was found that ultraviolet ray is efficiently absorbed by addition of small amounts of the compounds. Particularly, Compound 21 in a bis-form is considered to have a higher molar absorption coefficient than Compounds 6 to 20, and has superior effects.

It was confirmed that all of the compounds of the present invention have absorption bands in the wavelength region of ultraviolet ray, and function as ultraviolet absorbers when added to films and resins.

It was confirmed that benzotriazole-based Compounds 6 to 21 of the present invention, in which the thioether group of (i-2) has been introduced into a benzotriazole group, has ultraviolet absorbency that enables absorption of ultraviolet ray in the vicinity of 360 to 400 nm, which is a longer wavelength region even within the UV-A region (320 to 400 nm) without cutting 420 to 500 nm (visible range), i.e. without yellowing, which ability is absent in Comparative Example 9 (Compound 32) and 2-(2-hydroxy-3-t-butyl-5-methylphenyl)chlorobenzotriazole (Comparative Example 10, Compound 36, FIGS. 3 to 5) that has been conventionally used as an ultraviolet absorber for long wavelength absorption. Furthermore, in Compounds 1, 2, 3 and 4, in which the thioether group of (i-2) has been introduced into the phenyl group on a nitrogen atom of a benzotriazole-based compound, the absorption peak top rather significantly shifted to a short wavelength region (270 to 290 nm), compared to Compound 32 of Comparative Example 9. That is, for benzotriazole-based compounds, the UV absorption peak region was adjustable by means of the position of the thioether group.

It was confirmed that owing to these characteristics, in Examples 71 to 77 (FIGS. 10 to 16), when a small amount of the additive of the present invention is added to a plastic lens, absorption of wavelengths near 420 nm or longer is suppressed while efficiently absorbing light having a wavelength in the vicinity of 400 to 420 nm, which corresponds to harmful light, and thus an effect of suppressing yellowing of the plastic lens is obtained.

Also in regard to triazine-based Compounds 28 to 31, it was confirmed that by having the substituent of (iv-2) introduced into the compounds, the absorption peak tops significantly shift to a long wavelength region compared to Comparative Example 13 (Compound 35), and the compounds can absorb ultraviolet ray in the vicinity of 360 to 400 nm of a long wavelength region without cutting visible light (450 to 500 nm). Furthermore, it was confirmed that triazine-based Compounds 28 and 31 each have an absorption peak even in a region of short wavelength ultraviolet ray (260 to 280 nm) in addition to the absorption peak top of a longer wavelength region (in the vicinity of 360 to 400 nm), and are capable of absorbing ultraviolet ray in a wide region.

2. Evaluation of Film

Compatibility (transparency) of the compounds of the present invention with films and resin members, and the effect of the compounds of imparting a high refractive index were checked by methods described below (Tables 1 to 8).

(Production of Acrylic Film)

The following three kinds of films having different film thicknesses, to which the compounds of Examples 1 to 14 and 22 to 29, and Comparative Examples 2 and 3 had been added, were produced.

A sample having a film thickness of 50 to 300 nm was produced by uniformly mixing 0.1 g of each of the compounds of Examples 1 to 14 and 22 to 27 and Comparative Examples 2 and 3, with 0.1 g of an acrylic resin (manufactured by Mitsubishi Rayon Co., Ltd.) and 12 g of chloroform, spin coating about 1 mL of the mixture on a glass substrate under the conditions of 1,500 rpm and 20 seconds, and subsequently removing the solvent for 2 hours in an oven at 45° C.

A sample having a film thickness of 301 to 1,500 nm was produced by uniformly mixing 0.1 g of each of the compounds of Examples 1 to 14 and 22 to 27 and Comparative Examples 2 and 3, with 0.1 g of an acrylic resin and 4 g of chloroform, spin coating about 1 mL of the mixture on a glass substrate under the conditions of 1,500 rpm and 20 seconds, and subsequently removing the solvent for 2 hours in an oven at 45° C.

A sample having a film thickness of 10 to 150 μm was produced by uniformly mixing 0.1 g of each of the compounds of Examples 1 to 14 and 22 to 27 and Comparative Examples 2 and 3, with 0.1 g of an acrylic resin and 4 g of chloroform, subsequently concentrating chloroform to about 2 to 3 g, dropping this on a slide glass, and then removing the solvent for 2 hours in an oven at 45° C.

For Example 28 (film thickness: 50 to 300 nm, 301 to 1,500 nm, and 10 to 150 μm) and Example 29 (film thickness: 50 to 300 nm, and 301 to 1,500 nm), a similar operation was carried out by changing the blend of the compound and the resin to 0.03 g and 0.07 g, respectively.

Furthermore, a film was produced by uniformly mixing 0.1 g of an acrylic resin with 4 g or 12 g of chloroform without adding an additive, and performing an operation similar to that described above (Comparative Example 1).

(Production of Urethane Film)

0.022 g of an isocyanate (HC-210 manufactured by Nippon Polyurethane Industry Co., Ltd.), 0.078 g of a polyol (ON-H37 manufactured by Nippon Polyurethane Industry Co., Ltd.), and 0.1 g of each of the compounds of Examples 1, 3 to 13, 22 and 24 to 27, and Comparative Example 2 were uniformly mixed with 12 g of chloroform for a sample having a film thickness of 50 to 300 nm, or with 4 g of chloroform for a sample having a film thickness of 301 to 1,500 nm, and about 1 mL of the mixture was spin coated on a glass substrate under the conditions of 1,500 rpm and 20 seconds. Subsequently, chloroform was removed therefrom in an oven at 45° C., and then the sample was heated for 3 hours at 100° C. Thus, a urethane film was produced.

A sample having a film thickness of 10 to 150 m was produced by uniformly mixing 0.1 g of each of the compounds of Examples 4, 5, 8 and 26 and Comparative Example 2, 0.022 g of an isocyanate, 0.078 g of a polyol, and 4 g of chloroform, subsequently concentrating about 2 to 3 g of chloroform, dropping this on a slide glass, subsequently removing the solvent for 2 hours in an oven at 45° C., and then heating the sample for 3 hours at 100° C.

For Example 28 (film thickness: 50 to 300 nm, 301 to 1,500 nm, and 10 to 150 m), the blend of the compound and the resin was changed to 0.03 g and 0.07 g (isocyanate 0.015 g, polyol 0.055 g), and an operation similar to that described above was carried out.

Furthermore, 0.022 g of an isocyanate, 0.078 of a polyol, and 4 g or 12 g of chloroform were uniformly mixed without adding an additive, and an operation similar to that described above was carried out. Thus, a film was produced (Comparative Example 1).

(Production of Thiourethane Film)

0.430 g of Compound 6, 0.1 g of ZELEC UN manufactured by Stepan Company, 0.04 g of dibutyltin dichloride, and 50.8 g of a mixture of 2,5-bis(isocyanatomethyl)-bicyclo[2.2.1]heptane and 2,6-bis(isocyanatomethyl)-bicyclo[2.2.1]heptane were introduced into a flask, and the mixture was completely dissolved by stirring for 1 hour at 25° C. Subsequently, 22.4 g of pentaerythritol tetrakis(3-mercaptopropionate) and 26.8 g of 1,2-bis[(2-mercaptoethyl)thio]-3-mercaptopropane were added to the mixed liquid, and the resultant was mixed for 30 minutes at 25° C. Compound 6 in the preparation liquid was included at a proportion of 0.430% by weight with respect to the total weight of polymerizable compounds.

This preparation liquid was subjected to degassing for one hour at 0.3 mmHg or lower, and filtration was performed using a 5-μm PTFE filter. The preparation liquid was poured into a mold die formed from a glass mold for flat plate having a center thickness of 2 mm and a diameter of 80 mm and a tape. This mold was slowly heated from 25° C. to 130° C., maintained at 130° C. for 2 hours, and then cooled to room temperature. The time taken from the initiation of temperature increase to cooling was 18 hours. After completion of polymerization, a molded product thus obtained was released from the mold, and annealing was performed for 2 hours at 130° C.

Furthermore, thiourethane films were obtained by a method similar to that used for Compound 6, except that instead of Compound 6, the ultraviolet absorber to be added was changed to 0.472 g of Compound 7, 0.490 g of Compound 8, 0.533 g of Compound 9, 0.555 g of Compound 10, 0.651 g of Compound 11, 0.580 g of Compound 12, and 0.600 g of Compound 13, respectively, while the same molar concentration was used.

In the thiourethane film to which Compound 13 was added, crystals were precipitated out, and clouding occurred; however, the thiourethane films to which Compounds 6 to 12 were added were transparent without having crystals precipitated out.

(Production of Polyethylene Terephthalate Film: PET)

For samples to which the additive was added at a proportion of 5 wt %, a film having a thickness of 20 to 200 μm was produced by kneading 0.0418 g of polyethylene terephthalate chips with 0.0022 g of each compound of Compounds 1, 3, 5 to 13, 25 and 28 (Examples 6 to 13 and 30 to 35) and Compounds 32, 33 and 35 (Comparative Examples 6 to 8) at 280° C., dropping this mixture on a slide glass substrate, quickly spreading the mixture thereon, and air-cooling the mixture.

For samples to which the additive was added at a proportion of 10 wt %, a film having a thickness of 20 to 200 μm was produced by kneading 0.0450 g of polyethylene terephthalate chips with 0.005 g of each compound of Compounds 1, 3, 5 to 13, 25 and 28 (Examples 6 to 13 and 30 to 35) and Compounds 32, 33 and 35 (Comparative Examples 6 to 8) at 280° C., dropping this mixture on a slide glass substrate, quickly spreading the mixture thereon, and air-cooling the mixture.

For samples to which the additive was added at a proportion of 20 wt %, a film having a thickness of 20 to 200 μm was produced by kneading 0.0352 g of polyethylene terephthalate chips with 0.0088 g of each compound of Compounds 1, 3, 5, 8, 25 and 28 (Examples 30 to 35) and Compounds 32, 33 and 35 (Comparative Examples 6 to 8) at 280° C., dropping this mixture on a slide glass substrate, quickly spreading the mixture thereon, and air-cooling the mixture.

For samples to which the additive was added at a proportion of 30 wt %, a film having a thickness of 20 to 200 µm was produced by kneading 0.0566 g of polyethylene terephthalate chips with 0.0244 g of each compound of Compounds 1, 3, 5, 8, 25 and 28 (Examples 30 to 35) and Compounds 32, 33 and 35 (Comparative Examples 6 to 8) at 280° C., dropping this mixture on a slide glass substrate, quickly spreading the mixture thereon, and air-cooling the mixture.

Furthermore, a film having a thickness of 20 to 200 µm was produced by melting 0.045 g of polyethylene terephthalate chips without adding any additive, and performing an operation similar to that described above (Comparative Examples 1 and 5).

(Production of Polystyrene Film: PS)

Films having a film thickness of 10 to 50 m, to which the compounds of Examples 6 to 13, 15 to 18, and 20 had been added, were produced by the procedure described below.

A film was produced (50 wt %) by uniformly mixing 0.1 g of each of the compounds of Examples 6 to 13, 15 to 18 and 20, 0.1 g of a polystyrene resin (Kanto Chemical Co., Inc.), and 4 g of chloroform, subsequently concentrating about 2 to 3 g of chloroform, dropping 50 µL of this concentrate on a slide glass, and then removing the solvent for 2 hours in an oven at 45° C.

Furthermore, for Compounds 19 and 21, a film was produced by performing an operation similar to that described above, by uniformly mixing a blend (10 wt %) of 0.0111 g of Compounds 19 or 21, 0.1 g of a polystyrene resin (Kanto Chemical Co., Inc.), and 2 g of chloroform. For a blank film of Comparative example 1, a film was produced by performing an operation similar to that described above, by uniformly mixing 0.1 g of a polystyrene resin and 4 g of chloroform without adding any additive thereto.

(Production of Polycarbonate Film: PC)

Films having a film thickness of 10 to 50 km, to which the compounds of Examples 6 to 13, 15 to 18, and 20 had been added, were produced by the procedure described below.

A film was produced (40 wt %) by uniformly mixing 0.0667 g of each of the compounds of Examples 6 to 13, 15 to 18, and 20, 0.1 g of a polycarbonate resin (Kanto Chemical Co., Inc.), and 4 g of chloroform, subsequently concentrating about 2 to 3 g of chloroform, dropping 25 µL of this on a slide glass, and removing the solvent for 2 hours in an oven at 45° C.

In regard to Compound 19, a film was produced by uniformly mixing a blend of 0.011 g of Compound 19, 0.1 g of a polycarbonate resin (Kanto Chemical Co., Inc.), and 2 g of chloroform (10 wt %). In regard to Compound 21, a film was produced by uniformly mixing a blend of 0.025 g of Compound 21, 0.1 g of a polycarbonate resin (Kanto Chemical Co., Inc.), and 4 g of chloroform (20 wt %). A blank film of Comparative Example 1 was produced by uniformly mixing 0.1 g of a polycarbonate resin and 4 g of chloroform without adding an additive, and performing an operation similar to that described above.

(Production of Urea Resin Film)

Films having a film thickness of 40 to 80 km, to which Compounds of Examples 6 to 13 were added, were produced by the procedure described below.

1 mL of a 37 wt % formaldehyde solution, 0.25 g of urea, and 0.16 g of ammonium acetate were dissolved, and thus a monomer solution was produced. Next, 0.0007 g of each of the compounds of Examples 6 to 13 was dissolved in 0.2 mL of THF, and the solution was uniformly mixed with 0.1 mL of the monomer solution. 0.3 ml of the mixture was applied on a slide glass having a size of 1.5×1.5 cm. Then, this slide glass was placed in an oven, and temperature was raised from room temperature to 150° C. over 30 minutes. Subsequently, the applied mixture was allowed to react for 5 hours at 150° C., and thus a film was produced.

Furthermore, a blank film for comparison was produced by uniformly mixing 0.1 mL of the monomer solution with 0.2 mL of THF without adding an additive, and performing an operation similar to that described above (Comparative Example 1).

(Production of Melamine Resin Film)

Films having a film thickness of 10 to 50 µm, to which the compounds of Examples 6 to 13 were added, were produced by the procedure described below.

To 5.15 g of a formaldehyde solution that had been conditioned to pH 7.5 with sodium hydroxide, 1 g of melamine and 24.60 g of water were added, and the mixture was allowed to react under heating. Thus, a hexamethylolmelamine solution was produced. Next, 0.0057 g of each of the compounds of Examples 6 to 13 was dissolved in 0.1 mL of THF, and the solution was uniformly mixed with 0.2 ml of the hexamethylolmelamine solution. 0.3 mL of the mixture was applied on a slide glass having a size of 1.5×1.5 cm. Then, this slide glass was placed in an oven, and temperature was raised from room temperature to 150° C. over 30 minutes. Subsequently, the applied mixture was allowed to react for 5 hours at 150° C., and thus a film was produced.

Furthermore, a blank film for comparison was produced by uniformly mixing 0.2 ml of the monomer solution with 0.1 ml of THF without adding an additive, and performing an operation similar to that described above (Comparative Example 1).

(Production of Acrylic Melamine Resin Film)

Films having a film thickness of 100 to 150 m, to which the compounds of Examples 6 to 13 were added, were produced by the procedure described below.

0.0045 g of each of the compounds of Examples 6 to 13 was dissolved in 0.1 mL of THF such that when the solution was produced into a film, the concentration of the compound would be 10 wt %, and the solution was uniformly mixed with 0.1 mL of a baking and drying type top coat paint (baking and drying type top coat (acrylic melamine): ACRYCITE UB-63 CLEAR manufactured by Saito Paint Co., Ltd.). 0.2 mL of the mixture was applied on a slide glass having a size of 1.5×1.5 cm. Then, this slide glass was placed in an oven, and temperature was raised from room temperature to 150° C. over 30 minutes. Subsequently, the applied mixture was allowed to react for 2 hours at 150° C., and thereby, an acrylic melamine resin film containing 10 wt % of an additive was obtained.

Furthermore, a blank film for comparison was produced by uniformly mixing 0.1 mL of an acrylic melamine monomer with 0.1 mL of THF without adding an additive, and performing an operation similar to that described above (Comparative Example 1).

(1) External Appearance

The external appearance of a film was visually observed, and was evaluated according to the following criteria.

Evaluation Criteria (Acrylic Film, Urethane Film, and Thiourethane Film)

○: Transparent without cloudiness.

x: Cloudiness is observed, and transparency is poor.

Evaluation Criteria (PET Film)
◎: Having equivalent transparency compared to the blank of Comparative Example.
◯: Having very slight cloudiness compared to the blank of Comparative Example.
Δ: Having slight cloudiness compared to the blank of Comparative Example.
x: Having obvious cloudiness compared to the blank of Comparative Example.

Evaluation Criteria (PS Film)
◯: Having equivalent transparency compared to the blank of Comparative Example.
Δ: Having slight cloudiness compared to the blank of Comparative Example.
x: Having obvious cloudiness compared to the blank of Comparative Example.

Evaluation Criteria (PC Film)
◯: Having equivalent transparency compared to the blank of Comparative Example.
Δ: Having slight cloudiness compared to the blank of Comparative Example.
x: Having obvious cloudiness compared to the blank of Comparative Example.

Evaluation Criteria (Urea Resin Film)
◯: Transparent without precipitation of crystals.
Δ: Slight precipitation of crystals is observed, but transparent.
x: Precipitation of crystals is observed, and transparency is poor.

Evaluation Criteria (Melamine Resin Film)
◯: Transparent without precipitation of crystals.
x: Precipitation of crystals is observed, and transparency is poor.

Evaluation Criteria (Acrylic Melamine Resin Film)
◯: Transparent without precipitation of crystals.
Δ: Partial precipitation of crystals is observed, and transparency is poor.
x: Precipitation of crystals is generally observed, and transparency is poor.

The conditions for the alkyl chain, melting point, and the sulfur-containing group of the additive were in agreement, and therefore, compatibility of the thermoplastic resins with an acrylic film (transparentization) was enhanced.

Regarding the alkyl chain, the films having a thickness of 50 to 300 nm became transparent, for compounds a having a thiol group, when the numbers of carbon atoms of the functional groups —$(CH_2)_n$—SH and —$(CH_2)_n CH_3$ were respectively 9 or less (Compounds 1 and 22); and for compounds having a thioether group, when the numbers of carbon atoms of the functional groups —$(CH_2)_n$—S—, —S—$(CH_2)_n$—S—, and —S—$(CH_2)_n CH_3$ were respectively 17 or less (Compounds, 3, 4, 6 to 10, 12 to 14, and 23 to 29). Furthermore, in regard to compounds having a thioether group, generally, when compounds having the aforementioned number of carbon atoms of 8 or less were used, even thicker films having a film thickness of 301 to 1,500 nm also became transparent (Compounds 3, 4, 7, 8, 12, 14, and 23 to 27). That is, it was confirmed that the number of carbon atoms is important for compatibility with a resin (transparency), and a compound having an alkyl chain with a length of from a medium chain to a short chain tends to have enhanced phase dissolution properties (transparentization).

In regard to benzotriazole, benzophenone, and salicylate-based compounds, generally, there was a correlation between the melting point and the compatibility with a resin, in addition to the correlation with the alkyl chain as described above. Thus, when melting point was lowered, phase dissolution properties (transparentization) were enhanced. Compounds having a melting point of 91° C. or lower (Compounds 1, 3, 4, 5, 6 to 10, 12 to 14, and 22 to 27) generally transparentized films having film a thickness of 50 to 300 nm, despite high proportions of addition of 50%. Furthermore, compounds having a melting point of below 70° C. (Compounds 1, 3, 4, 5, 7, 8, 9, 14 and 23 to 27) transparentized thicker films having a thickness of 301 to 1,500 nm, and compounds having a melting point of 35° C. or lower (liquid at normal temperature) (Compounds 1, 3, 4 and 24 to 27) realized transparentization even at a larger thickness of 10 to 150 m.

However, in acrylic films having a thickness of 10 to 150 μm, other Compounds 3 and 4 having a melting point of 35° C. or lower and having a sulfur-containing group transparentized an acrylic film, whereas Compound 5 having no sulfur-containing group caused clouding in an acrylic film despite having a melting point of 25° C. or lower.

On the other hand, Compounds 6 to 10, 12 and 13 obtained by introducing a sulfur-containing group into 2-(2-hydroxy-3-t-butyl-5-methylphenyl)-chlorobenzotriazole (Comparative Example 10, Compound 36) as a raw material, transparentized urethane films having a film thickness of 50 to 300 nm, whereas 2-(2-hydroxy-3-t-butyl-5-methylphenyl)-chlorobenzotriazole (Comparative Example 10, Compound 36) that did not have a sulfur-containing group caused clouding. Thus, it was suggested that introduction of a sulfur-containing group was one of requirements for compatibility (transparency) with a resin.

After all, Compound 33 having no sulfur-containing group has a low melting point of 47° C. to 48° C. compared to Compound 22 having a melting point of 91° C. and Compound 23 having a melting point of 60.5° C. to 69° C.; however, while Compounds 22 and 23 transparentized acrylic films having a film thickness of 50 to 300 nm, Compound 33 clouded an acrylic film. That is, it was suggested that not only the melting point, but also the presence of a sulfur-containing group enhance phase dissolution properties (transparentization) for a resin.

Furthermore, Compound 2 (number of carbon atoms: 10) having a thiol has a melting point of 25° C. or lower, and Compound 11 (number of carbon atoms: 18) having a thioether has a melting point of 73° C. to 83° C. However, despite that the melting point was 91° C. or lower, acrylic films having a thickness of 50 to 300 nm were not transparentized. That is, it is speculated that it is also important to satisfy the requirements of both the melting point and the number of carbon atoms, and since Compounds 2 and 11 have 10 carbon atoms and 18 carbon atoms, respectively, which are larger numbers of carbon atoms than the number of carbon atoms defined above (compound having a thiol group: number of carbon atoms being 9 or less, compound having a thioether group: number of carbon atoms being 17 or less), and the condition for the number of carbon atoms is not satisfied, the acrylic films were not transparentized.

Urethane resins, which are thermosetting resins, also had the same tendency, and exhibited satisfactory transparency as a result of the effects of the alkyl chain, melting point, and sulfur-containing group of the additives of the present invention.

Also for Compounds 1, 3, 8, 25 and 28 of the present invention, the additives of the present invention having a sulfur-containing group introduced thereinto exhibited satisfactory heat resistance (5% weight reduction temperature: Compound 8: 295° C., Compound 5: 249° C.) and satisfactory transparency with high compatibility with PET resins, which are thermoplastic resins, at a heated molding temperature of 280° C. under the conditions of high concentration and a high film thickness of 20 to 200 µm, compared to Compounds 5, 32, 33 and 35, as a result of the effects of the alkyl chain, melting point, and sulfur-containing group as described above (Table 8).

In regard to Compounds 6 to 13 having a group of Formula (i-2) for $R^{7a}$ or $R^{8a}$ of Formula (I), for an evaluation (Tables 2 and 3) of compatibility (transparency) with the various resins indicated in Tables 2 and 3 (acrylic (50 to 300 nm, 301 to 1,500 nm, and 10 to 150 am), urethane (50 to 300 nm, and 301 to 1,500 nm), thiourethane, PET (5, 10 wt), PS, PC, urea, melamine, and acrylic melamine), the number of the most satisfactory ratings (acrylic, urethane, thiourethane, PS, PC, urea, melamine, and acrylic melamine: ○, PET: ⊙), and the number of poorest ratings (acrylic, urethane, thiourethane, PET, PS, PC, urea, melamine, and acrylic melamine: x) were counted, and comprehensive compatibility of the various compounds with resins (transparency) was evaluated according to the criteria of Table 12. The results are presented in Table 13.

As a result, compounds that obtained a rating of 1 or higher were compounds having a number of carbon atoms of $R^{13a}$ of 1 to 18 and having a melting point of 91° C. or lower (Compounds 6, 7, 8, 9, 10, 11, 12 and 13); compounds that obtained a rating of 2 or higher were compounds having a number of carbon atoms of $R^{13a}$ of 1 to 12 and having a melting point of 91° C. or lower (Compounds 6, 7, 8, 9, 10, 12 and 13); compounds that obtained a rating of 3 or higher were compounds having a number of carbon atoms of $R^{13a}$ of 1 to 10 and having a melting point of 91° C. or lower (Compounds 6, 7, 8, 9 and 12), or compounds having a number of carbon atoms of $R^{13a}$ of 1 to 12, having a melting point of 91° C. or lower, and having a methyl group and a t-butyl group as the substituents for $R^{2a}$ and $R^{4a}$ (Compounds 6, 7, 8, 9 and 10); compounds that obtained a rating of 4 or higher were compounds having a number of carbon atoms of $R^{13a}$ of 1 to 12, having a melting point of 91° C. or lower, and having a methyl group and a t-butyl group as the substituents for $R^{2a}$ and $R^{4a}$ (Compounds 6, 7, 8, 9 and 10); and compounds that obtained a rating of 5 or higher were compounds having a number of carbon atoms of $R^{13a}$ of 4 to 10, having a melting point of 91° C. or lower, and having a methyl group and a t-butyl group as the substituents for $R^{2a}$ and $R^{4a}$ (Compounds 6, 7, 8 and 9); and compounds that obtained a rating of 6 or higher were compounds having a number of carbon atoms of $R^{13a}$ of 6 to 10, having a melting point of below 70° C., and having a methyl group and a t-butyl group as the substituents for 2a and 4a (Compounds 7, 8 and 9). Compatibility (transparency) with a resin serving as a matrix was dependent not only on any one of the number of carbon atoms of the alkyl of Formula (i-2) in the benzotriazole skeleton of Formula (I) as the structure of the additive, and the melting point of the compound, but was dependent on both of them (Compound 12 (number of carbon atoms: 8, melting point: 80° C. to 81° C.) having a number of carbon atoms of 10 or less but having a melting point of 70° C. or higher: Rating 3; and Compound 13 (number of carbon atoms: 12, melting point: 64° C. to 66° C.) having a melting point of below 70° C. but having a number of carbon atoms of 10 or more: Rating 2, indiscriminately did not obtain satisfactory ratings).

Furthermore, similarly to the number of carbon atoms of $R^{13a}$, Compound 8 in which the substituents for $R^{1a}$ to $R^{5a}$ are different (number of carbon atoms of $R^{13a}$: 8, substituents for 2a and 4a: methyl group, t-butyl group) and Compound 12 (number of carbon atoms of $R^{13a}$: 8, substituents for $R^{2a}$, $R^{4a}$: t-butyl group, t-butyl group) are compared, and Compound 10 (number of carbon atoms of $R^{13a}$: 12, substituents for $R^{2a}$, $R^{4a}$: methyl group, t-butyl group) and Compound 13 (number of carbon atoms of $R^{13a}$: 12, substituents for $R^{2a}$, $R^{4a}$: t-butyl group, t-butyl group) are compared, Compound 8 showed satisfactory compatibility (transparency) in PET, which is a thermoplastic resin, and in urea, melamine and acrylic melamine resin, which are thermosetting resins, compared to Compound 12; and Compound 10 showed satisfactory compatibility (transparency) in thiourethane and PET, which are thermoplastic resins, and in melamine and acrylic melamine, which are thermosetting resins, compared to Compound 13 (FIG. 17). Compound 8 and Compound 10 also had higher points for the above-described ratings. That is, in regard to compatibility (transparency) with a resin, compounds having a methyl group and a t-butyl group as the substituents for $R^{2a}$ and $R^{4a}$ generally tend to be satisfactory, and compounds having a number of carbon atoms of $R^{13a}$ of 12 or less (Compounds 6, 7, 8, 9 and 10), even compounds having the number of carbon atoms of 4 to 10 (Compounds 6, 7, 8 and 9), and particularly Compounds 7, 8 and 9 having the number of carbon atoms of 6 to 10, exhibited satisfactory compatibility (transparency) with all resins, irrespective of being thermosetting resins or thermoplastic resins, such as acrylic, urethane, thiourethane, PET, PS, PC, urea, and melamine.

Furthermore, Compounds 15 to 21 having a thioether group, which have a branched aliphatic hydrocarbon group, a cyclic aliphatic hydrocarbon group, an alkene group-containing aliphatic hydrocarbon group, an aromatic group, an oxygen-containing aliphatic hydrocarbon group, and the like, also exhibited compatibility (transparency) with PS and PC, and thus the effects of the introduction of a sulfur-containing group, the melting point and the like were suggested.

(2) Film Thickness

The film thickness was measured at a cross-section generated by cutting a film, using a tabletop microscope (MINI-SCOPE TM3000 manufactured by Hitachi High-Technologies Corp.), or the reflectance of a film was measured using a reflectance meter (USPM-RU manufactured by Olympus Corp.), and the film thickness was obtained by analyzing the reflectance waveform thus obtained, through fitting using Hartmann dispersion formula.

(3) Refractive Index

The refractive index of a film was determined by measuring from the single-surface reflectance (λ=589 nm) (Tables 1, 2, 5, 6 and 7).

Acrylic resin films to which the compounds of the present invention were added (Compounds 1, 3, 4, 5, 8, 10, 14, 22, 23, 24, 25, 26, 27 and 28: refractive indices 1.5178 to 1.5914) acquired higher refractive indices than the non-added film of Comparative Example 1 (1.4985). Compared to Compound 5 having no sulfur-containing group, Compounds 1, 3, 4, 8, 10 and 14 each having a sulfur-containing groups had high refractive indices, and thus an effect of the present invention of imparting a high refractive index provided by the compounds of the present invention having sulfur-containing groups was suggested.

From these results, it was confirmed that the compounds of Examples cut the wavelengths in the ultraviolet region in the vicinity of 250 to 400 nm, and transmit the wavelengths of 450 to 500 nm (visible range). Particularly, it was confirmed that the compounds of Examples have excellent ultraviolet absorbency for 315 to 400 nm (UV-A region), which may affect photodegradation of organic substances, and cut ultraviolet ray even up to the region near 400 nm. Therefore, the additives of the present invention can prevent deterioration or discoloration of a resin serving as a matrix, and are useful. Furthermore, an effect of increasing the refractive index of a resin film was also recognized. It was also confirmed that even if the additive is added in an amount of 0.4 wt % to 50 wt % with respect to the sum of the amounts of the resin and the additive, the film remains transparent without discoloration, and that the compounds of Examples have high solubility in a resin and can be used in high concentrations while maintaining transparency.

TABLE 1

| Example or Comparative Example No. | Compound No. | Structure | Additive Appearance (35° C.) | Additive Melting point ° C. | Additive Refractive index (20° C.) | Acrylic 50~300 nm Appearance | Acrylic 50~300 nm Film thickness (nm) | Acrylic 50~300 nm Refractive index (589 nm) | Acrylic 301~1500 nm Appearance | Acrylic 301~1500 nm Film thickness (nm) |
|---|---|---|---|---|---|---|---|---|---|---|
| Comparative Example 1 | | No additive | | | | ○ | 72 | 1.4985 | ○ | 1050 |
| Example 1 | 1 | Benzotriazole with O(CH₂)₆SH and Me substituents | Liquid | ≤25 | 1.6043 | ○ | 78 | 1.5378 | ○ | 981 |
| Example 2 | 2 | Benzotriazole with O(CH₂)₁₀SH and Me substituents | Liquid | ≤25 | 1.5980 | X | 78 | — | X | 761 |
| Example 3 | 3 | Benzotriazole with HO and S(CH₂)₃CH₃ substituents | Liquid | ≤25 | 1.6138 | ○ | 295 | 1.5677 | ○ | 1125 |
| Example 4 | 4 | Benzotriazole with HO and S(CH₂)₂(SCH₃)₂CH₃ substituents | Liquid | ≤25 | 1.6131 | ○ | 210 | 1.5657 | ○ | 1251 |
| Example 5 | 5 | Benzotriazole with HO, (CH₂)₁₁CH₃ and Me substituents | Liquid | ≤25 | 1.5735 | ○ | 74 | 1.5288 | ○ | 876 |
| Comparative Example 2 | 32 | Benzotriazole with HO and O(CH₂)₂CH₃ substituents | Solid | 75–76.5 | 1.595 | X | 77 | — | X | 856 |

| Example or Comparative Example No. | Acrylic 10~150 μm Appearance | Acrylic 10~150 μm Film thickness (μm) | Urethane 50~300 nm Appearance | Urethane 50~300 nm Film thickness (nm) | Urethane 301~1500 nm Appearance | Urethane 301~1500 nm Film thickness (nm) | Urethane 10~150 μm Appearance | Urethane 10~150 μm Film thickness (μm) |
|---|---|---|---|---|---|---|---|---|
| Comparative Example 1 | ○ | 29 | ○ | 179 | ○ | 677 | ○ | 16 |
| Example 1 | ○ | 21 | ○ | 116 | ○ | 553 | — | — |

TABLE 1-continued

| | | | | | | | | |
|---|---|---|---|---|---|---|---|---|
| Example 2 | X | 28 | — | — | — | — | — | |
| Example 3 | ○ | 27 | ○ | 258 | ○ | 383 | — | — |
| Example 4 | ○ | 75 | ○ | 191 | ○ | 591 | ○ | 44 |
| Example 5 | X | 37 | ○ | 241 | ○ | 345 | X | 29 |
| Comparative Example 2 | X | 29 | X | 121 | X | 331 | X | 25 |

TABLE 2

| Example or Comparative Example No. | Compound No. | Structure | Resin Additive Appearance (35° C.) | Melting point ° C. | Refractive index (20° C.) | Absolute value of slope on longer wavelength side of absorption peak in wavelength region of 350 to 390 nm | 5% weight reduction temperature (° C.) | Acrylic Additive concentration 50 wt % 50~300 nm Appearance | Film thickness (nm) | Refractive index (589 nm) |
|---|---|---|---|---|---|---|---|---|---|---|
| Comparative Example 1 | | No additive | | | | | | ○ | 72 | 1.4985 |
| Example 6 | 6 | benzotriazole with CH$_3$(CH$_2$)$_3$S— substituent, 2-(2-hydroxy-3-t-Bu-5-Me-phenyl) | Solid | 87 | — | 0.0369 | 260 | ○ | 261 | — |
| Example 7 | 7 | benzotriazole with CH$_3$(CH$_2$)$_8$S— substituent, 2-(2-hydroxy-3-t-Bu-5-Me-phenyl) | Solid | 69 | — | 0.0363 | 277 | ○ | 252 | — |
| Example 8 | 8 | benzotriazole with CH$_3$(CH$_2$)$_7$S— substituent, 2-(2-hydroxy-3-t-Bu-5-Me-phenyl) | Solid | 50~63 | — | 0.0355 | 294 | ○ | 204 | 1.5664 |
| Example 9 | 9 | benzotriazole with CH$_3$(CH$_2$)$_9$S— substituent, 2-(2-hydroxy-3-t-Bu-5-Me-phenyl) | Solid | 68~69 | — | 0.0367 | 303 | ○ | 263 | — |

TABLE 2-continued

| Example | # | Structure | State | Temp | | Value | Value2 | Appearance | Value3 | Value4 |
|---|---|---|---|---|---|---|---|---|---|---|
| Example 10 | 10 | benzotriazole with CH₃(CH₂)₁₁S substituent; phenol with HO, t-Bu, Me | Solid | 70~72 | — | 0.0358 | 315 | ○ | 224 | 1.5377 |
| Example 11 | 11 | benzotriazole with CH₃(CH₂)₁₇S substituent; phenol with HO, t-Bu, Me | Solid | 73~83 | — | 0.0365 | 305 | X | 75 | — |
| Example 12 | 12 | benzotriazole with CH₃(CH₂)₇S substituent; phenol with HO, t-Bu, t-Bu | Solid | 80~81 | — | 0.0372 | 294 | ○ | 267 | — |
| Example 13 | 13 | benzotriazole with CH₃(CH₂)₁₁S substituent; phenol with HO, t-Bu, t-Bu | Solid | 64~66 | — | 0.0376 | 307 | ○ | 270 | — |
| Example 14 | 14 | benzotriazole with CH₃(CH₂)₇S(CH₂)₃S substituent; phenol with HO, t-Bu, Me | Solid | 40~45 | 1.6019 (46° C.) | 0.0345 | 293 | ○ | 240 | 1.5531 |

| Example or Comparative Example No. | Acrylic Additive concentration: 50 wt % | | | | Urethane Additive concentration: 50 wt % | | | | | | Thiourethane |
|---|---|---|---|---|---|---|---|---|---|---|---|
| | 301~1500 nm | | 10~150 μm | | 50~300 nm | | 301~1500 nm | | 10~150 μm | | — |
| | Appearance | Film thickness (nm) | Appearance | Film thickness (μm) | Appearance | Film thickness (nm) | Appearance | Film thickness (nm) | Appearance | Film thickness (μm) | 2 mm Appearance |
| Comparative Example 1 | ○ | 1050 | ○ | 29 | ○ | 179 | ○ | 677 | ○ | 16 | ○ |
| Example 6 | X | 1231 | X | 35 | ○ | 228 | X | 1050 | — | — | ○ |
| Example 7 | ○ | 1209 | X | 72 | ○ | 264 | X | 1348 | — | — | ○ |
| Example 8 | ○ | 1348 | X | 21 | ○ | 288 | ○ | 1100 | X | 20 | ○ |

TABLE 2-continued

| | | | | | | | | | | | |
|---|---|---|---|---|---|---|---|---|---|---|---|
| Example 9 | ○ | 1343 | X | 40 | ○ | 260 | ○ | 1301 | — | — | ○ |
| Example 10 | X | 943 | X | 42 | ○ | 224 | ○ | — | — | — | ○ |
| Example 11 | X | 1236 | X | 92 | X | 75 | X | — | — | — | ○ |
| Example 12 | ○ | 1208 | X | 81 | ○ | 229 | ○ | 1020 | — | — | ○ |
| Example 13 | X | 1280 | X | 55 | ○ | 240 | ○ | 996 | — | — | X (Crystals precipitated) |
| Example 14 | ○ | 1354 | X | 86 | — | — | — | — | — | — | — |

TABLE 3

| | | | PET | | | |
|---|---|---|---|---|---|---|
| | | | Additive concentration 5 wt % | | Additive concentration 10 wt % | |
| | | | 20~200 μm | | | |
| Example or Comparative Example No. | Compound No. | Structure | Appearance | Film thickness (μm) | Appearance | Film thickness (μm) |
| Comparative Example 1 | | No additive | ⊙ | 104 | ⊙ | 29 |
| Example 6 | 6 | benzotriazole with CH$_3$(CH$_2$)$_3$S– substituent and 2-(2-hydroxy-3-t-Bu-5-Me-phenyl) group | ⊙ | 128 | ○ | 127 |
| Example 7 | 7 | benzotriazole with CH$_3$(CH$_2$)$_5$S– substituent and 2-(2-hydroxy-3-t-Bu-5-Me-phenyl) group | ⊙ | 114 | ○ | 84 |
| Example 8 | 8 | benzotriazole with CH$_3$(CH$_2$)$_7$S– substituent and 2-(2-hydroxy-3-t-Bu-5-Me-phenyl) group | ⊙ | 110 | ○ | 110 |

TABLE 3-continued

| Example 9 | 9 | 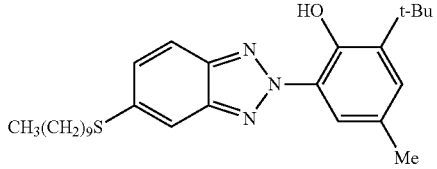 | ⊙ | 120 | ○ | 136 |
| Example 10 | 10 | 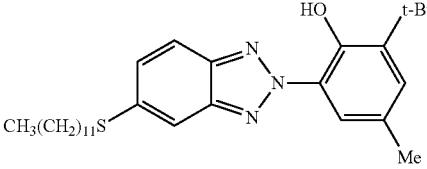 | ⊙ | 114 | X | 64 |
| Example 11 | 11 | 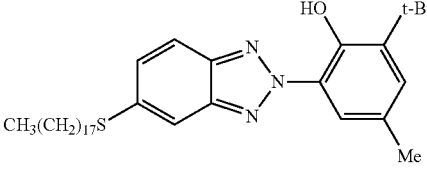 | ○ | 89 | X | 97 |
| Example 12 | 12 | 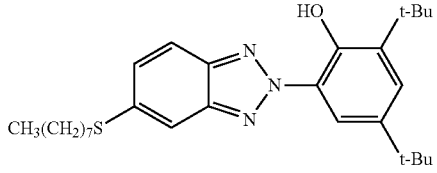 | ○ | 194 | X | 96 |
| Example 13 | 13 | 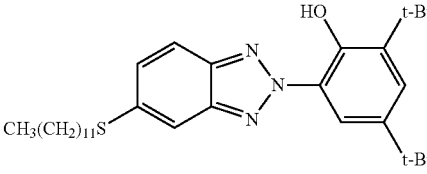 | ○ | 115 | X | 83 |

| | PS Additive concentration: 50 wt % 10~50 μm | | PC Additive concentration: 40 wt % 10~50 μm | | Urea Additive concentration: 1 wt % 40~80 μm | | Melamine Additive concentration: 30 wt % 10~50 μm | | Acrylic melamine Additive concentration: 10 wt % 100~150 μm | |
|---|---|---|---|---|---|---|---|---|---|---|
| Example or Comparative Example No. | Appearance | Film thickness (μm) | Appearance | Film thickness (μm) | Appearance | Film thickness (μm) | Appearance | Film thickness (μm) | Appearance | Film thickness (μm) |
| Comparative Example 1 | ○ | 14 | ○ | 13 | ○ | 75 | ○ | 19 | ○ | 115 |
| Example 6 | ○ | 47 | ○ | 19 | ○ | 58 | ○ | 46 | ○ | 111 |
| Example 7 | ○ | 35 | ○ | 17 | ○ | 46 | ○ | 26 | ○ | 125 |
| Example 8 | ○ | 22 | ○ | 39 | ○ | 60 | ○ | 27 | ○ | 129 |
| Example 9 | ○ | 38 | ○ | 18 | ○ | 54 | ○ | 24 | ○ | 119 |
| Example 10 | Δ | 41 | Δ | 23 | Δ | 46 | ○ | 45 | ○ | 127 |
| Example 11 | X | 34 | X | 16 | X (Crystals precipitated) | 54 | X (Crystals precipitated) | 41 | X | 114 |
| Example 12 | ○ | 28 | ○ | 19 | X (Crystals precipitated) | 72 | X (Crystals precipitated) | 15 | Δ | 128 |
| Example 13 | Δ | 29 | Δ | 25 | X (Crystals precipitated) | 55 | X (Crystals precipitated) | 17 | X | 113 |

TABLE 4

| Example or Comparative Example No. | Compound No. | Structure | Resin Additive Appearance (35° C.) | Melting point ° C. | Refractive index (20° C.) | Absolute value of slope on longer wavelength side of absorption peak in wavelength region of 350 to 390 nm | 5% weight reduction temperature (° C.) | PS Additive concentration 50 wt % 10~50 μm Appearance | PS Film thickness (μm) | PC Additive concentration 40 wt % 10~50 μm Appearance | PC Film thickness (μm) |
|---|---|---|---|---|---|---|---|---|---|---|---|
| Comparative Example 1 | | No additive | | | | | | ○ | 14 | ○ | 13 |
| Example 15 | 15 | [structure: benzotriazole with t-Bu, Me, OH substituents and S–CH(C2H5)(CH3) group] | Solid | 81~82 | — | 0.0359 | 259 | ○ | 25 | ○ | 16 |
| Example 16 | 16 | [structure: benzotriazole with t-Bu, Me, OH substituents and S–cyclohexyl group] | Solid | 141~142 | — | 0.0359 | 283 | ○ | 16 | △ | 24 |
| Example 17 | 17 | [structure: benzotriazole with t-Bu, Me, OH substituents and S–allyl group] | Solid | 162~167 | — | 0.0321 | 252 | ○ | 35 | △ | 22 |

TABLE 4-continued

| Example or Comparative Example No. | Compound No. | Structure | Resin Additive | | | | | PS Additive concentration 50 wt % 10–50 μm | | PC Additive concentration 40 wt % 10–50 μm | |
|---|---|---|---|---|---|---|---|---|---|---|---|
| | | | Appearance (35° C.) | Melting point ° C. | Refractive index (20° C.) | Absolute value of slope on longer wavelength side of absorption peak in wavelength region of 350 to 390 nm | 5% weight reduction temperature (° C.) | Appearance | Film thickness (μm) | Appearance | Film thickness (μm) |
| Example 18 | 18 | [structure: benzotriazole with t-Bu, Me, HO substituents on phenol ring and S-C6H4-CH3 group] | Solid | 140–142 | — | 0.0373 | 293 | ○ | 29 | Δ | 28 |
| Example 19 | 19 | [structure: benzotriazole with t-Bu, Me, HO substituents on phenol ring and S-CH2-C6H5 group] | Solid | 129–132 | — | 0.0340 | 287 | ○ (10 wt %) | 17 | ○ (10 wt %) | 19 |

TABLE 4-continued

| Example or Comparative Example No. | Compound No. | Structure | Resin Additive | | | | | PS Additive concentration 50 wt % 10~50 μm | | PC Additive concentration 40 wt % 10~50 μm | |
|---|---|---|---|---|---|---|---|---|---|---|---|
| | | | Appearance (35° C.) | Melting point ° C. | Refractive index (20° C.) | Absolute value of slope on longer wavelength side of absorption peak in wavelength region of 350 to 390 nm | 5% weight reduction temperature (° C.) | Appearance | Film thickness (μm) | Appearance | Film thickness (μm) |
| Example 20 | 20 | 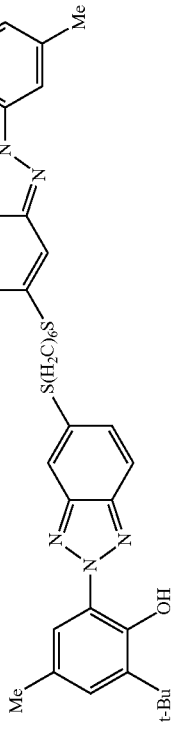 | Solid | 71~75 | — | 0.0324 | 281 | X | 32 | ◯ | 13 |
| Example 21 | 21 | 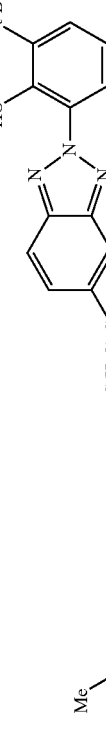 | t-Bu Solid | 187~190 | — | 0.0576 | 329 | △ (10 wt %) | 18 | ◯ (20 wt %) | 15 |

TABLE 5

| Example or Comparative Example No. | Compound No. | Structure | Additive Appearance (35° C.) | Melting point ° C. | Refractive index (20° C.) | 5% weight reduction temperature (° C.) | Acrylic 50~300 nm Appearance | Film thickness (nm) |
|---|---|---|---|---|---|---|---|---|
| Example 22 | 22 | Benzophenone with 2-OH and 4-SH | Solid | 91 | — | — | ○ | 220 |
| Example 23 | 23 | 4-(CH$_3$(CH$_2$)$_7$S)-4'-OH benzophenone | Solid | 60.5~69 | — | 279 | ○ | 237 |
| Example 24 | 24 | 2-OH-4-(S(CH$_2$)$_3$S(CH$_2$)$_7$CH$_3$) benzophenone | Liquid | 30~34 | 1.5940 (34° C.) | 260 | ○ | 75 |
| Example 25 | 25 | 4-(CH$_3$(CH$_2$)$_7$S(CH$_2$)$_3$S)-4'-OH benzophenone | Liquid | ≤25 | 1.6151 | — | ○ | 242 |
| Comparative Example 3 | 33 | 2-OH-4-(O(CH$_2$)$_7$CH$_3$) benzophenone | Solid | 47~48 | 1.547 | 249 | X | 70 |

| Example or Comparative Example No. | Acrylic 50~300 nm Refractive index (589 nm) | Acrylic 301~1500 nm Appearance | Acrylic 301~1500 nm Film thickness (nm) | Acrylic 10~150 μm Appearance | Acrylic 10~150 μm Film thickness (μm) | Urethane 50~300 nm Appearance | Urethane 50~300 nm Film thickness (nm) | Urethane 301~1500 nm Appearance | Urethane 301~1500 nm Film thickness (nm) | Urethane 10~150 μm Appearance | Urethane 10~150 μm Film thickness (μm) |
|---|---|---|---|---|---|---|---|---|---|---|---|
| Example 22 | 1.5910 | X | 987 | X | 22 | ○ | 258 | — | — | — | — |
| Example 23 | 1.5627 | ○ | 893 | X | 87 | — | — | — | — | — | — |

TABLE 5-continued

| | | | | | | | | | | | |
|---|---|---|---|---|---|---|---|---|---|---|---|
| Example 24 | 1.5914 | ○ | 1231 | ○ | 20 | ○ | 182 | ○ | 330 | — | — |
| Example 25 | 1.5364 | ○ | 1081 | ○ | 144 | ○ | 278 | ○ | 504 | — | — |
| Comparative Example 3 | — | X | 821 | X | 21 | — | — | — | — | — | — |

TABLE 6

| Example or Comparative Example No. | Compound No. | Structure | Additive Appearance (35° C.) | Melting point ° C. | Refractive index (20° C.) | 5% weight reduction temperature (° C.) | Acrylic 50~300 nm Appearance | Film thickness (nm) |
|---|---|---|---|---|---|---|---|---|
| Example 26 | 26 | ![structure: 2-hydroxybenzoate of 3-(hexylthio)phenol] | Liquid | ≤25 | 1.58 | — | ○ | 189 |
| Example 27 | 27 | ![structure: 3,5-di-t-Bu-4-hydroxybenzoate of 3-(hexylthio)phenol] | Liquid | ≤25 | 1.557 | 264 | ○ | 227 |
| Comparative Example 4 | 34 | ![structure: 3,5-di-t-Bu-4-hydroxybenzoate of 2,4-di-t-Bu-phenol] | Solid | 191~192.5 | 1.52 | 249 | — | — |

TABLE 6-continued

| Example or Comparative Example No. | Acrylic 50~300 nm Refractive index (589 nm) | Acrylic 301~1500 nm Appearance | Acrylic 301~1500 nm Film thickness (nm) | Acrylic 10~150 μm Appearance | Acrylic 10~150 μm Film thickness (μm) | Urethane 50~300 nm Appearance | Urethane 50~300 nm Film thickness (nm) | Urethane 301~1500 nm Appearance | Urethane 301~1500 nm Film thickness (nm) | Urethane 10~150 μm Appearance | Urethane 10~150 μm Film thickness (μm) |
|---|---|---|---|---|---|---|---|---|---|---|---|
| Example 26 | 1.5477 | ○ | 821 | ○ | 129 | ○ | 178 | ○ | 680 | ○ | 80 |
| Example 27 | 1.5340 | ○ | 833 | ○ | 114 | ○ | 111 | ○ | 504 | — | — |
| Comparative Example 4 | — | — | — | — | — | — | — | — | — | — | — |

TABLE 7

| Example or Comparative Example No. | Compound No. | Structure | Additive Appearance (35° C.) | Additive Melting point ° C. | Additive Refractive index (20° C.) | Acrylic 50~300 nm Appearance | Acrylic 50~300 nm Film thickness (nm) | Acrylic 50~300 nm Refractive index (589 nm) |
|---|---|---|---|---|---|---|---|---|
| Example 28 | 28 | (structure: 2,4-diphenyl-6-(2-hydroxy-4-(methylthio)phenyl)-1,3,5-triazine) | Solid | 190~192 | — | | 278 | 1.5178 |
| Example 29 | 29 | (structure: 2,4,6-tris(2-hydroxy-4-(hexylthio)phenyl)-1,3,5-triazine) | Solid | 123.5~126 | — | | 288 | — |

TABLE 7-continued

| Example or Comparative Example No. | Acrylic | | | | Urethane | | | | | |
|---|---|---|---|---|---|---|---|---|---|---|
| | 301~1500 nm | | 10~150 µm | | 50~300 nm | 301~1500 nm | | 10~150 µm | | |
| | Appearance | Film thickness (nm) | Appearance | Film thickness (µm) | Appearance | Film thickness (nm) | Appearance | Film thickness (nm) | Appearance | Film thickness (µm) |
| Example 28 | ○ | 805 | X | 28 | ○ | 222 | X | 800 | X | 44 |
| Example 29 | X | 1456 | — | — | — | — | — | — | — | — |

TABLE 8

| Example or Comparative Example No. | Compound No. | Structural formula | PET | | | |
|---|---|---|---|---|---|---|
| | | | 5 wt % Appearance | 10 wt % Appearance | 20 wt % Appearance | 30 wt % Appearance |
| Comparative Example 5 | | PET only | ⊙ | ⊙ | ⊙ | ⊙ |
| Example 30 | 1 | benzotriazole with O(CH$_2$)$_6$SH and Me substituents | ⊙ | ⊙ | Δ | Δ |
| Example 31 | 3 | benzotriazole with HO and S(CH$_2$)$_7$CH$_3$ substituents | ⊙ | ⊙ | Δ | Δ |
| Example 32 | 8 | benzotriazole with HO, t-Bu, CH$_3$(CH$_2$)$_7$S, and Me substituents | ⊙ | ⊙ | Δ | X |
| Example 33 | 5 | benzotriazole with HO, (CH$_2$)$_{11}$CH$_3$, and Me substituents | ⊙ | ○ | X | X |
| Comparative Example 6 | 32 | benzotriazole with HO and O(CH$_2$)$_7$CH$_3$ substituents | ⊙ | ○ | X | X |

TABLE 8-continued

| Example or Comparative Example No. | Compound No. | Structural formula | PET 5 wt % Appearance | 10 wt % Appearance | 20 wt % Appearance | 30 wt % Appearance |
|---|---|---|---|---|---|---|
| Example 34 | 25 | CH₃(CH₂)₇S(CH₂)₃S—C₆H₄—C(O)—C₆H₄—OH | ⊙ | ⊙ | Δ | Δ |
| Comparative Example 7 | 33 | 2-hydroxy-4-octyloxybenzophenone | ⊙ | ○ | X | X |
| Example 35 | 28 | 2-(2-hydroxy-4-methylthiophenyl)-4,6-diphenyl-1,3,5-triazine | ⊙ | ⊙ | ○ | Δ |
| Comparative Example 8 | 35 | 2-(2-hydroxy-4-hexyloxyphenyl)-4,6-diphenyl-1,3,5-triazine | ○ | Δ | X | X |

TABLE 9

| | Absorbance of absorption peak in wavelength region of 350 to 390 nm | Absorbance of peak end | Absorption wavelength of peak end nm | Absolute value of slope on longer wavelength side of absorption peak in wavelength region of 350 to 390 nm |
|---|---|---|---|---|
| Compound 8 | 2.13704 | 0.00147 | 426.0 | 0.0365 |
| Compound 10 | 2.09328 | 0.00089 | 426.0 | 0.0358 |
| Compound 11 | 2.08832 | 0.00909 | 424.0 | 0.0365 |
| Compound 14 | 2.05024 | 0.00023 | 425.5 | 0.0345 |
| Compound 21 | 2.15433 | 0.00023 | 425.5 | 0.0368 |
| Compound 36 | 1.52567 | 0.00517 | 423.0 | 0.0219 |

*Compound 36: 2-(2-Hydroxy-3-t-butyl-5-methylphenol)-chlorobenzotriazole

TABLE 10

| Concentration | Absorbance of absorption peak in wavelength region of 350 to 390 nm | Absorbance of peak end | Absorption wavelength of peak end nm | Wavelength of absorption peak in wavelength region of 350 to 390 nm (Maximum absorption wavelength: $\lambda_{max}$) | Absolute value of slope on longer wavelength side of absorption peak in wavelength region of 350 to 390 nm |
|---|---|---|---|---|---|
| 10 μM | 0.21585 | 0.00013 | 427.5 | 367.0 | 0.00357 |
| 25 μM | 0.7874 | 0.00343 | 427.0 | 367.0 | 0.01307 |
| 50 μM | 1.69356 | 0.00541 | 427.0 | 367.0 | 0.02814 |

TABLE 11

| | Molecular weight g/mol | Wavelength of absorption peak in wavelength region of 350 to 390 nm (Maximum absorption wavelength: $\lambda_{max}$) nm | Molar absorption coefficient of peak described on left side (Maximum molar absorption coefficient: $\varepsilon_{max}$) L/(mol·cm) |
|---|---|---|---|
| Compound 6 | 370 | 367.0 | 22200 |
| Compound 7 | 398 | 367.0 | 22200 |
| Compound 8 | 426 | 367.5 | 21400 |
| Compound 9 | 454 | 367.5 | 22300 |
| Compound 10 | 482 | 367.5 | 20900 |
| Compound 11 | 566 | 367.0 | 20800 |
| Compound 12 | 468 | 366.5 | 22400 |
| Compound 13 | 523 | 366.5 | 22100 |
| Compound 14 | 500 | 366.0 | 20400 |
| Compound 15 | 369 | 367.0 | 21100 |
| Compound 16 | 396 | 367.5 | 21100 |
| Compound 17 | 353 | 375.0 | 17600 |
| Compound 18 | 404 | 369.0 | 21500 |
| Compound 19 | 404 | 366.0 | 20100 |
| Compound 20 | 357 | 364.0 | 19800 |
| Compound 21 | 709 | 367.0 | 43100 |
| Compound 36 | 316 | 353.5 | 15300 |

TABLE 12

| Evaluation | 6 | 5 | 4 | 3 | 2 | 1 |
|---|---|---|---|---|---|---|
| ○ + ⊙ | 10 or more | 9 or more | 7 or more | 7 or more | 3 or more | 1 or more |
| X | 2 or fewer | 3 or fewer | 3 or fewer | 4 or fewer | 7 or fewer | 11 or fewer |

TABLE 13

| Compound No. | Structure | Number of carbon atoms of $R^{13a}$ | Melting point | ⊙ and ○ | X | Evaluation |
|---|---|---|---|---|---|---|
| 6 | HO, t-Bu, benzotriazole with CH₃(CH₂)₃S– substituent, Me | 4 | 87 | 9 | 3 | 5 |
| 7 | HO, t-Bu, benzotriazole with CH₃(CH₂)₅S– substituent, Me | 6 | 69 | 10 | 2 | 6 |
| 8 | HO, t-Bu, benzotriazole with CH₃(CH₂)₇S– substituent, Me | 8 | 50~63 | 11 | 1 | 6 |

TABLE 13-continued

| Compound No. | Structure | Number of carbon atoms of $R^{13a}$ | Melting point | ⊙ and ○ | X | Evaluation |
|---|---|---|---|---|---|---|
| 9 | CH₃(CH₂)₉S-benzotriazole-N-(2-HO-3-t-Bu-5-Me-phenyl) | 10 | 68~69 | 11 | 1 | 6 |
| 10 | CH₃(CH₂)₁₁S-benzotriazole-N-(2-HO-3-t-Bu-5-Me-phenyl) | 12 | 70~72 | 7 | 3 | 4 |
| 11 | CH₃(CH₂)₁₇S-benzotriazole-N-(2-HO-3-t-Bu-5-Me-phenyl) | 18 | 73~83 | 1 | 11 | 1 |
| 12 | CH₃(CH₂)₇S-benzotriazole-N-(2-HO-3,5-di-t-Bu-phenyl) | 8 | 80~81 | 7 | 4 | 3 |
| 13 | CH₃(CH₂)₁₁S-benzotriazole-N-(2-HO-3,5-di-t-Bu-phenyl) | 12 | 64~66 | 3 | 7 | 2 |

3. Evaluation of Plastic Lens (Production of Plastic Lens)

Resins respectively having the additives of the present invention and conventional ultraviolet absorbers added thereto were produced. In the following Examples and Comparative Examples, the amount of addition of each ultraviolet absorber was adjusted such that the transmittance of 420 nm of flat lenses having a thickness of 2 mm would have values as close to one another as possible in the same type of resin material.

Example 71

0.49 g of Compound 8, 0.1 g of ZELEC UN manufactured by Stepan Company, 0.04 g of dibutyltin dichloride, and 50.8 g of a mixture of 2,5-bis(isocyanatomethyl)-bicyclo[2,2,1]heptane and 2,6-bis(isocyanatomethyl)-bicyclo[2,2,1]heptane were introduced into a flask, and the mixture was stirred for one hour at 25° C. to completely dissolve. Subsequently, 22.4 g of pentaerythritol tetrakis(3-mercaptopropionate) and 26.8 g of 1,2-bis[(2-mercaptoethyl)thio]-3-mercaptopropane were added to this mixed liquid, and the mixture was mixed for 30 minutes at 25° C. Meanwhile, Compound 8 was included in the preparation liquid in an amount of 0.49% by weight with respect to the total weight of polymerizable compounds.

This preparation liquid was subjected to degassing for one hour at 0.3 mmHg or less, and to filtration through a 5-μm PTFE filter. The preparation liquid was injected into a molding mold formed from a glass mold for flat plate having a center thickness of 2 mm and a diameter of 80 mm and a tape. This mold was slowly heated from 25° C. to 130° C., maintained at 130° C. for 2 hours, and then cooled to room temperature. The time taken from the initiation of temperature increase to cooling was 18 hours. After completion of polymerization, the molded product thus obtained was released from the mold, and this flat lens was subjected to annealing for 2 hours at 130° C.

Example 72

A flat lens having a thickness of 2 mm was obtained by a method similar to that used in Example 71, except that Compound 8 of Example 71 was added in an amount of 0.53 g (0.53% by weight with respect to the total weight of polymerizable compounds).

Example 73

0.53 g of Compound 8 (0.53% by weight with respect to the total weight of polymerizable compounds), 0.1 g of ZELEC UN manufactured by Stepan Company, 0.2 g of dibutyltin dichloride, and 58.9 g of dicyclohexylmethane-4,4'-diisocyanate were introduced into a flask, and the mixture was stirred for one hour at 25° C. to completely dissolve. Subsequently, 41.1 g of a mixture including 5,7-dimercaptomethyl-1,11-dimercapto-3,6,9-trithiaundecane, 4,7-dimercaptomethy-1,11-dimercapto-3,6,9-trithiaundecane, and 4,8-dimercaptomethyl-1,11-dimercapto-3,6,9-trithiaundecane as main components was added to the mixed liquid, and the resulting mixture was mixed for 30 minutes at 25° C.

A flat lens having a thickness of 2 mm was obtained by a method similar to that used in Example 71, except for the production of the preparation liquid.

Example 74

0.27 g of Compound 8 (0.27% by weight with respect to the total weight of polymerizable compounds), 0.1 g of ZELEC UN manufactured by Stepan Company, 0.006 g of dibutyltin dichloride, and 50.6 g of m-xylene diisocyanate were introduced into a flask, and the mixture was stirred for one hour at 25° C. to completely dissolve. Subsequently, 49.4 g of a mixture including 5,7-dimercaptomethyl-1,11-dimercapto-3,6,9-trithiaundecane, 4,7-dimercaptomethy-1,11-dimercapto-3,6,9-trithiaundecane, and 4,8-dimercaptomethyl-1,11-dimercapto-3,6,9-trithiaundecane as main components was added to the mixed liquid, and the resulting mixture was mixed for 30 minutes at 25° C.

A flat lens having a thickness of 2 mm was obtained by a method similar to that used in Example 71, except for the production of the preparation liquid.

Example 75

0.23 g of Compound 8 (0.23% by weight with respect to the total weight of polymerizable compounds), 71 g of bis(β-epithiopropyl) sulfide, 23 g of sulfur, and 2.2 g of (2-mercaptoethyl) sulfide were introduced into a flask, and the mixture was stirred for 30 minutes at 60° C. Subsequently, 0.14 g of 2-mercapto-1-methylimidazole was introduced thereinto, and the mixture was subjected to degassing for 10 minutes at 0.3 mmHg or less. Subsequently, the mixture was stirred for 120 minutes at 60° C., and then the mixture was cooled to 30° C. for 40 minutes. To the solution thus obtained, a solution obtained by dissolving 0.012 g of triethylbenzylammonium chloride and 0.01 g of dibutyltin dichloride in 3.8 g of (2-mercaptoethyl) sulfide was added dropwise, and the mixture was degassed for 20 minutes at 0.3 mmHg or less. This solution was filtered through a 5-μm PTFE filter, and was injected into a molding mold formed from a glass mold for flat plate having a center thickness of 2 mm and a diameter of 80 mm and a tape. This mold was slowly heated from 25° C. to 110° C., maintained at 1100° C. for 2 hours, and then cooled to room temperature. The time taken from the initiation of temperature rise to cooling was 18 hours. After completion of polymerization, the molded product thus obtained was released from the mold, and this flat lens was subjected to annealing for 2 hours at 110° C.

Example 76

A flat lens having a thickness of 2 mm was obtained by a method similar to that used in Example 71, except that Compound 8 of Example 71 was changed to Compound 10, and Compound 10 was added in an amount of 0.56 g (0.56% by weight with respect to the total weight of polymerizable compounds).

Example 77

A flat lens having a thickness of 2 mm was obtained by a method similar to that used in Example 71, except that Compound 8 of Example 71 was changed to Compound 14, and Compound 14 was added in an amount of 0.58 g (0.58% by weight with respect to the total weight of polymerizable compounds).

Comparative Example 14

A flat lens having a thickness of 2 mm was obtained by a method similar to that used in Example 71, except that Compound 8 of Example 71 was changed to 2-(2-hydroxy-3-t-butyl-5-methylphenyl)-chlorobenzotriazole (Compound 36), and this compound was added in an amount of 0.75 g (0.75% by weight with respect to the total weight of polymerizable compounds).

Comparative Example 15

A flat lens having a thickness of 2 mm was obtained by a method similar to that used in Example 71, except that Compound 36 of Comparative Example 14 was added in an amount of 0.85 g (0.85% by weight with respect to the total weight of polymerizable compounds).

Comparative Example 16

A flat lens having a thickness of 2 mm was obtained by a method similar to that used in Example 71, except that Compound 8 of Example 73 was changed to 2-(2-hydroxy-3-t-butyl-5-methylphenyl)-chlorobenzotriazole (Compound 36), and this compound was added in an amount of 0.75 g (0.75% by weight with respect to the total weight of polymerizable compounds).

Comparative Example 17

A flat lens having a thickness of 2 mm was obtained by a method similar to that used in Example 71, except that Compound 8 of Example 74 was changed to 2-(2-hydroxy-3-t-butyl-5-methylphenyl)-chlorobenzotriazole (Compound 36), and this compound was added in an amount of 0.50 g (0.50% by weight with respect to the total weight of polymerizable compounds).

Comparative Example 18

A flat lens having a thickness of 2 mm was obtained by a method similar to that used in Example 75, except that Compound 8 of Example 75 was changed to 2-(2-hydroxy-3-t-butyl-5-methylphenyl)-chlorobenzotriazole (Compound 36), and this compound was added in an amount of 0.30 g (0.30% by weight with respect to the total weight of polymerizable compounds).

(1) Transmittance, Yellow Index (YI Value), and Visual Transmittance

For the sample lenses produced in Examples and Comparative Examples, the spectral transmittance for 350 to 800 nm, the yellow index (YI value), and the visual transmittance were measured using an ultraviolet-visible spectrophotometer (U-4100 manufactured by Hitachi High-Technologies Corp.). The yellow index and the visual transmittance were determined as values obtained under the conditions of a 2-degree viewing field with a D65 light source.

(2) Evaluation of External Appearance of Sample Lenses

For the sample lenses thus produced, yellowness of the sample lenses of Examples and Comparative Examples in which the transmittances for near 420 nm in the same resin material were close to one another, was compared and checked by visual inspection. It is because since the yellowness originally possessed by a resin itself varies depending on the type of the resin, yellowness obtainable by adding an ultraviolet absorber cannot be accurately compared in different resins. The lenses used for comparison were specifically Example 71 with Comparative Example 14, Example 72 with Comparative Example 15, Example 73 with Comparative Example 16, Example 74 with Comparative Example 17, Example 75 with Comparative example 18, Example 76 with Comparative Example 14, and Example 77 with Comparative Example 14. The external appearance was evaluated by the following criteria. Furthermore, precipitation of the ultraviolet absorber from the resin and transparency were checked by visual inspection.

Yellowness . . . ◯: Closer to colorlessness, x: Yellow

The YI values and the results for external appearance are presented in Table 14, and the results for measuring transmission spectra are presented in FIG. 10 to FIG. 16.

When it is attempted to cut wavelengths in the wavelength region of 400 to 420 nm using an ultraviolet absorber, depending on the type of the ultraviolet absorber, yellowing of the resin may occur, or the ultraviolet absorber is precipitated out without being able to be dissolved in the resin of a plastic lens, so that the resin may be clouded. For example, it is described in JP 4334633 B1 that when an ultraviolet absorber having a molecular weight of more than 360 is used, its degree of solubility in the raw material monomers is decreased, and the ultraviolet absorber is precipitated out on the surface of a plastic lens even if the amount of incorporation is 5 parts by weight of less. It is also described that when the ultraviolet absorber is used in the limit amount at which precipitation does not occur, a sufficient ultraviolet absorption ability is not obtained, and it is difficult to obtain a plastic lens capable of sufficiently absorbing ultraviolet ray having a wavelength of 380 to 400 nm. However, in regard to the additives of the present invention, it was confirmed that due to their structural features, despite that Compounds 8, 10 and 14 have molecular weights of more than 360 compared to the molecular weight of 316 of Compound 36, the compounds satisfactorily dissolve in monomers similarly to Compound 36, are not precipitated out on the surface of plastic lenses thus obtained, and manifest affinity to monomers and plastic lenses due to the structure of the ultraviolet absorber of the present invention.

Furthermore, a plastic lens using an ultraviolet absorber represented by Formula (I) absorbs light having a wavelength of 400 to 420 nm more efficiently with a smaller amount of addition, compared to a lens using 2-(2-hydroxy-3-t-butyl-5-methylphenyl)-chlorobenzotriazole. Thus, a lens which has satisfactory transmissibility for light having a wavelength of near 420 nm or longer while suppressing adverse effects to the eye, suppresses yellowing of a plastic lens, and has excellent external appearance, was obtained.

Therefore, it was recognized that the additive of the present invention has satisfactory compatibility with a resin serving as a matrix, and can sufficiently exhibit performances such as ultraviolet absorption and imparting of a high refractive index while maintaining high transparency.

TABLE 14

| Type of ultraviolet absorber | Example 71 Compound 8 (Compound 1) | Comparative Example 14 Compound 36 (2-(2-hydroxy-3-t-butyl-5-methylphenyl)-chlorobenzo-triazole) | Example 72 Compound 8 (Compound 1) | Comparative Example 15 Compound 36 (2-(2-hydroxy-3-t-butyl-5-methylphenyl)-chlorobenzo-triazole) | Example 73 Compound 8 (Compound 1) | Comparative Example 16 Compound 36 (2-(2-hydroxy-3-t-butyl-5-methylphenyl)-chlorobenzo-triazole) |
|---|---|---|---|---|---|---|
| Proportion of addition of ultraviolet absorber (%) | 0.49 | 0.75 | 0.53 | 0.85 | 0.53 | 0.75 |
| Resin refractive index | 1.60 | 1.60 | 1.60 | 1.60 | 1.60 | 1.60 |
| 410 nm transmittance (%) | 0.9 | 1.3 | 1.0 | 1.1 | 1.0 | 1.2 |
| 415 nm transmittance (%) | 5.6 | 8.4 | 4.8 | 6.4 | 6.5 | 8.3 |
| 420 nm transmittance (%) | 29.0 | 29.8 | 26.4 | 26.2 | 31.5 | 30.0 |
| 425 nm transmittance (%) | 58.7 | 55.8 | 56.7 | 52.8 | 60.8 | 56.1 |
| 430 nm transmittance (%) | 77.0 | 73.9 | 75.7 | 71.8 | 77.6 | 73.8 |
| 440 nm transmittance (%) | 88.0 | 86.7 | 87.4 | 86.5 | 87.0 | 86.4 |
| Luminous transmittance (%) | 89.8 | 89.4 | 90.2 | 90.0 | 89.4 | 89.4 |
| (Transmittance at 425 nm) − (transmittance at 420 nm) | 29.7 | 26.0 | 30.3 | 26.6 | 29.2 | 26.1 |
| (Transmittance at 425 nm) − (transmittance at 415 nm) | 53.1 | 47.4 | 51.9 | 46.4 | 54.2 | 47.8 |
| [(Transmittance at 425 nm) − (transmittance at 415 nm)] × (resin refractive index − 0.6) | 53.1 | 47.4 | 51.9 | 46.4 | 54.2 | 47.8 |
| YI | 7.6 | 8.2 | 8.0 | 8.6 | 7.3 | 8.1 |
| Comparison on coloration (yellowing) | ◯ | X | ◯ | X | ◯ | X |
| Precipitation of ultraviolet absorber from resin | Absent Transparent | Absent Transparent | Absent Transparent | Absent Transparent | Absent Transparent | Absent Transparent |

TABLE 14-continued

| Type of ultraviolet absorber | Example 74 Compound 8 (Compound 1) | Comparative Example 17 Compound 36 (2-(2-hydroxy-3-t-butyl-5-methylphenyl)-chlorobenzo-triazole) | Example 75 Compound 8 (Compound 1) | Comparative Example 18 Compound 36 (2-(2-hydroxy-3-t-butyl-5-methylphenyl)-chlorobenzo-triazole) | Example 76 Compound 10 (Compound 2) | Example 77 Compound 14 (Compound 4) |
|---|---|---|---|---|---|---|
| Proportion of addition of ultraviolet absorber (%) | 0.27 | 0.50 | 0.23 | 0.30 | 0.56 | 0.58 |
| Resin refractive index | 1.67 | 1.67 | 1.76 | 1.76 | 1.60 | 1.60 |
| 410 nm transmittance (%) | 0.9 | 1.1 | 0.7 | 0.9 | 0.8 | 1.0 |
| 415 nm transmittance (%) | 4.9 | 6.7 | 2.3 | 5.8 | 6.1 | 7.7 |
| 420 nm transmittance (%) | 26.3 | 24.8 | 17.7 | 22.5 | 30.1 | 32.7 |
| 425 nm transmittance (%) | 54.4 | 49.7 | 46.9 | 46.2 | 58.8 | 60.3 |
| 430 nm transmittance (%) | 72.6 | 68.8 | 67.8 | 64.7 | 76.0 | 76.6 |
| 440 nm transmittance (%) | 84.7 | 84.1 | 81.5 | 79.8 | 87.0 | 86.5 |
| Luminous transmittance (%) | 88.3 | 88.2 | 85.9 | 85.8 | 89.5 | 89.4 |
| (Transmittance at 425 nm) − (transmittance at 420 nm) | 28.0 | 24.9 | 29.2 | 23.7 | 28.7 | 27.6 |
| (Transmittance at 425 nm) − (transmittance at 415 nm) | 49.4 | 43.0 | 44.6 | 40.4 | 52.7 | 52.6 |
| [(Transmittance at 425 nm) − (transmittance at 415 nm)] × (resin refractive index − 0.6) | 52.9 | 46.0 | 51.7 | 46.9 | 52.7 | 52.6 |
| YI | 8.5 | 9.3 | 10.0 | 10.8 | 7.9 | 7.7 |
| Comparison on coloration (yellowing) | ○ | X | ○ | X | ○ | ○ |
| Precipitation of ultraviolet absorber from resin | Absent Transparent | Absent Transparent | Absent Transparent | Absent Transparent | Absent Transparent | Absent Transparent |

4. Evaluation of Immobilization of Additive Having Reactive Functional Group to Resin 0.022 g of an isocyanate (HC-210 manufactured by Nippon Polyurethane Industry Co., Ltd.), 0.078 g of a polyol (ON-H37 manufactured by Nippon Polyurethane Industry Co., Ltd.), and 0.002 g of each compound of Compounds 1 and 20 were uniformly mixed with 12 g of chloroform, and about 1 mL of the mixture was spin coated on a glass substrate under the conditions of 1,500 rpm and 20 seconds. Subsequently, chloroform was removed in an oven at 45° C., and then the residue was heated for 3 hours at 100° C. Thus, a urethane film was produced.

The film thus obtained was immersed in warm water at 70° C., and the absorbance at the maximum absorption wavelength of Compound 1 or 20 was measured at a certain interval of time.

[(Absorbance after 10 or 40 hours/initial absorbance)× 100] was designated as the absorbance retention ratio (%), and the absorbance retention ratios after 10 hours and after 40 hours were measured for the compounds of Examples 1 and 20. The film retained transparency, and thus the absorbance retention ratio of the film exhibited values almost close to the initial values.

2.5 g of methyl methacrylate, 0.05 g of Compound 17, and 10 g of toluene and 10 g of methyl ethyl ketone (MEK) as solvents were introduced together with 0.025 g of 1,1'-azobis(cyclohexane-1-carbonitrile) as a polymerization initiator, and the mixture was stirred for one hour in a nitrogen atmosphere. Subsequently, a polymerization reaction was performed at a reaction temperature of 88° C. to 91° C. in a state of being heated to reflux for 10 hours. 250 g of MEK was added to the copolymer solution thus obtained, and the solution was dropped from a dropping funnel into 2,500 g of methanol over one hour. The crystals of a copolymer were precipitated out. Next, filtration, purification, and drying under reduced pressure were performed, and thus 2.12 g of a methacrylic resin was obtained.

0.10 g of the methacrylic resin thus obtained was heated to melt at 280° C., and then the resin was dropped on a slide glass substrate, quickly spread thereon, and air-cooled. Thus, a film was produced.

The film thus obtained was immersed in warm water at 70° C., and the absorbance at the maximum absorption wavelength of Compound 17 was measured after 10 hours and after 40 hours. The absorbance retention ratios were measured in the same manner as described above. The film retained transparency, and thus the absorbance retention ratio of the film exhibited values almost close to the initial values.

That is, it was confirmed that elution of the additives having a reactive functional group into monomers or resins does not occur, the additives and the monomers react with each other so that the additives are immobilized in resins, the resins maintain transparency without bleedout of the additives, and the resins can be respectively maintained the functions of ultraviolet absorbency and imparting of a high refractive index for a long period of time.

The invention claimed is:

1. A resin composition for a transparent resin member comprising a resin and an additive, wherein the additive is represented by the following Formula (IA):

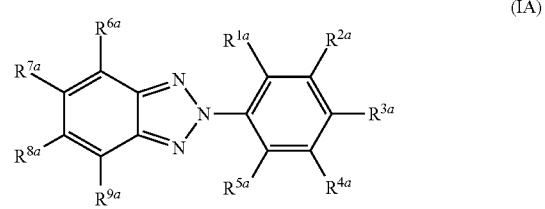

(IA)

wherein:
R$^{1a}$ to R$^{5a}$ each independently represent a hydrogen atom, a methyl group, a t-butyl group, or a hydroxyl group, wherein R$^{1a}$ to R$^{5a}$ contain no more than one t-butyl group;
R$^{6a}$ to R$^{9a}$ each represent a sulfur-containing monovalent group represented by the following Formula (i-2) or a hydrogen atom, wherein at least one of R$^{6a}$ to R$^{9a}$ represents the sulfur-containing monovalent group of Formula (i-2):

  (i-2)

n and p each represent 0;
R$^{13a}$ represents a reactive functional group selected from the group consisting of a hydrocarbon group substituted with a hydroxyl group, a hydrocarbon group substituted with a mercapto group, a hydrocarbon group substituted with a carboxyl group, a hydrocarbon group substituted with an amino group, a hydrocarbon group substituted with a silyl group and a group containing a carbon-carbon double bond, wherein the hydrocarbon group is that in which (1) the hydrocarbon group is optionally interrupted by a divalent group between —R$^{13a}$ and the sulfur atom in Formula (i-2), (2) a hydrogen atom in the hydrocarbon group is optionally replaced with a monovalent group, or (3) a carbon-carbon bond in the hydrocarbon group is interrupted by a divalent group between two carbon atoms of the carbon-carbon bond, wherein the monovalent and divalent group are each independently selected from the group consisting of an aromatic group, an unsaturated group, a sulfur-containing group, an oxygen-containing group, a phosphorus-containing group, an alicyclic group and a halogen atom.

2. The resin composition according to claim 1, wherein the reactive functional group is a hydrocarbon group substituted with a hydroxyl group or a group containing a carbon-carbon double bond, wherein the group containing a carbon-carbon double bond is selected from the group consisting of a vinyl group, a vinyloxy group, an allyl group, a (meth)acryloyl group, a maleoyl group, a styryl group, a cinnamoyl group and a hydrocarbon group substituted with one of these groups, wherein the hydrocarbon group is that in which (1) the hydrocarbon group is optionally interrupted by a divalent group between —R$^{13a}$ and the sulfur atom in Formula (i-2), (2) a hydrogen atom in the hydrocarbon group is optionally replaced with a monovalent group, or (3) a carbon-carbon bond in the hydrocarbon group is interrupted by a divalent group between two carbon atoms of the carbon-carbon bond, wherein the monovalent and divalent group are each independently selected from the group consisting of an aromatic group, an unsaturated group, a sulfur-containing group, an oxygen-containing group, a phosphorus-containing group, an alicyclic group and a halogen atom.

3. The resin composition according to claim 2, wherein the monovalent and divalent group are each independently selected from the group consisting of an aromatic group and an oxygen-containing group.

4. The resin composition according to claim 1, wherein the hydrocarbon group of R$^{13a}$ is an alkyl group having 1 to 8 carbon atoms.

5. The resin composition according to claim 1, wherein the resin is a thermoplastic resin.

6. The resin composition according to claim 5, wherein the thermoplastic resin is selected from the group consisting of an acrylic resin, polyurethane, polythiourethane, polyethylene terephthalate, polystyrene and polycarbonate.

7. The resin composition according to claim 1, wherein the resin is a thermosetting resin other than an acrylic melamine resin.

8. The resin composition according to claim 7, wherein the thermosetting resin is selected from the group consisting of an urethane resin, an urea resin, a melamine resin and an episulfide resin.

9. A transparent resin member comprising the resin composition according to claim 1.

10. A resin composition for a transparent resin member comprising a resin and an additive, wherein the additive is represented by the following Formula (IB):

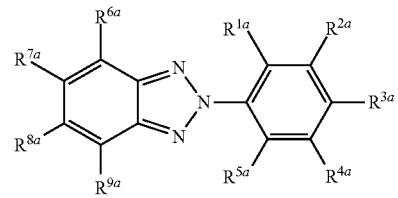  (IB)

wherein:
R$^{1a}$ to R$^{5a}$ each independently represent a hydrogen atom, a methyl group, a t-butyl group, or a hydroxyl group, wherein R$^{1a}$ to R$^{5a}$ contain no more than one t-butyl group;
R$^{6a}$ to R$^{9a}$ each represent a sulfur-containing monovalent group represented by the following Formula (i-2) or a hydrogen atom, wherein at least one of R$^{6a}$ to R$^{9a}$ represents the sulfur-containing monovalent group of Formula (i-2):

  (i-2)

n and p each represent 0;
R$^{13a}$ represents a cyclohexyl group or an alkyl group, wherein the alkyl group is interrupted by a cyclohexyl group between —R$^{13a}$ and the sulfur atom in Formula (i-2).

11. The resin composition according to claim 10, wherein the resin is a thermoplastic resin.

12. The resin composition claim 11, wherein the thermoplastic resin is selected from the group consisting of an acrylic resin, polyurethane, polythiourethane, polyethylene terephthalate, polystyrene and polycarbonate.

13. The resin composition according to claim 10, wherein the resin is a thermosetting resin other than an acrylic melamine resin.

14. The resin composition according to claim 13, wherein the thermosetting resin is selected from the group consisting of an urethane resin, an urea resin, a melamine resin and an episulfide resin.

15. A transparent resin member comprising the resin composition according to claim 10.

16. A resin composition for a transparent resin member comprising a resin and an additive, wherein the additive is represented by the following Formula (IC):

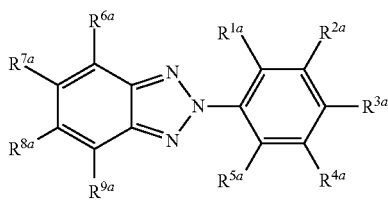

wherein:
$R^{1a}$ to $R^{9a}$ each independently represent a monovalent group selected from the group consisting of a monovalent sulfur-containing group represented by the following Formula (i-2), a hydrogen atom, a hydrocarbon group having 1 to 10 carbon atoms, an aromatic group, an unsaturated group, a sulfur-containing group, an oxygen-containing group, a phosphorus-containing group, an alicyclic group, and a halogen atom:

wherein in Formula (i-2),
$R^{11a}$ represents a divalent hydrocarbon group having 1 to 20 carbon atoms, wherein (1) a hydrogen atom in the divalent hydrocarbon group is optionally replaced with a monovalent group, (2) the divalent hydrocarbon group is optionally interrupted by a divalent group between —$R^{11a}$— and a carbon atom at a position selected from $R^{1a}$ to $R^{9a}$ in Formula (IC) and/or between —$R^{11a}$— and the sulfur atom in Formula (i-2), or (3) a carbon-carbon bond in the divalent hydrocarbon group is optionally interrupted by a divalent group between two carbon atoms of the carbon-carbon bond, the monovalent and divalent group are each independently selected from the group consisting of an aromatic group, an unsaturated group, a sulfur-containing group, an oxygen-containing group, a phosphorus-containing group, an alicyclic group and a halogen atom;
$R^{12a}$ represents, or if p is 2 or larger, $R^{12a}$'s each independently represent, a divalent hydrocarbon group having 1 to 20 carbon atoms, wherein (1) a hydrogen atom in the divalent hydrocarbon group is optionally replaced with a monovalent group, (2) the divalent hydrocarbon group is optionally interrupted by a divalent group between —$R^{12a}$— and at least one of sulfur atoms in Formula (i-2), or (3) a carbon-carbon bond in the divalent hydrocarbon group is optionally interrupted by a divalent group between two carbon atoms of the carbon-carbon bond, the monovalent and divalent group are each independently selected from the group consisting of an aromatic group, an unsaturated group, a sulfur-containing group, an oxygen-containing group, a phosphorus-containing group, an alicyclic group and a halogen atom;
$R^{13a}$ represents a hydrogen atom, or a group represented by —$(R^{14a})_l$—$R^{15a}$,
$R^{14a}$ represents a divalent hydrocarbon group having 1 to 20 carbon atoms, wherein (1) a hydrogen atom in the divalent hydrocarbon group is optionally replaced with a monovalent group, (2) the divalent hydrocarbon group is optionally interrupted by a divalent group between —$R^{14a}$— and the sulfur atom in Formula (i-2), or (3) a carbon-carbon bond in the divalent hydrocarbon group is optionally interrupted by a divalent group between two carbon atoms of the carbon-carbon bond, the monovalent and divalent group are each independently selected from an aromatic group, an unsaturated group, a sulfur-containing group, an oxygen-containing group, a phosphorus-containing group, an alicyclic group and a halogen atom;
$R^{15a}$ represents a hydrogen atom, or a substituent containing any one skeleton selected from benzotriazole, benzophenone, a benzoic acid ester and triazine; and
l represents an integer of 0 to 1;
the total number of carbon atoms of $R^{11a}$, $R^{12a}$, and $R^{13a}$ is 25 or less;
n represents an integer of 0 or 1;
p represents an integer from 0 to 3; and
the monovalent sulfur-containing group of Formula (i-2) is present at one or more of the positions of $R^{1a}$ to $R^{5a}$.

17. The resin composition according to claim 16, wherein $R^{11a}$ and $R^{12a}$ are each an alkylene group having 18 or fewer carbon atoms; and $R^{13a}$ is an alkyl group having 18 or fewer carbon atoms.

18. The resin composition according to claim 16, wherein $R^{11a}$ and $R^{12a}$ are each an alkylene group having 8 or fewer carbon atoms; and $R^{13a}$ is an alkyl group having 8 or fewer carbon atoms.

19. The resin composition according to claim 16, wherein the resin is a thermoplastic resin.

20. The resin composition claim 19, wherein the thermoplastic resin is selected from the group consisting of an acrylic resin, polyurethane, polythiourethane, polyethylene terephthalate, polystyrene and polycarbonate.

21. The resin composition according to claim 17, wherein the resin is a thermosetting resin other than an acrylic melamine resin.

22. The resin composition according to claim 21, wherein the thermosetting resin is selected from the group consisting of an urethane resin, an urea resin, a melamine resin and an episulfide resin.

23. A transparent resin member comprising the resin composition according to claim 16.

24. The resin composition according to claim 1, wherein at least $R^{1a}$ represents a hydroxyl group.

25. The resin composition according to claim 24, wherein at least $R^{2a}$ and $R^{4a}$ represent a t-butyl group or a methyl group.

26. The resin composition according to claim 25, wherein $R^{2a}$ represents a t-butyl group and at least $R^{4a}$ represents a methyl group.

27. The resin composition according to claim 10, wherein at least $R^{1a}$ represents a hydroxyl group.

28. The resin composition according to claim 27, wherein at least $R^{2a}$ and $R^{4a}$ represent a t-butyl group or a methyl group.

29. The resin composition according to claim 28, wherein $R^{2a}$ represents a t-butyl group and at least $R^{4a}$ represents a methyl group.

30. A resin composition for a transparent resin member comprising a resin and an additive, wherein the additive is represented by the following Formula (ID):

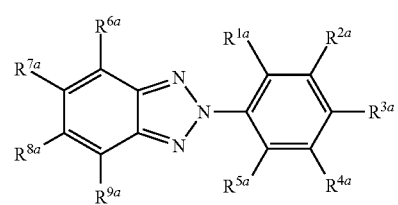

wherein:
R$^{1a}$ to R$^{5a}$ each independently represent a hydrogen atom, a methyl group, a t-butyl group, or a hydroxyl group, wherein R$^{1a}$ to R$^{5a}$ contain no more than one t-butyl group;
R$^{6a}$ to R$^{9a}$ each represent a sulfur-containing monovalent group represented by the following Formula (i-2) or a hydrogen atom, wherein at least one of R$^{6a}$ to R$^{9a}$ represents the sulfur-containing monovalent group of Formula (i-2):

  (i-2)

n and p each represent 0; and
R$^{13a}$ represents an aromatic group or an alkyl group, wherein (1) the alkyl group is interrupted by an aromatic group between —R$^{13a}$ and the sulfur atom in Formula (i-2), (2) a hydrogen atom in the alkyl group is replaced with an aromatic group, or (3) a carbon-carbon bond in the alkyl group is interrupted by an aromatic group between two carbon atoms of the carbon-carbon bond, and
wherein the resin is a thermosetting resin.

31. The resin composition according to claim 30, wherein the resin is a thermosetting resin other than an acrylic melamine resin.

32. The resin composition according to claim 31, wherein the thermosetting resin is selected from the group consisting of a urethane resin, a thiourethane resin, an urea resin, a melamine resin, an episulfide resin, an epoxy resin, an allyl resin, a silicone resin, a phenol resin and an unsaturated polyester.

33. The resin composition according to claim 32, wherein the thermosetting resin is selected from the group consisting of an urethane resin, an urea resin, a melamine resin and an episulfide resin.

34. The resin composition according to claim 31, wherein the resin is an episulfide resin.

35. A resin composition for a transparent resin member comprising a resin and an additive, wherein the additive is represented by the following Formula (IE):

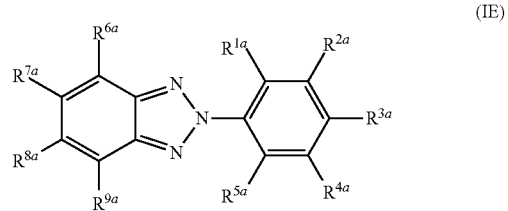 (IE)

wherein:
R$^{1a}$ to R$^{5a}$ each independently represent a hydrogen atom, a methyl group, a t-butyl group, or a hydroxyl group, wherein R$^{1a}$ to R$^{5a}$ contain no more than one t-butyl group;
R$^{6a}$ to R$^{9a}$ each represent a sulfur-containing monovalent group represented by the following Formula (i-2) or a hydrogen atom, wherein at least one of R$^{6a}$ to R$^{9a}$ represents the sulfur-containing monovalent group of Formula (i-2):

 (i-2)

n and p each represent 0; and
R$^{13a}$ represents an alkyl group, wherein the alkyl group is interrupted by an aromatic group between —R$^{13a}$ and the sulfur atom in Formula (i-2).

36. The resin composition according to claim 35, wherein the aromatic group is a phenyl group.

* * * * *